(12) United States Patent
Amato et al.

(10) Patent No.: US 11,141,526 B2
(45) Date of Patent: Oct. 12, 2021

(54) COMPOSITIONS, DEVICES AND KITS FOR SELECTIVE INTERNAL RADIATION THERAPY

(71) Applicant: BetaGlue Technologies S.p.A, Verona (IT)

(72) Inventors: Antonino Amato, Rome (IT); Giovanni Paganelli, Cesena (IT)

(73) Assignee: BetaGlue Technologies S.p.A, Verona (IT)

( * ) Notice: Subject to any disclaimer, the term of this patent is extended or adjusted under 35 U.S.C. 154(b) by 0 days.

(21) Appl. No.: 16/872,295

(22) Filed: May 11, 2020

(65) Prior Publication Data
US 2021/0128819 A1    May 6, 2021

Related U.S. Application Data

(60) Provisional application No. 62/929,692, filed on Nov. 1, 2019, provisional application No. 63/005,172, filed on Apr. 3, 2020.

(51) Int. Cl.
*A61M 5/19* (2006.01)
*A61M 5/32* (2006.01)
(Continued)

(52) U.S. Cl.
CPC ............ *A61M 5/007* (2013.01); *A61J 1/2096* (2013.01); *A61K 51/1213* (2013.01);
(Continued)

(58) Field of Classification Search
CPC .......... A61N 5/1001–1027; A61N 5/10–1084; A61N 2005/1085–1098; A61M 5/007;
(Continued)

(56) References Cited

U.S. PATENT DOCUMENTS

| 4,619,913 A | 10/1986 | Luck et al. |
| 4,932,942 A | 6/1990 | Maslanka |

(Continued)

FOREIGN PATENT DOCUMENTS

| CA | 2636980 A1 | 2/2009 |
| EP | 0167263 A1 | 1/1986 |

(Continued)

OTHER PUBLICATIONS

McArdle et al., "Cytotoxic-loaded albumin microspheres: a novel approach to regional chemotherapy," Br. J. Surg. 1988, vol. 76, p. 132-134. (Year: 1988).*

(Continued)

*Primary Examiner* — Thaddeus B Cox
(74) *Attorney, Agent, or Firm* — Dorsey & Whitney LLP

(57) ABSTRACT

Systems, kits and methods for preparing an injection system and/or treating target lesions with a selective internal radiation therapy which includes a double-barrel syringe loaded with a two-component tissue glue and radioisotope loaded microspheres. The microspheres are loaded into the syringe based on the size of the target location and are administered with a needle or dual-lumen catheter. Dosing regimens for treating breast cancer lesions or surgical beds up to 130 mm in diameter and hepatocellular carcinoma lesions up to 50 mm are included.

11 Claims, 25 Drawing Sheets

(51) Int. Cl.
  A61M 5/178     (2006.01)
  A61K 51/12     (2006.01)
  A61N 5/10      (2006.01)
  A61M 5/00      (2006.01)
  A61J 1/20      (2006.01)

(52) U.S. Cl.
  CPC ....... *A61K 51/1251* (2013.01); *A61M 5/1785* (2013.01); *A61M 5/19* (2013.01); *A61M 5/3294* (2013.01); *A61N 5/1007* (2013.01); *A61N 5/1027* (2013.01); *A61N 5/1031* (2013.01); *A61M 2205/583* (2013.01); *A61M 2210/1007* (2013.01); *A61N 2005/1098* (2013.01)

(58) Field of Classification Search
  CPC .... A61M 5/3294; A61M 5/19; A61M 5/1785; A61K 51/1213; A61K 51/1251; A61K 51/00–1296; A61J 1/2096
  See application file for complete search history.

(56) References Cited

U.S. PATENT DOCUMENTS

| | | | |
|---|---|---|---|
| RE33,375 E | 10/1990 | Luck et al. | |
| 5,322,510 A | 6/1994 | Lindner et al. | |
| 5,597,578 A | 1/1997 | Brown et al. | |
| 5,814,022 A | 9/1998 | Antanavich et al. | |
| 2002/0168319 A1* | 11/2002 | Filler | A61L 24/0015 424/1.69 |
| 2004/0197264 A1 | 10/2004 | Schwarz et al. | |
| 2004/0258614 A1 | 12/2004 | Line et al. | |
| 2009/0131734 A1 | 5/2009 | Neustadter et al. | |
| 2009/0324720 A1 | 12/2009 | He et al. | |
| 2011/0142804 A1* | 6/2011 | Gaudette | A61L 27/3834 424/93.7 |
| 2014/0163664 A1 | 6/2014 | Goldsmith | |
| 2014/0248209 A1* | 9/2014 | Di Capua | A61K 9/0024 424/1.11 |
| 2015/0118495 A1 | 4/2015 | Day et al. | |
| 2017/0056009 A1* | 3/2017 | Shelton, IV | A61B 6/481 |
| 2017/0209606 A1* | 7/2017 | Azab | A61K 51/1213 |

FOREIGN PATENT DOCUMENTS

| | | | | |
|---|---|---|---|---|
| FR | 2722104 A3 | 1/1996 | | |
| IT | 200900969 | 12/2010 | | |
| WO | 03039375 A2 | 5/2003 | | |
| WO | 2005079757 A2 | 9/2005 | | |
| WO | 2008151456 A1 | 12/2008 | | |
| WO | 2010140179 A1 | 12/2010 | | |
| WO | WO-2010140179 A1 * | 12/2010 | ....... A61B 17/00491 | |
| WO | 2013057747 A1 | 4/2013 | | |

OTHER PUBLICATIONS

Ali Asgar Attarwala, et al. "Quantitative and Qualitative Assessment of Yttrium-90 PET/CT Imaging" Plos One, Nov. 2014, vol. 9, Issue 11.

Invitation to Pay Additional Fees for PCT Application No. PCT/IB2020/060247, dated Feb. 4, 2021.

Marco D'Arienzo, et al. "Phantom validation of quantitative Y-90 PET/CT-based dosimetry in liver radioembolization" EJNMMI Research, 2017.

Nima Kokabi, etal. "A Simple Method for Estimating Dose Delivered to Hepatocellular Carcinoma after Yttrium-90 Glass-Based Radioembolization Therapy: Preliminary Results of a Proof of Concept Study" J Vasc Interv Radiol, Feb. 2014, vol. 25, No. 2.

Package Leaflet: Information for the User—Tissell—Solutions for sealant, Feb. 2013, 22 pgs.

Shyam M. Srinivas, etal. "Determination of radiation absorbed dose to primary liver tumors and normal liver tissue using post-radioembolization" Frontiers in Oncology, Oct. 2014, vol. 4, Article 255.

Yoo Sung Song, etal. "PET/CT-Based Dosimetry in 90Y-Microsphere Selective Internal Radiation Therapy: Single Cohort Comparison With Pretreatment Planning on 99mTc-MAA Imaging and Correlation With Treatment Efficacy" Medicine Observational Study, Jun. 2015, vol. 94, No. 23.

"Hemostats, Sealants, and Adhesives: Components of the Surgical Toolbox", Spotnitz and Burks, Transfusion, 48, p. 1502-1516, 2008.

Amato, E. et al., "Absorbed Fractions for Photons in Ellipsoidal Volumes", Physics in Medicine and Biology, vol. 54. No. 20, Oct. 2009.

Arazi, , "Treatment of Solid Tumors By Interstitial Release of Recoiling Short-Lived Alpha Emitters", Physics in Medicine and Biology, vol. 52, No. 16, Aug. 2007.

Ariel, Irving M. et al., "Cure of an Embryonal Rhabdomyosarcoma of the Nose of an Infant By Interstitial 90YTTRIUM Microspheres: A Case Report", International Journal of Nuclear Medicine and Biology, vol. 5, No. 1, Mar. 1978, pp. 37-41.

Bakker, Robbert C. et al., "Intratumoral Treatment With Radioactive Beta-Emitting Microparticles: A Systematic Review", Journal of Radiation Oncology, vol. 6, No. 4, May 2017, pp. 323-341.

Bardiés, Manuel et al., "Absorbed Doses for Internal Radiotherapy From 22 Beta-Emitting Radionuclides: Beta Dosimetry of Small Spheres", Physics in Medicine and Biology, Vo. 39, No. 6, Jun. 1994, pp. 961-981.

Bé, Marine-Martine et al., "Table of Radionuclides (vol. 8-A = 41 to 198)", Bureau International des Poids Mesures, accessed May 1, 2019.

Briesmeister, Judith F. et al., "MCNP™—A General Monte Carlo N-Particle Transport Code Version 4C", Los Alamos National Laboratory, Mar. 2000.

Bult, Wouter et al.. "Intratumoral Administration of HOLMIUM-166 Acetylacetonate Microspheres: Antitumor Efficacy and Feasibility of Multimodality Imaging in Renal Cancer", PLoS ONE, vol. 8, No. 1, Jan. 2013, pp. 1-7.

Chao, Hung-Hsing et al., "Bioglue Albumin/Glutaraldehyde Sealant in Cardiac Surgery", Journal of Cardiac Surgery, vol. 18. No. 6, Nov. 2003, pp. 500-503.

D'Arienzo, Marco et al., "Dosimetric Issues Associated With Percutaneous Ablation of Small Liver Lesions With 90Y", Applied Sciences, vol. 10, No. 18, Sep. 22, 2020.

DeZarn, William A. et al., "Recommendations of the American Association of Physicists in Medicine on Dosimetry, Imaging, and Quality Assurance Procedures for 90Y Microsphere Brachytherapy in the Treatment of Hepatic Malignancies", Medical Physics, vol. 38, No. 8, Aug. 2011, pp. 4824-4845.

Dieudonné, Arnaud et al., "Absorbed-Dose Calculation for Treatment of Liver Neoplasms With 90Y-Microspheres", Clinical and Translational Imaging, vol. 4, Jul. 2016, pp. 273-282.

Fabbri, C. et al., "Quantitative Evaluation on [90Y] DOTATOC Pet and Spect Imaging By Phantom Acquisitions and Clinical Applicaitons in Locoregional and Systemic Treatments", The Quarterly Journal of Nuclear Medicine and Molecular Imaging, vol. 56, No. 6, Dec. 2012, pp. 522-528.

Fabbri, Cinzia et al., "90Y-Based Pet and SPECT/CT Imaging in Locoregional Brain Treatment for High-Grade Gliomas Retrospective Fusion With MRI", European Journal of Nuclear Medicine and Molecular Imaging, vol. 39, Aug. 2012, pp. 1822-1823.

Ferrari, Mahila et al., "Dosimetric Model for Locoregional Treatments of Brain Tumors With 90Y-Conjugates: Clinical Applicaiton With 90Y-DOTATOC", Journal of Nuclear Medicine, vol. 47, No. 1, Jan. 2006, pp. 105-112.

Gulec, et al., "Safety and Efficacy of Y-90 Microsphere Treatment in Patients with Primary and Metastatic Liver Cancer: The Tumor Selectivity of the Treatment as a Function of Tumor to Liver Flow Ratio", Journal of Translational Medicine 2007, 5:15, 9 pages.

Gulec, Seza A. et al., "Dosimetric Techniques in 90Y-Microsphere Therapy of Liver Cancer: The MIRD Equations for Dose Calculations", Journal of Nuclear Medicine, vol. 47, No. 7, Jul. 2006.

(56) References Cited

OTHER PUBLICATIONS

Ho, S. et al., "Clinical Evaluation of the Partition Model for Estimation Radiation Doses From YTTRIUM-90 Microspheres in Treatment of Hepatic Cancer", European Journal of Nuclear Medicine, vol. 24, No. 3, Mar. 1997.

Ho, S. et al., "Partition Model for Estimation Radiation Doses From YTTRIUM-90 Microspheres in Treating Hepatic Tumours", European Journal of Nuclear Medicine, vol. 23, No. 8, Aug. 1996, pp. 947-952.

Hsieh, Te-Chun et al., "Treating Hepatocellular Carcinoma With 90Y-Bearing Microspheres: A Review", BioMedicine, vol. 6, No. 4, Article 1, Dec. 2016, pp. 1-7.

Hubbell, , "Atomic Form Factors, Incoherent Scattering Functions, and Photon Scattering Cross Sections", Journal of Physical and Chemical Reference Data, vol. 4. No. 3. Jul. 1975, pp. 471-538.

Izzo, Francesco et al., "Hepatocellular Carcinoma: Preclinical Data on a Dual-Lumen Catheter Kit for Fibrin Sealant Infusion Following Loco-Regional Treatments", Infectious Agents and Cancer, vol. 4, No. 39, Nov. 2014.

Kalia, J.S. et al., Using a Distal Access Catheter in Acute Stroke Intervention With Penumbra, Meri and Gateway, Interventional Neuroradiology, Dec. 2009.

Kennedy, Andrew S. et al., "Pathologic Response and Microdosimetry of 90Y Microspheres in Man: Review of Four Explanted Whole Livers", International Journal of Radiation Oncology, Biology, Physics, vol. 60, No. 5, Dec. 2004, pp. 1552-1563.

Kidd, et al., "Fibrin Hydrogels for Lentiviral Gene Delivery in Vitro and in Vivo", J. Control Release, Jan. 10, 2012; 157(1): 80-85, 17 pages.

Lau, W. Y. et al., "Treatment of inoperable hepatocellular carcinoma with intrahepatic arterial yttrium-90 microspheres: a phase I and II study", British Journal of cancer 70.5 (1994): 994-999.

Manohara, S. R. et al., "Energy absorption buildup factors of human organs and tissues at energies and penetration depths relevant for Yadiotherapy and diagnostics", Manohara, S. R.; Hanagodimth, S. M.; Gerward, L., "Energy absorption buildup factors," Journal of Applied Clinical Medical Physics, vol. 12, No. 4, Fall 2011, May 31, 2011.

Menei, Philippe et al., "Local and Sustained Delivery of 5-Fluorouracil From Biodegradable Microspheres for the Radiosensitization of Malignant Giloma: A Randomized Phase II Trial", Neurosurgery, vol. 56, No. 2, Feb. 1, 2005, pp. 242-248.

Salem, Riad et al., "YTTRIUM-90 Microsphered for the Treatment of Hepatocellular Carcinoma: A Review", International Journal of Radiation Oncology, Biology, Physics, vol. 66, No. 2, Oct. 2006, pp. S83-S88.

Siegel, Jeffry A. et al., "Absorbed Fractions for Electrons and Beta Particles in Spheres of Various Sizes", Journal of Nuclear Medicine, vol. 35, Jan. 1994, pp. 152-156.

Stabin, Michael G. et al., "Olinda/EXM: The Second-Generation Personal Computer Software for Internal Dose Assessment in Nuclear Medicine", Journal of Nuclear Medicine, vol. 46, No. 6, Jun. 2005. pp. 1023-1027.

Stabin, Michael G. et al., "Re-Evaluation of Absorbed Fractions for Photons and Electrons in Spheres of Various Sizes", Journal of Nuclear Medicine, vol. 41, No. 1, Jan. 2000, pp. 149-160.

Storm, Ellery et al., "Photon Cross Sections From 1 KEV to 100 MEV for Elements $Z = 1$ to $Z = 100$*", Atomic Data and Nuclear Data Tables, vol. 7, No. 6, Jun. 1970, pp. 565-681.

Strigari, Lidia et al., "Efficacy and Toxicity Related to Treatment of Hepatocellular Carcinoma With 90Y-SIR Spheres: Radiobiologic Considerations", Journal of Nuclear Medicine, vol. 51, No. 9, Sep. 2010, pp. 1377-1385.

Tian, Jia-He et al., "Ultrasound-Guided Internal Radiotherapy Using YTTRIUM-90-GLASS Microspheres for Liver Malignancies", Journal of Nuclear Medicine, vol. 37, No. 6, Jun. 1996.

Villanueva, Augusto , The New England Journal of Medicine, vol. 380, Apr. 11, 2019, pp. 1450-1462.

Wallace, , "A Tissue Sealant Base on Reactive Multifuncitonal Polyethylene Glycol", J. Biomed Mater Res (Appl Biomater), 58, p. 545-555, 2601.

Wang, Eric A. et al., "Treatment Options for Unresectable HCC With a Focus on SIRT With YTTRIUM-90 Resin Microspheres", The international Journal of Clinical Practice, vol. 71, No. 11, May 2017.

Wrenn, Eric A. et al., Comparison of Flow Dynamics of Peripherally and Centrally Inserted Intravenous Catheters Using a Rapid Infucion System (Termacor 1200), AANA Journal, vol. 85, No. 4, Aug. 2017.

International Search Report and Written Opinion dated Mar. 25, 2021 for PCT Application No. PCT/IB2020/060247, 16 pages.

* cited by examiner

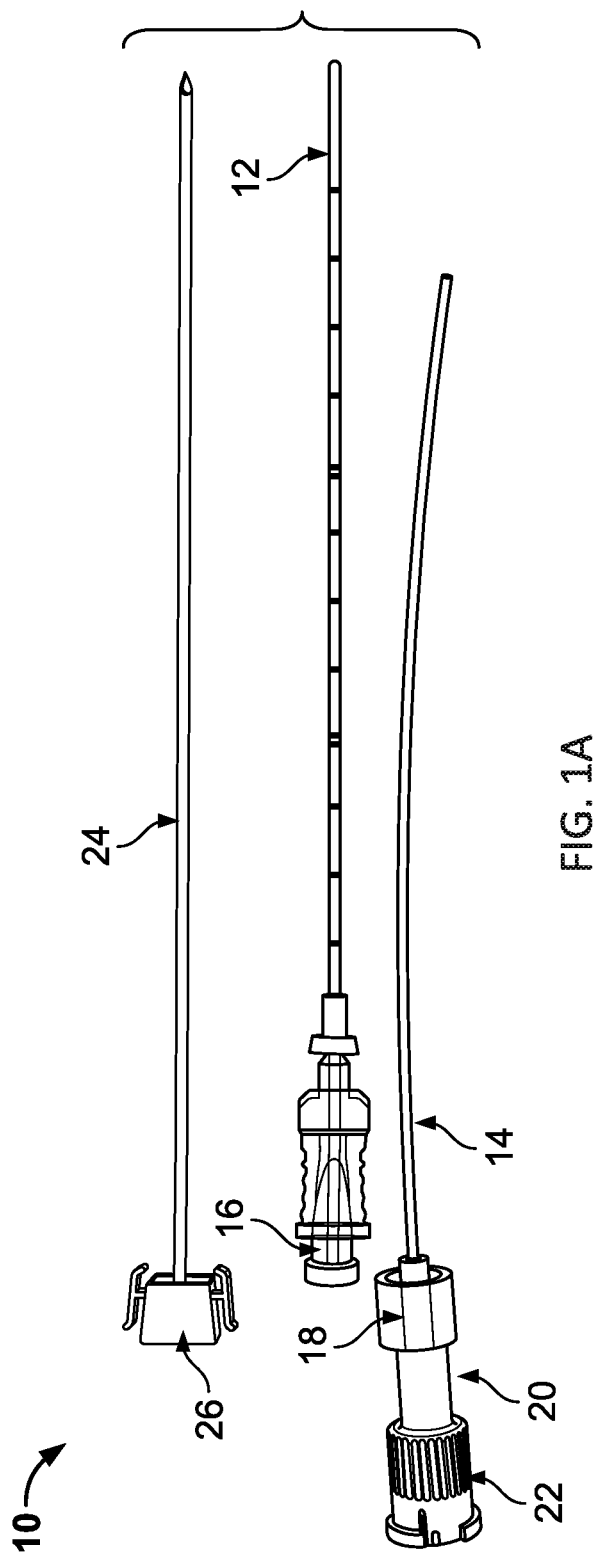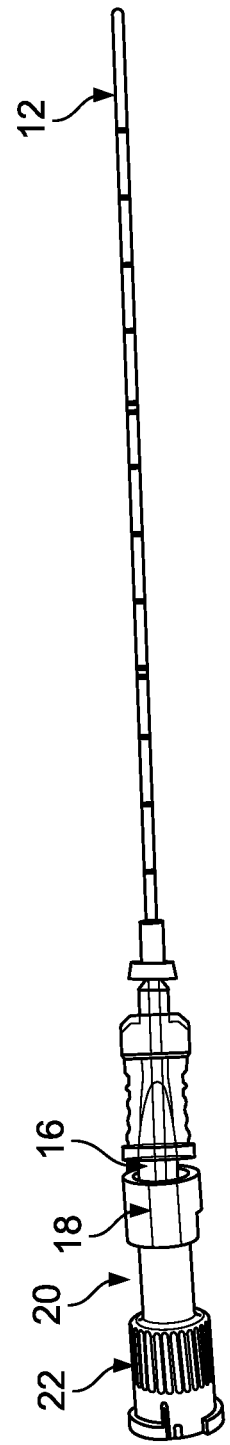
FIG. 1A
FIG. 1B

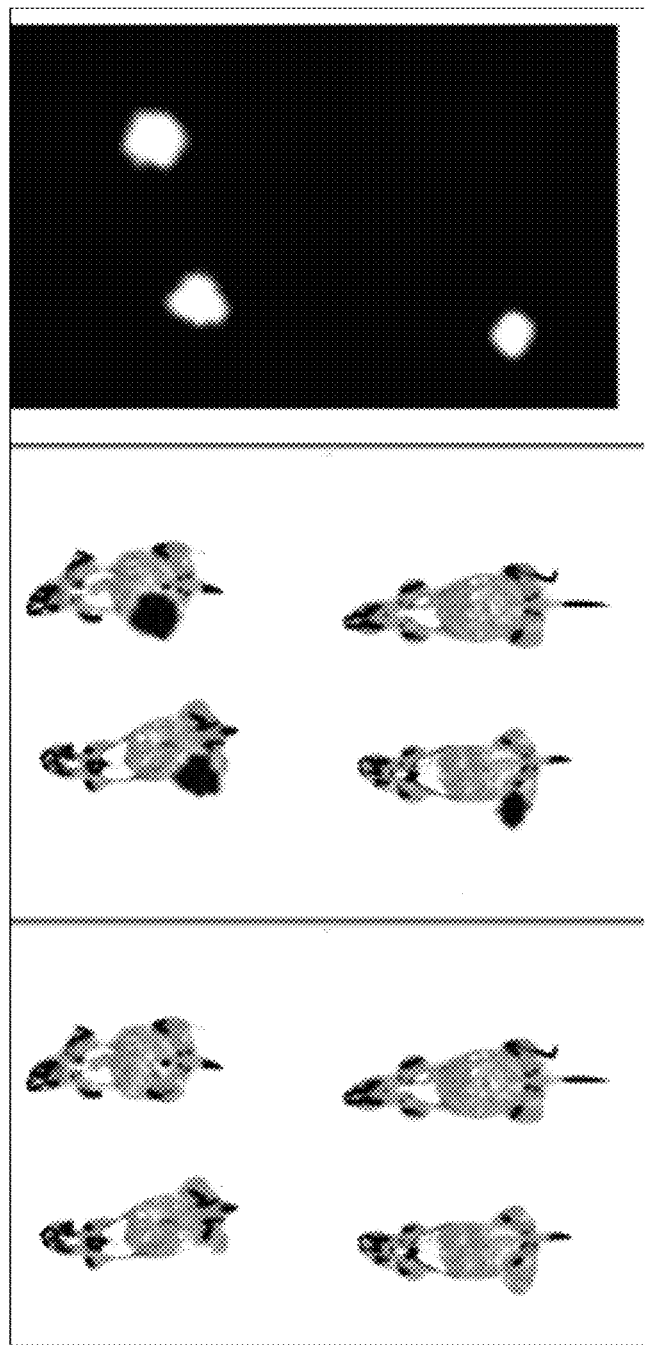

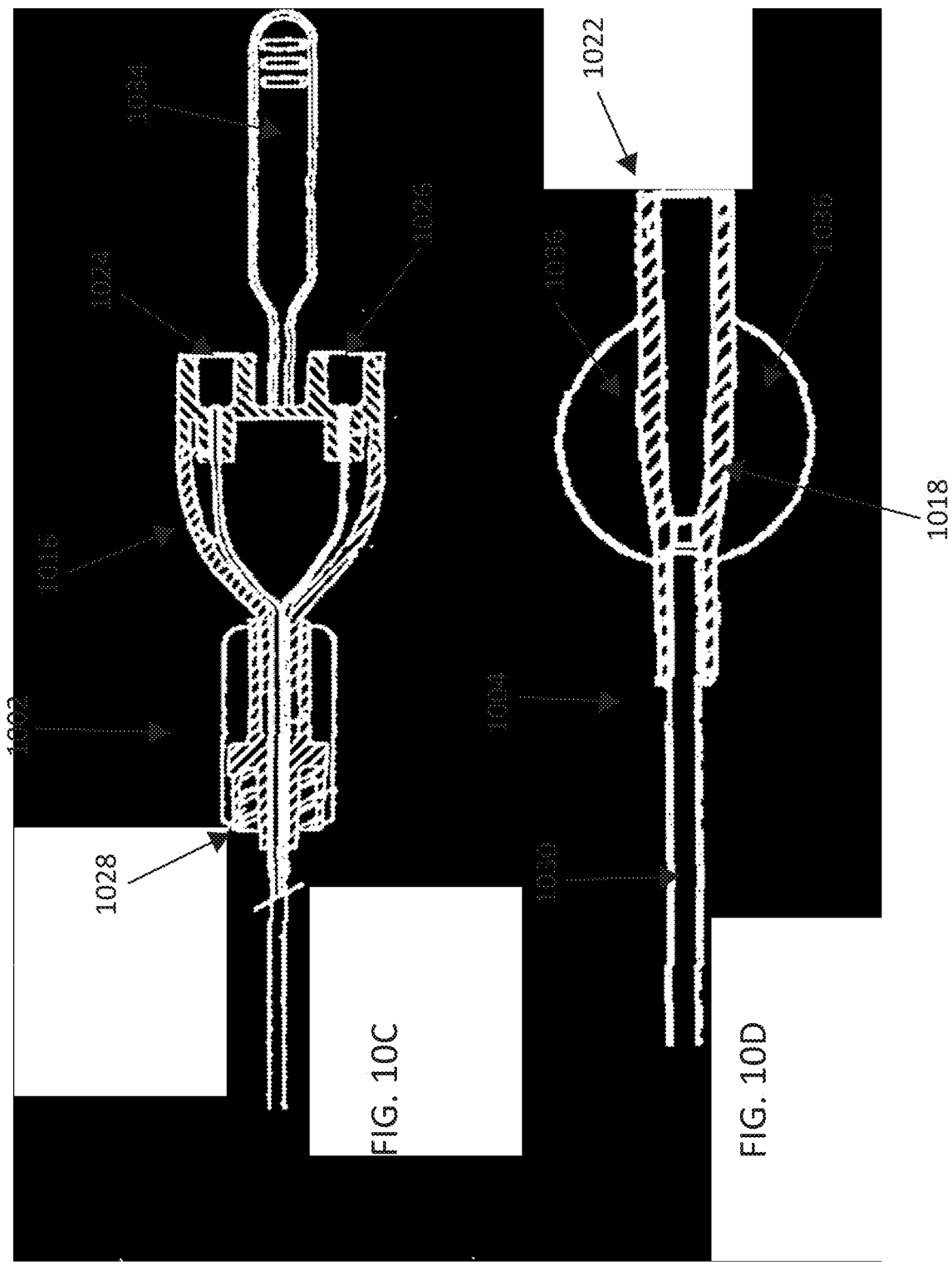

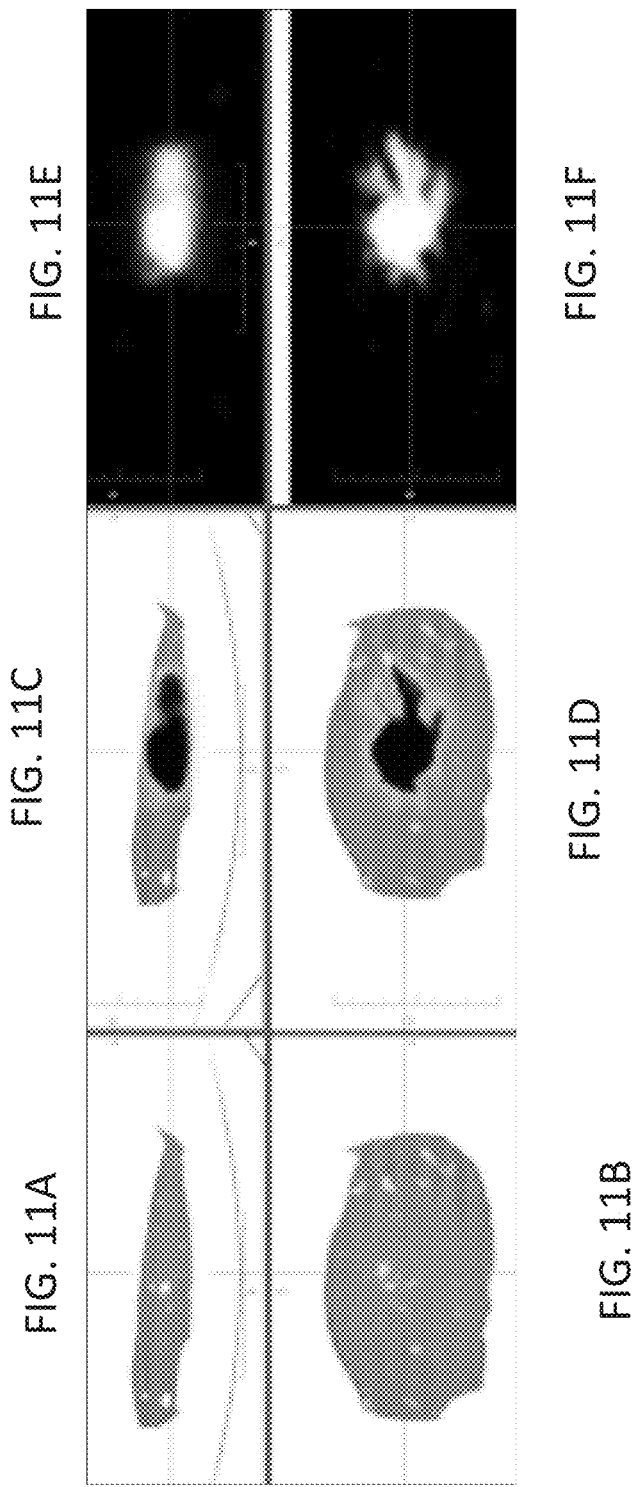

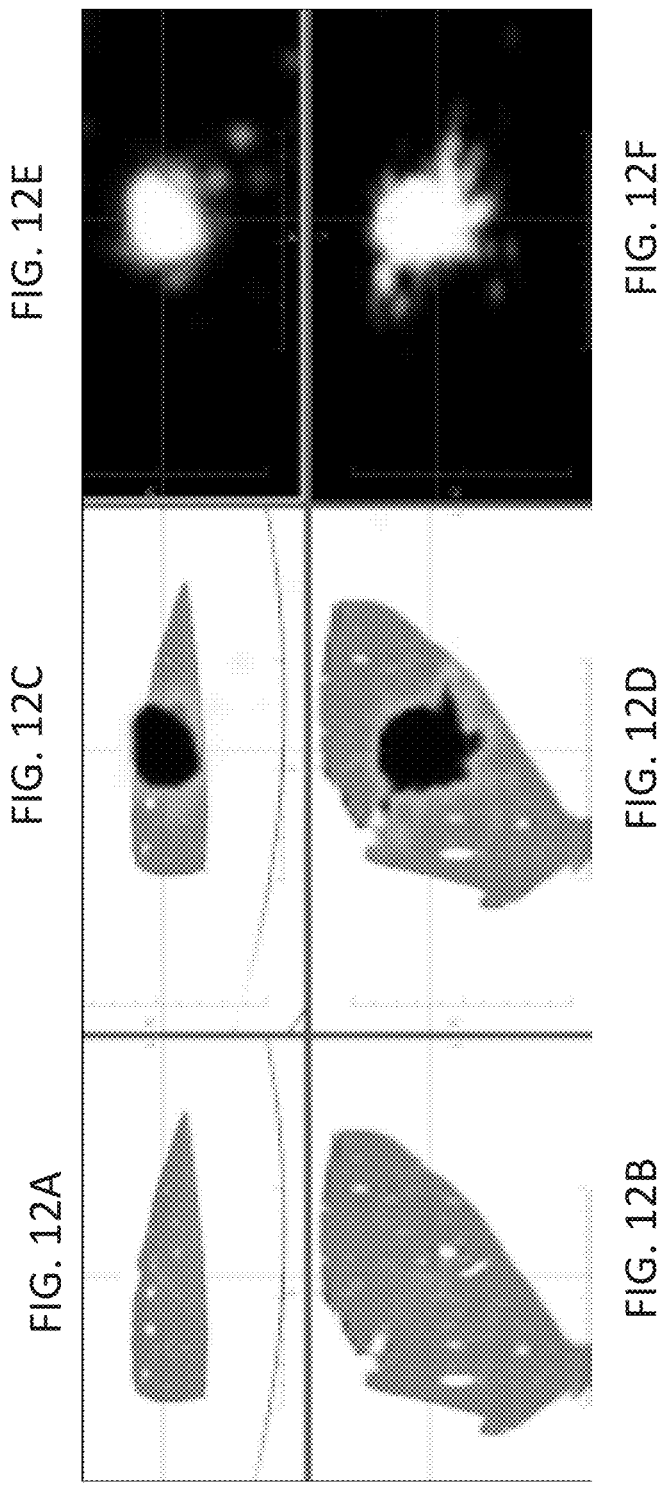

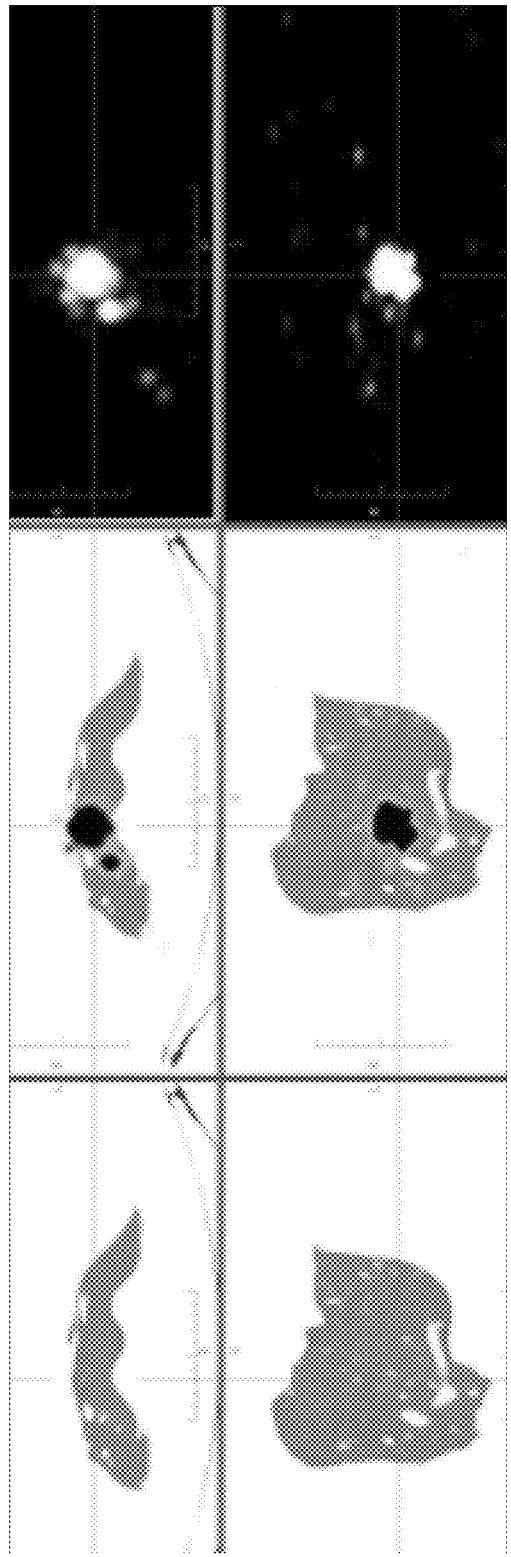

COMPOSITIONS, DEVICES AND KITS FOR SELECTIVE INTERNAL RADIATION THERAPY

RELATED APPLICATIONS

This application claims priority benefit to U.S. Provisional Application Ser. No. 63/005,172, filed Apr. 3, 2020, and to U.S. Provisional Application No. 62/929,692, filed Nov. 1, 2019, which are hereby incorporated by reference in their entirety. This application is also related to PCT Application No. PCT/IT2010/000241, filed on May 31, 2010, and to PCT Application No. PCT/IT2011/000354, filed on Oct. 21, 2011, which are hereby incorporated by reference in their entirety.

BACKGROUND

The technologies and methods relate generally to radiation therapeutics, and more specifically to compositions, devices and methods for the use of compositions comprising a carrier matrix and radiotherapeutic particles for the treatment of various oncologic and proliferative diseases, including but not limited to breast cancer and liver cancer.

Ductal Carcinoma In-Situ (DCIS), or Stage 0 breast cancer, is a biologically and clinically heterogeneous disease with a natural history influenced by both tumor- and host-related factors. Consequently, DCIS treatment after breast conserving surgery (BCS) remains controversial. It has been estimated that nine patients have to be treated to prevent one local recurrence, but some trials have shown that use of intraoperative radiotherapy (IORT) in some selected groups of low-risk early breast cancer patients result in acceptable outcomes and could therefore serve as an alternative to conventional whole-breast irradiation.

External-beam radiotherapy of the breast after BCS reduces the local breast tumor recurrence rate from 25-30% to less than 10% at 10 years. However, it is still a problem to find the optimal therapy modality for the remaining 10% of breast cancer patients presenting with a tumor recurrence years after BCS and External-beam radiotherapy (EBRT). The normal tissue tolerance does not allow, even after years, a second full-dose course of radiotherapy to the entire breast after a second BCS. Especially for patients with small, localized recurrences, in whom a local excision would technically be possible, mastectomy is generally preferred over BCS for fear of worse outcome due to omission of radiotherapy. Until the 1980s, mastectomy was the reference treatment for DCIS patients, with an approximate 98% rate of local control. Based on not only the disease extension and/or multi-centricity, but also in consideration of the patient's preferences, mastectomy continues to be performed after 2000 in at least one third of DCIS cases. Recent US data in early breast cancer (stage I and II) has shown that, due to poor access to radiation therapy and low patient compliance to treatment, up to 60% of patients may not receive any radiation therapy, and thus mastectomy is still used.

However, with increasing advances in diagnostic modalities and regular follow-up visits, recurrent breast tumors are often diagnosed at a very small tumor size. Furthermore, the most common and survival-limiting problem for these patients is usually not the local situation within the breast, but the increased risk of developing distant metastases. Finally, more than 90% of all ipsilateral breast tumor recurrences occur near the index tumor. A novel option is to treat these patients after re-resection of the recurrent tumor with partial breast irradiation. This approach is based on the hypothesis that re-irradiation to a limited volume will be effective and result in an acceptable frequency of side effects. IORT is one option to deliver high doses to a restricted area at risk, i.e. the adjacent tissue to the tumor cavity after tumor resection. IORT can be delivered with dedicated linear accelerators in the operation room or novel mobile devices using electrons or low-energy x-rays.

IORT, in which postoperative whole-breast irradiation is substituted for one session of radiotherapy with the same equivalent dose during surgery, allows treatment to be completed on the same day. Recent trials such as electron intraoperative radiotherapy versus external radiotherapy for early breast cancer (ELIOT trial) and targeted intraoperative radiotherapy versus whole breast radiotherapy for breast cancer (TARGIT-A trial) have demonstrated that IORT in some selected groups of low-risk early breast cancer patients results in acceptable outcomes and could, therefore, serve as an alternative to conventional WBRT.

In the ELIOT trial, 1305 patients were randomized (654 to external radiotherapy and 651 to intraoperative radiotherapy) with a follow up of 5-8 years. Results from this trial showed that local recurrence in the intraoperative radiotherapy group was lower than that achieved after mastectomy in a previous study (the Milan I trial). The TARGIT-A trial was a randomized, non-inferiority trial that compared risk-adapted radiotherapy using single-dose targeted intraoperative radiotherapy (TARGIT) versus fractionated EBRT for breast cancer. The results at 5 years of 3451 patients (1721 patients were randomized to TARGIT and 1730 to EBRT) demonstrated that TARGIT concurrent with lumpectomy within a risk-adapted approach should be considered as an option for eligible patients with breast cancer. This trial showed non-inferiority regarding local control after intraoperative radiotherapy (IORT) with 20 Gy which was followed by whole breast radiotherapy (WBRT) in patients with risk factors only in comparison to standard WBRT (50-56 Gy) after breast-conserving surgery in selected patients. The meta-analysis of Vaidya et al. showed that in women with breast cancer, there is a small but definite reduction in mortality when partial breast irradiation (PBI) is given instead of whole breast irradiation (WBI). On the basis of 2 statistical models used by Vaidya et al., the absolute difference in non-breast cancer mortality was 1.1% to 1.3% and was statistically significant (P=0.023 or P=0.011). The absolute difference in overall mortality was likely to be between 1.0% and 1.3%. The low P values of P=0.15 or P=0.05 indicated the improbability of observing this difference if there was no real difference between PBI and WBI. Given that the total mortality was only 4.9% (207 of 4231), in relative terms, this was a 25% reduced mortality with PBI; thus it would also be clinically significant.

Hepatocellular carcinoma (HCC) is the most common type of primary liver cancer in adults, and is the most common cause of death in people with cirrhosis. It occurs in the setting of chronic liver inflammation, and is most closely linked to chronic viral hepatitis infection (hepatitis B or C) or exposure to toxins such as alcohol or aflatoxin. Certain diseases, such as hemochromatosis and alpha 1-antitrypsin deficiency markedly increase the risk of developing HCC, while metabolic syndrome and non-alcoholic steato-hepatitis are increasingly recognized as risk factors for HCC. As with any cancer, the treatment and prognosis of HCC vary depending on the specifics of tumor histology, size, local/distant spread, and overall health. Outcomes are significantly improved if treatment is initiated earlier in the disease process. Subjects with early stage HCC are normally offered three types of therapy: (1) orthotopic liver transplantation, in selected cases; (2) surgical resection of the affected hepatic segment; (3) loco-regional therapy, which include percutaneous or catheter-based therapies. Most current forms of percutaneous ablation have been shown to be as effective as surgical resection. They are also less invasive and demanding for the patient and for the medical facilities. It is difficult, however, in many cases to achieve a negative "surgical" margin, for a number of reasons, including the size of the lesion and its anatomical location. This means that surrounding areas to the tumoral lesion bearing satellite micrometastases can be missed and not necrotized. This, in turn, makes recurrence of the tumor a clear possibility. The currently reported overall success rate is in fact 70-80% for thermal ablation (e.g. radio frequency, laser, microwave), 70-80% for cryo-ablation, and 60-80% for ethanol injection (data Mayo Clinic 2017). Therefore, at least 20% of tumoral lesions will be followed by local recurrence.

Percutaneous local ablation (PLA) techniques are currently considered as the best treatment option for patients with early-stage HCC who are not candidates for surgical resection. They are safe, minimally invasive, efficacious and cost-effective. Radiofrequency ablation is considered as the first-line treatment in some centers, though most of the guidelines recommend it for small HCCs, where surgical resection is not feasible. PLA is a relatively simple minimally invasive procedure that selectively targets the tumor and an additional intentional margin of healthy tissue from 0.5 to 1.0 cm. This additional margin helps to achieve complete ablation (A0) similar to R0 resection after surgery. Moreover, hepatic resection is not an ideal treatment for very small sized cases of HCC because of the potential loss of liver function and the high risk of complications. In this regard, an international panel of ablation experts recently published a position paper on PLA of colorectal cancer liver metastases. A strong consensus level was achieved for the treatment of nodules up to 5 cm when well located (with easy access). Likewise, a strong level of consensus was achieved for combination strategies with respect to systemic treatments alone. The panel also agreed in considering PLA as potentially curative in respectable patients when used as a first-line treatment. The clinical effectiveness of selective internal radiation therapy (SIRT, also known as Trans Arterial Radio Embolization, TARE) using $^{131}$I-radiolabelled lipiodol was first demonstrated in 1994 based on a randomized study in patients with portal vein thrombosis. In particular, one retrospective study has shown that glass microspheres are able to achieve a significantly improved rate of down-staging compared to chemoembolization, with significantly fewer side effects in patients with stage T3 HCC, while another study has shown that progression-free survival is significantly improved in patients with HCC who were treated with locoregional therapies, such as chemoembolization and radioembolization. $^{90}$Y resin microspheres (SIR-SPHERES®—Sirtex Medical) is a CE-marked brachytherapy device, recommended through the National Comprehensive Cancer Network and European Society for Medical Oncology guidelines for the treatment of chemo-refractory colorectal cancer liver metastases in selected patients with liver-only or liver-dominant disease.

BRIEF SUMMARY

Because of the clinical experience accumulated in over 15 years of treatments based on trans-arterial infusion of $^{90}$Y-coated microspheres, it is believed that the administration of the appropriate activity of $^{90}$Y should reduce the chances of local recurrence, which occurs in the vast majority of cases in the surgical bed. Exemplary devices, kits and methods are disclosed using a combined $^{90}$Y-matrix and delivery system to treat patients with DCIS or other forms of early breast cancer, and to assess effectiveness and safety of radioactivity-based ablation of surgical margins following DCIS resection. Exemplary devices, kits and methods are used to treat hepatocellular carcinoma, including but not limited to injection or administration into a lesion, or to a treatment site following resection of a lesion. The delivery kit comprising a coaxial dual-lumen catheter used to provide direct, imaging-guided intra-tumoral injection of the $^{90}$Y microsphere-matrix combination.

In some variations, the patients selected for treatment may comprise patients with Stage 0 breast cancer (e.g., DCIS) who are treated with intra-tumoral or tumor bed injection. In other variations, the patients may have Stage I or II breast cancer who are treated by intra-tumoral injection or treatment of the tumor bed post-lumpectomy. This may also include Stage IIA and/or IIB patients and include intra-tumoral injection into one or more axillary lymph nodes.

The $^{90}$Y-matrix and delivery system is believed to allow for an effective and safe radio-ablation of surgical margins following DCIS resection, thus offering a new procedure in the armamentarium of loco-regional treatments for early breast cancer, compared to $^{90}$Y microsphere treatment alone.

In other variations, the patient selected for treatment may comprise patients with hepatocellular carcinoma, as with metastatic liver tumors, whether respectable or unrespectable. Patients with HCC may include those with T1, T1a, T1b, T2, T3, or T4 primary tumors, as well as those with or without or unknown regional lymph nodes metastases involvement and/or distal metastases, including Stage IA, IB, II, IIA, IIIB, IVA and IVB HCC patients. Treatment may include intra-tumoral administration or post-resection administration to the tumor bed in the liver, lymph node or distal metastasis site.

In one example, the $^{90}$Y-matrix system is a combination of BIOGLUE® (CryoLife; Kennesaw, Ga.), a mixture of bovine serum albumin and glutaraldehyde in a 4:1 ratio, and SIR-SPHERES® microspheres (Sirtex Medical; North Sydney, AU) coated with $^{90}$Y, a pure β emitter isotope. The mixture is delivered using a dual-chamber syringe. Preloaded microspheres with $^{90}$Y are then blended with glue components and used to perform radio-ablation of the surgical margins of the treatment site.

In various examples, systems, kits and methods for preparing an injection system and/or treating target lesions with a selective internal radiation therapy includes a double-barrel syringe loaded with a two-component tissue glue and radioisotope loaded microspheres are provided. The microspheres are loaded into the syringe based on the size of the target location and are injected with a needle or dual-lumen catheter. Dosing regimens for treating breast cancer lesions up to 130 mm in diameter and hepatocellular carcinoma lesions up to 50 mm are included.

In one example, a method of preparing an implantable radiotherapeutic is provided, comprising mixing radioisotope microspheres with a suspension medium, wherein the microspheres are located in the suspension medium contained in a first container, determining a transfer volume of the mixed microspheres based on a target size, loading an injection system with the transfer volume, the injection system comprising a first compartment with a first cross-sectional area and a second compartment with a second cross-sectional area, the first and second cross-sectional areas having a ratio of XY, transferring a first proportion of the transfer volume to the first compartment, and transferring a second proportion of the transfer volume to the second compartment, wherein the first proportion and the second proportion have a proportion ratio of XY. The radioactive microspheres may be provided in a settled state in a container within a pre-determined volume of the suspension medium. The method may further comprise removing a removal volume of the suspension medium from the pre-determined volume of the suspension medium before mixing the radioactive microspheres with the suspension medium. The removal volume may be 2 mL and the pre-determined volume of suspension medium may be 5 mL. The first proportion of the transfer volume may be X/(X+Y) of the transfer volume and wherein the second proportion of the transfer volume is Y/(X+Y) of the transfer volume. The injection system may be a double-barrel syringe, comprising a first barrel with the first compartment and a second barrel with the second compartment. The ratio of the first cross-sectional area to the second cross-sectional area may be 4:1. The first barrel may be preloaded with a first substance and the second barrel may be preloaded with a second substance. The total volume of the first and second substances may be 2 mL. The total volume of the first and second substances may be 5 mL. The transfer volume may comprise an activity level in the range of 0.1 MBq to 250 MBq. The activity level may be in the range of 0.3 MBq to 220 MBq, and the transfer volume may be in a range of 0.3 µL to 220 µL. The target size may be in a range of 1 mm to 50 mm in average diameter. The transfer volume may comprise an activity level in the range of 10 MBq to 200 MBq. The activity level may be in the range of 20 MBq to 150 MBq, and the transfer volume may be in a range of 100 µL to 750 µL. The target size may be in a range of 40 mm to 130 mm in average diameter. The first substance may comprise an albumin and the second substance may comprise glutaraldehyde. The radioactive microspheres may comprise an activity level of 3 GBq or less and the pre-determined volume of suspension medium may be 5 mL or less. The mixing of the radioisotope microspheres and the loading of the injection system may be both performed by a shielded transfer syringe with a needle with a length in the range of 50 mm to 100 mm. The method may further comprise verifying an activity level of the transfer volume of the radioisotope microspheres by determining an activity level of the container after loading the injection system, or determining an activity level of the injection system after loading the injection system. The method may further comprise placing the loaded injection system into a radioprotective vessel. The method may further comprise disposing of a portion each of the first and second substances in a volume ratio of XY and wherein the total of the two portions is equal to the transfer volume of the mixed microspheres.

In another example, a method of treating a patient is provided, comprising delivering a treatment volume of mixed radioactive microspheres to a lesion, wherein the lesion includes the tumor lesion and/or the post-surgical lesion site, using a double barrel syringe with a mixing tip, wherein the first barrel of the syringe contains bovine serum albumin and the radioactive isotope, and the second barrel of the syringe contains glutaraldehyde and the radioactive isotope. The lesion may be an early breast cancer lesion, including a ductal carcinoma in situ lesion (stage 0). The nominal dose at the lesion may be at least 18 to 20 Gy. The method may further comprise loading each barrel of the double barrel syringe with different amounts of the radioactive microspheres based on a size of the lesion. The double-barrel syringe, prior to injection, may comprise a total injectable volume between 2.1 and 2.5 mL and an activity of 20 to 90 MBq. The treatment location may have an average radius of 20 to 45 mm. The treatment volume injected may be the total injectable volume. The double-barrel syringe, prior to injection, may comprise a total injectable volume between 5.1 and 6 mL and an activity of 90 to 150 MBq. The ductal carcinoma in situ lesion may have an average radius of 45 to 65 mm. The treatment volume injected may be equal to the total injectable volume. The lesion may be a hepatocellular carcinoma lesion. The dose at the lesion may be at least 150 Gy. The double-barrel syringe, prior to injection, may comprise a total injectable volume between 2.0001 and 2.05 mL and an activity of 0.3 to 30 MBq. The lesion may have an average radius of 0.5 to 25 mm. The treatment volume delivered may be the total injectable volume. The barrel syringe, prior to injection, may comprise a total injectable volume between 5.01 and 5.5 mL and an activity of 20 to 250 MBq. The ductal carcinoma in situ lesion or resection site may have an average radius of 25 to 50 mm. The treatment volume injected may be equal to the total injectable volume. The concentration of bovine serum albumin may be between 30 and 60 percent by weight. The concentration of glutaraldehyde may be between 5 and 15 percent by weight.

In still another example, a method of treating a patient is provided, comprising removing from a sealed sterile package a double barrel syringe, wherein each barrel may be pre-loaded with a different volume of a different substance, the total volume of the different substances may be 5 mL or less, determining a transfer volume of a radioactive microsphere suspension based on a lesion size, and transferring different size portions of the transfer volume of the radioactive suspension to each barrel of the double barrel syringe. The total volume of the different substances may be 5 mL or less. The transfer volume of the radioactive microsphere suspension may be less than 300 µL and the activity level may be less than 300 MBq and the lesion may be between 25 mm and 50 mm in average diameter. The method may further comprise treating the lesion with a total volume of the different substances and radioactive microsphere suspension between 5.01 and 5.3 mL. The total volume of the different substances may be 2 mL or less. The transfer volume of the radioactive microsphere suspension may be less than 30 µL and the activity level may be less than 30 MBq and the lesion may be between 0.3 mm and 30 mm in average diameter. The method may further comprise treating the lesion with a total volume of the different substances and radioactive microsphere suspension that may be greater than 2 mL and less than 2.1 mL.

In another embodiment, a lesion treatment system is provided, comprising a double barrel syringe comprising a first barrel with a first sliding seal and a first cross sectional area, and containing a first glue component, a second barrel with a second sliding seal and a second cross sectional area and containing a second glue component, a driver configured to dispense a fixed proportion of the first and the second glue components from the first and second barrels, a radioisotope loaded in at least one of the first and second barrels, a plurality of indicia of lesion sizes provided on the double barrel syringe, comprising uniform size intervals across a size range that are spatially located at non-uniform intervals along the double barrel syringe. The plurality of indicia of lesion sizes include lesion diameters in the range of 40 mm to 130 mm. The driver may be an interconnected double plunger attached to the first and second sliding seals and may be configured to move the first and second sliding seals at equal longitudinal distances. The first and second cross sectional areas may be different. The first glue component may be bovine serum albumin and the second glue component may be glutaraldehyde. The bovine serum albumin may be 45% by weight and the glutaraldehyde may be 10% by weight. The radioisotope may be $^{90}$Y with an activity level between 10 and 250 MBq. The radioisotope may be $^{90}$Y with an activity level between 10 and 100 MBq and wherein the plurality of indicia of lesion sizes may include lesion diameters in the range of 40 mm to 90 mm. The radioisotope may be $^{90}$Y with an activity level between 80 and 160 MBq and wherein the plurality of indicia of lesion sizes may include lesion diameters in the range of 90 mm to 130 mm. The radioisotope may be $^{90}$Y with an activity level between 0.1 and 50 MBq and wherein the plurality of indicia of lesion sizes may include lesion diameters in the range of 0.5 mm to 25 mm. The radioisotope may be $^{90}$Y with an activity level between 25 and 250 MBq and wherein the plurality of indicia of lesion sizes may include lesion diameters in the range of 25 mm to 50 mm.

In one embodiment, a method for treating a patient is provided, comprising determining a treatment dosage using the target activity level $A_0$ and mass of the target tissue using $D_{avg}(r) = A_0 \cdot k(r)/m$, wherein the delivered energy per unit activity $k(r)$ is based on the radius of the target tissue. In some variations, the $k(r)$ value is 49.35 (J/GBq). The target tissue radius may include one or more target tissue radii in the range of 0.5 cm to 2.0 cm. The method may further comprise loading an amount of $^{90}$Y into a two-chamber syringe, wherein the amount is based on the determined treatment dosage. The amount of $^{90}$Y may be further based on syringe size, and may be further based on syringe size and dead space associated with the syringe size. The two chambers of the syringe may each hold one component of a two-component glue or carrier composition. A first chamber of the syringe comprises albumin and a second chamber comprises glutaraldehyde. The $^{90}$Y may be loaded into both the first and the second chambers of the syringe. In other variations, the $^{90}$Y is loaded only in one of either the first or second chamber of the syringe. The method may further comprise injecting the $^{90}$Y and glue or carrier composition through a mixing tip attached to the two-chamber syringe, wherein the mixing tip comprises a shaft with a plurality of angle mixing structures. In another embodiment, a non-transitory computer-readable medium is provided, comprising a computer program product comprising one or more computer instructions to perform the determination of the treatment dosage as described above, when the computer program is run on one or more processors.

In another embodiment, a non-transitory computer-readable medium is provided, comprising one or more computer instructions, comprising determining a $^{90}$Y treatment dosage based on a fractional tumor uptake correlated to tumor size and an average $^{90}$Y tissue penetration distance of 4 mm. The computer instructions may further comprise instructions to output a first volume of $^{90}$Y to be transferred into a syringe delivery device, to output a transfer syringe size, to optionally output a first chamber of the syringe delivery device for the transfer of the first volume of $^{90}$Y, to optionally determine output of a second volume of $^{90}$Y to be transferred into the syringe delivery device and/or to optionally output a second chamber for the transfer of the second volume of $^{90}$Y. In another variation, the computer-readable medium may further comprise computer instructions to determine a target volume of a carrier composition, output the target volume of the carrier composition, and determine and output a waste volume of the carrier composition based on the transfer syringe size. Output may be provided on a display screen, and may include numerical output and/or pictorial output of a syringe with graphical indicator of the numerical output. The computer program product may perform the steps above when the computer is run on one or more processors.

In one embodiment, a method of treating breast cancer is provided, comprising determining an average tumor size of a breast cancer lesion, selecting a $^{90}$Y syringe activity level and a $^{90}$Y treatment activity level using the average tumor size, wherein the $^{90}$Y treatment activity level is 15 MBq to 20 MBq for the average tumor size corresponding to a radius in the range of 20 mm to 24 mm, 20 MBq to 25 MBq for the average tumor size corresponding to a radius in the range of 25 mm to 29 mm, 25 MBq to 35 MBq for the average tumor size corresponding to a radius in the range of 30 mm to 34 mm, 40 MBq to 50 MBq for the average tumor size corresponding to a radius in the range of 35 mm to 39 mm, 55 MBq to 65 MBq for the average tumor size corresponding to a radius in the range of 40 mm to 44 mm, 75 MBq to 85 MBq for the average tumor size corresponding to a radius in the range of 45 mm to 49 mm, 90 MBq to 100 MBq for the average tumor size corresponding to a radius in the range of 50 mm to 54 mm, loading a dual chamber syringe with the selected $^{90}$Y syringe activity level, wherein the dual chamber syringe comprises a first chamber pre-loaded with bovine serum albumin and a second chamber pre-loaded with glutaraldehyde, and injecting the selected $^{90}$Y treatment activity level at a treatment site of the breast cancer lesion using the dual chamber syringe. The $^{90}$Y syringe activity level may be 20 MBq for the average tumor size corresponding to a radius in the range of 20 mm to 24 mm, 25 MBq for the average tumor size corresponding to a radius in the range of 25 mm to 29 mm, 35 MBq for the average tumor size corresponding to a radius in the range of 30 mm to 34 mm, 50 MBq for the average tumor size corresponding to a radius in the range of 35 mm to 39 mm, 70 MBq for the average tumor size corresponding to a radius in the range of 40 mm to 44 mm, 90 MBq for the average tumor size corresponding to a radius in the range of 45 mm to 49 mm, and 110 MBq for the average tumor size corresponding to a radius in the range of 50 mm to 54 mm. The method may also further comprise adjusting a concentration of a $^{90}$Y source before withdrawing the selected 90Y syringe activity level, wherein adjusting the concentration comprises adding 5 mL of water to the $^{90}$Y source, or adjusting the concentration of the $^{90}$Y source to 3 GBq/10 mL, and withdrawing the selected 90Y syringe activity level from the $^{90}$Y source. In some further embodiments, the method may further comprise determining a volume of the $^{90}$Y syringe activity level for withdrawal based on $^{90}$Y decay and the average tumor size. The loading of the dual chamber syringe may comprise loading the $^{90}$Y syringe activity level into the first and second chambers of the dual chamber syringe in a 1:4 ratio. The method may also further comprise placing the dual chamber syringe into a first radio-protective container before loading the dual chamber syringe with the selected $^{90}$Y syringe activity level, placing a transfer syringe into a second radio-protective container, and using the transfer syringe to load the dual chamber syringe. The first and second radio-protective containers may comprise PMMA cylinders. The method may also further comprise confirming a source activity level of a $^{90}$Y source, withdrawing the $^{90}$Y syringe activity level from the $^{90}$Y source, and confirming the syringe activity level of the dual chamber syringe after loading the dual chamber syringe. In another further embodiment, the method may further comprise confirming a residual activity level of the dual chamber syringe after injecting the treatment site. The breast cancer may be ductal carcinoma in situ and/or the treatment site may be a post-resection treatment site of the breast cancer lesion.

In another example, a method of preparing a breast cancer treatment may be provided, comprising determining an average tumor size of a breast cancer lesion from an image, selecting a $^{90}$Y syringe activity level and a $^{90}$Y treatment activity level using the average tumor size, wherein the $^{90}$Y treatment activity level is 15 MBq to 20 MBq for the average tumor size corresponding to a radius in the range of 20 mm to 24 mm, 20 MBq to 25 MBq for the average tumor size corresponding to a radius in the range of 25 mm to 29 mm, 25 MBq to 35 MBq for the average tumor size corresponding to a radius in the range of 30 mm to 34 mm, 40 MBq to 50 MBq for the average tumor size corresponding to a radius in the range of 35 mm to 39 mm, 55 MBq to 65 MBq for the average tumor size corresponding to a radius in the range of 40 mm to 44 mm, 75 MBq to 85 MBq for the average tumor size corresponding to a radius in the range of 45 mm to 49 mm, 90 MBq to 100 MBq for the average tumor size corresponding to a radius in the range of 50 mm to 54 mm, and loading a dual chamber syringe with the selected $^{90}$Y syringe activity level, wherein the dual chamber syringe comprises a first chamber pre-loaded with bovine serum albumin and a second chamber pre-loaded with glutaraldehyde. The $^{90}$Y syringe activity level may be 20 MBq for the average tumor size corresponding to a radius in the range of 20 mm to 24 mm, 25 MBq for the average tumor size corresponding to a radius in the range of 25 mm to 29 mm, 35 MBq for the average tumor size corresponding to a radius in the range of 30 mm to 34 mm, 50 MBq for the average tumor size corresponding to a radius in the range of 35 mm to 39 mm, 70 MBq for the average tumor size corresponding to a radius in the range of 40 mm to 44 mm, 90 MBq for the average tumor size corresponding to a radius in the range of 45 mm to 49 mm, and 110 MBq for the average tumor size corresponding to a radius in the range of 50 mm to 54 mm. The method may further comprise adjusting a concentration of a $^{90}$Y source before withdrawing the selected $^{90}$Y syringe activity level, wherein adjusting the concentration comprises adding 5 mL of water to the $^{90}$Y source, or adjusting the concentration of the $^{90}$Y source to 3 GBq/10 mL, and withdrawing the selected $^{90}$Y syringe activity level from the $^{90}$Y source. The method may also further comprise determining a volume of the $^{90}$Y syringe activity level for withdrawal based on $^{90}$Y decay and the average tumor size. The loading of the dual chamber syringe may comprise loading the $^{90}$Y syringe activity level into the first and second chambers of the dual chamber syringe in a 1:4 ratio. The method may also further comprise placing the dual chamber syringe into a first radio-protective container before loading the dual chamber syringe with the selected $^{90}$Y syringe activity level, placing a transfer syringe into a second radio-protective container, and using the transfer syringe to load the dual chamber syringe. The first and second radio-protective containers may comprise PMMA cylinders. The method may further comprise confirming a source activity level of a $^{90}$Y source, withdrawing the $^{90}$Y syringe activity level from the $^{90}$Y source, and confirming the syringe activity level of the dual chamber syringe after loading the dual chamber syringe. The breast cancer may be ductal carcinoma in situ.

In still another embodiment, a kit for performing radiotherapeutic procedures is provided. The kit may comprise two sterile 1 mL syringes, two Luer locks, two 22G needles, two sterile 20G×70 mm needles and two PMMA cylinders, each configured to retain a 1 mL or 2 mL syringe. In other variations, the two 20G×70 mm needles may be substituted with any needles that are 20G or larger in size and comprise a length of at least 50 mm, and/or the PMMA cylinders may comprise a non-circular cross-sectional shape, e.g. square or polygon shape, and may comprise a metal or polymeric material other than PMMA.

BRIEF DESCRIPTION OF THE DRAWINGS

FIG. 1A is an exemplary component view of the stylet, introducer and catheter that may be used with exemplary procedures; FIG. 1B depicts the catheter and introducer of FIG. 1A wherein the catheter is inserted into the introducer and their hubs are locked together;

FIG. 8A are transverse CT views of a mouse with a thigh tumor; FIG. 8B are composite transverse CT/PET/SPECT views of the mouse in FIG. 8A depicting tumor activity; FIG. 8C are the PET/SPECT image components from FIG. 8B.

FIG. 10C is a longitudinal cross-sectional view of the proximal end of the catheter in FIGS. 10A and 10B; FIG. 10D is a longitudinal cross-sectional view of the proximal end of the introducer in FIGS. 10A and 10B;

FIGS. 11A and 11B are side and superior cross-sectional CT views of an explanted tumor, respectively; FIGS. 11C and 11D are composite side and superior cross-sectional CT/PET/SPECT views of the explanted tumor in FIGS. 11A and 11B, respectively; FIGS. 11E and 11F are the PET/SPECT image components from FIGS. 11C and 11D, respectively;

FIGS. 12A and 12B are side and superior cross-sectional CT views of another explanted tumor, respectively; FIGS. 12C and 12D are composite side and superior cross-sectional CT/PET/SPECT views of the explanted tumor in FIGS. 12A and 12B, respectively; FIGS. 12E and 12F are the PET/SPECT image components from FIGS. 12C and 12D, respectively;

FIGS. 13A and 13B are side and superior cross-sectional CT views of another explanted tumor, respectively; FIGS. 13C and 13D are composite side and superior cross-sectional CT/PET/SPECT views of the explanted tumor in FIGS. 13A and 13B, respectively; FIGS. 13E and 13F are the PET/SPECT image components from FIGS. 13C and 13D, respectively;

DETAILED DESCRIPTION

Figure 2A:
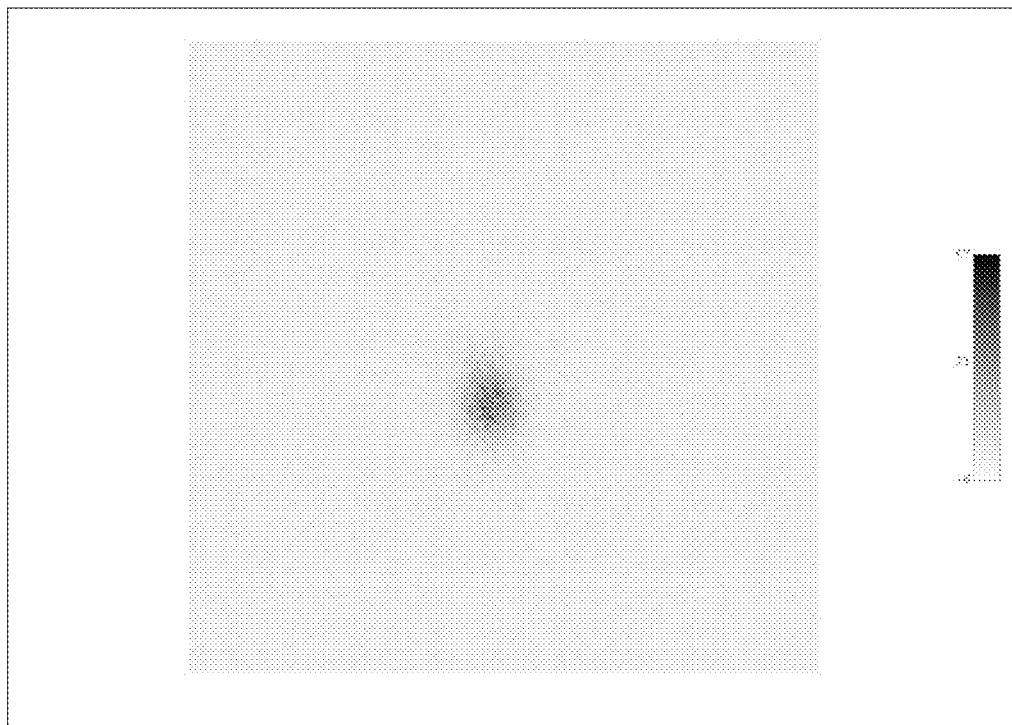
FIGS. 2A and 2B are anteroposterior and posteroanterior views of a syringe cylinder loaded with $^{90}$Y microspheres in a BIOGLUE® carrier.

In one embodiment, a kit for performing direct injection radiotherapy is provided. The kit comprises a venting needle, a radio-shielded syringe, and an elongate needle of at least 50 mm to 100 mm in length. These components of the kit may be used to transfer radioisotope microparticles from their transport vessel to the matrix-containing syringe. The venting syringe may be inserted through the seal of the transport vessel to break or release any vacuum that may form in the transport vessel during the transfer process, and may be a 22G, 25G, 28G, 30G, 31G or 32G hypodermic needle. The venting needle may be optionally left in place during the remainder of the procedure, or removed immediately after insertion. The elongate needle is attached to the radio-shielded syringe at either the point-of-use or point-of-manufacture and is used to remove liquid media from the transport vessel.

In some variations, the kit may comprise an introducer, a dual-lumen catheter, and a needle. The kit may optionally further comprise a radio-shielded syringe, an elongate needle of at least 50 mm to 100 mm in length, and/or a venting needle as described above. In still other variations, the kit may further comprise a glue or matrix, and/or a radioisotope source, but in other examples, the glue/matrix and/or the radioisotope are sourced separately from the kit. In these variations, the kit may further comprise adapters configured to couple the kit components to a third party injector system selected by the user, or one or more of the kit components may be configured to couple to a third party glue/matrix syringe or injection system.

The $^{90}$Y source may comprise a vial of radiotherapeutic microspheres. The vial may be a clear unshielded glass vial, that may be removably provided in a lead lined pot or other container. A vial containing 3 GBq of $^{90}$Y in 5 mL of water or other suspension liquid are provided. The $^{90}$Y is a pure, high energy (maximum energy 2.227 MeV, mean 0.93 MeV), β-emitter isotope. Its half-life is 64.1 hours; the maximum penetration in tissues is 11 mm with a mean of 2.5 mm. The vial may be provided in a lead pot or other shielded container. The vial or other packaging may contain calibration or validation data, and/or a code to access online regarding the same, so that the treating healthcare provider can compensate for any radioactive decay that has occurred since the initial manufacture and validation. In other examples, however, the amount of microsphere activity may be different, e.g. 100 MBq, 200, MBq, 300 MBq, 400 MBq, 500 MBq, 600 MBq, 700 MBq, 800 MBq, 900 MBq, 1 GBq, 2 GBq, 3 GBq, 4 GBq, 5 GBq, or a range of between any two of these activity levels, and the number of microspheres per vial may be different, e.g. 10 million, 20 million, 30 million, 40 million, 50 million, 60 million, 70 million, 80 million, 90 million, 100 million, or a range between any two of these microsphere counts. In one specific example, the $^{90}$Y source may comprise 2.4 GBq particles in 3 mL of water.

In one particular embodiment, SIR-SPHERES® may be used for the source of the $^{90}$Y or $^{90}$Y particles. SIR-SPHERES® is a solution of biocompatible microspheres containing about 40 to about 80 million microspheres in 5 mL water. The microspheres comprise a non-biodegrading resin with diameters between 20 and 60 microns (μm), containing $^{90}$Y, a pure, high energy (maximum energy 2.227 MeV, mean 0.93 MeV), β-emitter isotope. The half-life is 64.1 hours; the maximum penetration in tissues is 11 mm with a mean of 2.5 mm. SIR-SPHERES® microspheres are a permanent implant (e.g. the microspheres are not metabolized or excreted after implantation). 94% of total radiation is locally delivered in 11 days. SIR-SPHERES® microspheres are provided by the manufacturer in a shielded (6.4 mm of thickness) vial with water for the administration. Each vial contains approximatively 3 GBq of $^{90}$Y in a final volume of 5 mL, or alternatively 2.4 GBq of $^{90}$Y in a final volume of 3 mL, or in a range from 2-3 GBq in a final volume of 2-5 mL, or 2-3 mL; the number of microspheres ranges between 40-80×10$^6$/vial, or 32-64×10$^6$/vial. The SIR-SPHERES® vial should be stored at 15-25° C.

The potential adverse events associated with the use of SIR-SPHERES® include:
 fever
 transient decrease of hemoglobin
 mild to moderate abnormality of liver function tests (e.g. mild increase in ALT, AST, alkaline phosphatase, and/or bilirubin)
 abdominal pain
 nausea
 vomiting
 diarrhea As described previously, the kit may further optionally comprise a glue or matrix source, but the glue or matrix source may also be separately sourced for use with the kit.

In one particular example, BIOGLUE® may be used for the glue component of the $^{90}$Y-glue matrix composition. BIOGLUE® is an admixture of bovine serum albumin (BSA; 45% weight/volume in sterile water for injection) and glutaraldehyde (10% weight/volume in sterile water for injection) in a 4:1 ratio. The bovine serum is purified by heat precipitation, chromatography, and gamma-irradiation to eradicate possible transmissible diseases. Glutaraldehyde exposure causes the lysine molecules of the bovine serum albumin, extracellular matrix proteins, and cell surfaces to bind to each other, creating a strong covalent bond. The reaction is spontaneous and independent of the coagulation status of the patient. The glue begins to polymerize within 20 to 30 seconds and reaches maximal strength in approximately 2 minutes, resulting in a solid implant. The degradation process takes approximately 2 years, and the implant is then replaced with fibrotic granulation tissue. The adhesive solutions (BSA and glutaraldehyde in a 4:1 ratio) are mixed in the applicator tip of the dual-chamber syringe where cross-linking begins. BIOGLUE® is not believed to be a true hemostatic agent because it does not accelerate the clotting process in blood. However, BIOGLUE® acts as a sealant after it completely hardens, by tamponating parenchymal tissue. It is commonly used as an adjunct to more standard methods for gaining hemostasis, such as suturing or use of topical hemostatic agents.

The potential adverse events associated with the use of BIOGLUE® include:
  non-adhesion of the product to tissue
  application of the adhesive to tissue extraneous to procedure
  inflammatory and immune reactions
  allergic reaction
  tissue mineralization
  local tissue necrosis
  vessel obstruction
  bronchial or luminal obstruction
  thrombosis and/or thromboembolism
  pulmonary embolism
  injury or damage to normal vessels or tissue
  possible transmission of infectious agents from material of animal origin.

In other examples, alternate compositions with different concentrations of BSA and glutaraldehyde components may be provided at different concentrations and/or used with different ratios, e.g.:
  1. 45% BSA and 40% glutaraldehyde components in a 1:1 ratio
  2. 45% BSA and 20% glutaraldehyde components in a 2:1 ratio
  3. 36% BSA and 8% glutaraldehyde components in a 4:1 ratio
  4. 36% BSA and 12% glutaraldehyde components in a 3:1 ratio In another example, TISSEEL® sealant (Baxter Healthcare; Deerfield, Ill.) may be used for the glue, matrix or carrier component of the $^{90}$Y composition. TISSEEL is a two-component fibrin sealant that is manufactured from pooled human plasma. When the two components, the sealer protein and thrombin, are combined, the composition is similar to the final stage of the blood component cascade. The sealer protein is a sterile, non-pyrogenic, vapor heated and solvent/detergent treated preparation made from pooled human plasma. The sealer protein is provided either as a freeze-dried powder for reconstitution with a fibrinolysis inhibitor solution or as a finished frozen solution pre-filled into one side of a dual-chambered syringe. The active ingredient of the sealer protein is fibrinogen. The sealer protein solution contains a fibrinolysis inhibitor comprising synthetic protinin, that delays fibrinolysis. The aprotinin is manufactured by solid phase synthesis from materials completely of non-human/non-animal origin. The composition of the sealer protein solution has a total protein level of 96-125 mg/mL, fibrinogen 67-106 mg/mL, aprotinin 2250-3750 KIU/mL, and also human albumin, tri-sodium citrate, histidine, niacinamide, polysorbate 80 and water for injection. The thrombin component is a sterile, non-pyrogenic, vapor heated and solvent/detergent treated preparation made from pooled human plasma. Thrombin (human) is also provided either as a freeze-dried powder for reconstitution with calcium chloride solution or as a finished frozen solution pre-filled into one side of a dual-chambered syringe. The thrombin solution contains 400-625 units of thrombin/mL, 36-44 μmol/mL of calcium chloride, and also some human albumin, sodium chloride and water for injection. The two components of TISSEEL, the sealer protein and thrombin, can be provided in dual-chamber syringes with 2 mL, 4 mL, and 10 mL total volume, of equal chamber sizes, e.g. dual chambers of 1 mL, 2 mL and 5 mL per chamber, and are provided in a 1:1 ratio. In other examples, the concentrations of the sealer protein solution and the thrombin solution may be different such that a non-equal ratio of sealer protein solution and the thrombin solution is used.

Another dual solution sealant that may be used is BOLHEAL® (Chemo-Sero Therapeutic Institute; Kumamoto, J P), which comprises a first solution of 80 mg/mL human fibrinogen, 75 IU/mL of human plasma-derived coagulation factor (XIII) and 1000 KIE bovine aprotinin, and a second solution of 250 IU/mL of human thrombin and 5.9 ml/mL of calcium chloride, which are mixed at the point of use in a 1:1 ratio.

Another matrix that may be used in the $^{90}$Y-matrix system is SURGIFLO® (Ethicon, Inc; Somerville, N.J.), which comprises a first component of 8 mL of flowable sterile gelatin and a second component of 2000 IU of lyophilized human thrombin powder that is reconstituted using 2 ml of sterile water for injection.

In still another example, a multi-component polyethylene glycol sealant, such as COSEAL® surgical sealant (Baxter Healthcare; Deerfield, Ill.), may be used. The COSEAL® may comprise a pre-filled applicator or syringe components, with two liquid storage compartments and one dry powder compartment. One solution is a dilute HCl solution and the other is a sodium phosphate/sodium carbonate solution. The dry powder syringe contains a 4-arm polyethylene glycol polymer of 10 kDa molecular weight, where the arms are capped with thiol groups, and pentaerythritol poly(ethylene glycol) ether tetrasuccinimidyl glutarate. The two solutions are provided in equal size syringes. The dry powder is first reconstituted with the buffer liquid solution by forceful transfer back and forth at least 20 times between the dry powder and the buffer solution until the dry powder appears to be dissolved.

In other examples, the glue component may comprise a single component glue, sealant or matrix, e.g. a cyanoacrylate, alginate, polyvinyl alcohols, sodium polyacrylate, agarose, methylcellulose, carboxymethylcellulose, hyaluronic acid, etc.

During the procedure, one or more of the following may be recommended:
  Maintain the position of surgical gloves, sterile gauze swab/towels and other surgical instruments separate from the matrix to minimize the potential and inadvertent adhesion of the matrix to these surfaces The syringes, applicators and tip-applicator extensions are to be used exclusively for a single patient. Do not re-sterilize.

Do not use if the packaging is open or damaged.

Be careful not to accidentally spill the contents of the syringe

Do not press the syringe plunger while connecting to the syringe.

Avoid contact of fabrics with material expelled from the applicator during priming.

The matrix component of $^{90}$Y-matrix composition can polymerize quickly. Priming must take place quickly and it should be followed immediately by application of the compound. A pause between priming and application can cause polymerization in the tip-applicator. It is recommended:

Do not use blood collection devices while aspirating excess $^{90}$Y-matrix composition from the surgical field Do not apply matrix in an excessively wet surgical field. This may cause poor grip.

Do not detach or peel the $^{90}$Y-matrix composition from a point or surface where it has come into contact inadvertently, as this may cause damage to the fabric.

Do not implant $^{90}$Y-matrix composition in closed anatomical sites that are in the immediate vicinity of nerve structures.

Use caution when using the $^{90}$Y-matrix composition in pregnant or lactating women. There are currently no efficacy or safety studies concerning $^{90}$Y-matrix composition use in pregnant or lactating women.

Due to the radioactivity of this device and the significant consequences of incorrect product placement, physicians should not implant this product without proper training on the handling and implant technique.

All persons who handle, dispense and implant this device must know and comply with all local and state regulatory requirements governing therapeutic radioactive materials. The accepted radiation protection techniques should be used to protect personnel when handling both the isotope and the patient.

Some patients may experience gastric problems after treatment with $^{90}$Y-matrix composition, but H-2 blocking agents can be used the day before the implant and continued, if necessary, to reduce gastric complications.

The radioisotope component of the $^{90}$Y-matrix composition showed a slight potential for sensitization when tested on skin in an animal model.

Do not use the $^{90}$Y-matrix composition if personnel are not adequately protected (i.e., wear gloves, mask, protective clothing and safety glasses). Unpolymerized glutaraldehyde can cause irritation to eyes, nose, throat or skin, as well as breathing difficulties and local tissue necrosis. Prolonged exposure to unpolymerized glutaraldehyde, which is a component of BIOGLUE®, can cause heart or central nervous system disorders. In the event of contact, immediately rinse the affected areas with plenty of water and seek medical attention.

Do not use the $^{90}$Y-matrix composition in the presence of infections and use cautiously in contaminated areas of the body.

Exercise caution in repeatedly exposing the same patient to multiple applications of the $^{90}$Y-matrix composition. Reactions due to hypersensitivity are possible during exposure to the matrix component. Sensitization phenomena have been observed in animals.

Some of the $^{90}$Y-matrix components contain a material of animal origin that may be able to transmit infectious agents.

Potential side effects of the procedures described herein may include:

failure of the product to adhere to the tissue or treatment side, application of the adhesive to a tissue not subject to the procedure, inflammatory and immune reaction allergic reaction tissue mineralization necrosis of local tissue obstruction of the vessels bronchial or luminal obstruction thrombosis or thrombo-embolism pulmonary embolism damage to normal vessels or tissues possible transmission of infectious agents from the material of animal origin.

fever temporary reduction of hemoglobin altered biochemical tests (mild to moderate) concerning the liver (e.g. ALT, AST, alkaline phosphatase, bilirubin)

abdominal pain nausea vomiting diarrhea

In some variations, the devices, kits and methods described herein may be used to treat one or more target locations following surgical resection or ablation, in order to treat any residual tumor cells, but in other variations, the target locations may be treated prior to resection, e.g. to attempt to downgrade the cancer stage in order to convert an unresectable tumor to a resectable tumor. In still other variations, the target locations may be treated without any plans to perform a surgical or ablative procedure. In some variations, the therapy may be used to treat non-cancerous disease or symptoms, e.g. intra-articular injection to treat synovitis, intradermal injection to treat keloids and hypertrophic scars, intravascular injection for hemangioma, etc.

In one exemplary embodiment, a method for treatment of a small tumor utilizes a mixing injector configured to be connected to a supply injector of glue and to a supply of radiotherapeutic particles. The vial is removed from its packaging and, without shaking or otherwise reconstituting the suspension of the microspheres in the water, a predetermined amount of non-agitated or non-microsphere containing suspension liquid is first removed, e.g. 0.5 mL, 1 mL, 1.5 mL, 2 mL, or 2.5 mL, or 10%, 20%, 30%, 40% or 50%. In other variations, the amount of liquid removed can vary, but results in a suspension liquid that has an activity to volume ratio that is 0.5 GBq, 0.8 GBq, 1.0 GBq, 1.2 GBq, or 1.5 GBq per 1 mL, for example, or in a range between any two of these ratios. After removal of some of the suspension liquid, the vial is reconstituted via shaking or other agitation. Based on the remaining concentration of the radiotherapeutic, e.g. 3 GBq in 4 ml suspension liquid, the desired amount of activity is withdrawn, based on the volume, into the radiotherapy transfer syringe. In some examples, the radiotherapy transfer syringe is the same syringe used to remove the predetermined volume of non-agitated or non-microsphere suspension liquid, but in other examples, a different syringe is used for non-agitated or non-microsphere suspension liquid removal.

The matrix syringe is then uncapped. In some examples, a predetermined volume of glue from the glue source syringe may be dispensed, based on the calculated volume of microspheres/suspension liquid, in order to accommodate the volume of microsphere solution that is needed to deliver the desired activity level of microspheres. In some variations, additional volume may be provided in the syringe by pulling back the plunger mechanism. In other variations, no volume adjustment to the matrix syringe is needed before adding the isotope solution, because of existing air gaps provided in the matrix syringe are sufficient to hold the amount of radioisotope to be transferred.

In some variations comprising a two-component matrix, the radiotherapeutic-matrix composition is delivered using a mixing tip that may mix the two components within 1, 2 or 3 cm of the distal ends of the chambers containing the components. The distal end of the mixing tip may comprise multiple distal openings that may comprise a generally linear configuration across a transverse dimension of the mixing tip, in order to increase the single-pass coverage area of the mixing tip. For the example, the mixing tip may comprise 2, 3, 4, 5, 6, 7 or 8 distal openings that are aligned along a transverse dimension that is at least 1, 1.5, 2, 2.5 or 3 cm wide.

In other variations, the delivery kit may comprise dual-lumen tubing, dual-lumen needle or a dual-lumen catheter so that the mixing or polymerization of the two components occurs more distally, in order to avoid polymerization of the components within a single-lumen tubing or catheter, which may result in clogging before the matrix reaches the target location. These delivery components may be preferred when the distance from the skin surface to the target surface is more than 2, 3, 4 or 5 cm from the ends of the chambers containing the matrix components.

In one example, the delivery kit may include a dual-lumen injection needle or introducer needle. The needle may be a needle measuring 11G, 12G, 13G, 14G, 15G, or 16G, and comprise a shaft length in the range of 100 mm to 200 mm, 120 mm to 150 mm, or 140 mm to 170 mm, for example. The needle may be made from AISI 302, 304, or 306L stainless steel, and attached to a proximal female Luer lock hub. The needle may also include a stylet configured for insertion through the lumen of the needle, the stylet comprising a solid core with or without a pointed or piercing distal tip that extends out of the distal end of the needle. The needle may be used with a coaxial double-lumen catheter with a diameter of 12G, 13G, 14G, 15G, 16G, 17G or 18G, and comprise a shaft length in the range of 100 mm to 300 mm, 150 mm to 250 mm, or 170 mm to 200 mm, for example. The catheter may also comprise a proximal Luer lock hub. The hub of the catheter may also be configured to lock with the proximal Luer lock hub of the introducer needle, e.g. via a male Luer lock structure that can lock to the introducer needle hub when the catheter is inserted through the needle hub and needle shaft, or a deformable or biased clamp structure that reversibly attaches to the exterior surface of the introducer needle hub, for example. The needle and catheter diameters may be selected such that the catheter is configured to be removably inserted through the introducer needle without significant leakage of bodily fluid between the outer wall of the catheter and the inner lumen wall of the introducer needle, e.g. the catheter may be at least 1G or 2G smaller in size than the introducer needle.

In one specific example, the kit 10 from SVAS Biosana, depicted in FIG. 1A, may be used, which includes a 15G× 150 mm coaxial introducer needle 12 and a 16G×120 mm coaxial catheter 14, configured to work with each other. The proximal end of the introducer comprises a male Luer lock hub 16, such that the distal end 18 of the catheter hub 20 comprises a female Luer lock hub that can engage the male Luer lock hub 16 when the catheter 14 is inserted into the introducer 12. The proximal end 22 of the catheter hub 20 further comprises a connector configured to attach to a matrix syringe or matrix injection system. This may be, for example, a proprietary complementary female connector interface to a BIOGLUE® injection syringe, or a female Luer lock hub. The kit 10 may also comprise a stylet 24 that is reliably lockable and insertable into the introducer 12, and is used during insertion and positioning of the introducer 12 to the target location. The stylet 24 may include a solid proximal end 26 that comprises a releasable clamp mechanism to attach to the proximal hub of the introducer 12, or may comprise a female Luer lock in other examples. FIG. 1B depicts the catheter 14 inserted into the introducer 12, with the male Luer lock hub 16 engaged with the female Luer lock hub 18.

In one example, the vial or bottle with the radioisotope microspheres is retrieved from its radioprotective container, and optionally placed in a lead or acrylic open-top box, if available. The seal on the vial is cleaned with an alcohol swab, and then an air opening is formed in the seal by puncturing the seal with a needle. The needle, such as a 22G, 25G, 28G, 30G, 31G or 32G hypodermic needle is optionally left in place. A 5 mL syringe is then attached to a 20G or 22G needle with a length in the range of 50 mm to 150 mm, 50 mm to 120 mm, or 70 mm to 100 mm. The syringe and attached needle are then used to re-puncture the seal. Without agitating or mixing the settled microspheres at the bottom of the vial or bottle, the needle tip is positioned within the suspension liquid but above the settled microspheres, and 2 mL of suspension liquid is removed and discarded, preferably without significant removal of any microspheres. Using a dose calibrator, the activity remaining in the vial or bottle is checked or confirmed. Assuming that the vial or bottle contained 3 GBq in 5 mL of suspension liquid, the vial or bottle should now nominally contain 3 GBq in 3 mL of suspension liquid. In other variations, a different amount of suspension liquid may be removed, or additional suspension liquid, such as Water For Injection or isotonic sodium chloride solution, may be added to the vial or bottle to alter the concentration of the activity per volume.

The target activity level and volume to be injected into the target lesion is then determined or based on (a) the calibrated or nominal activity concentration in the vial, (b) the target activity level or absorbed dose to be delivered to or achieved in the target lesion(s) respectively, and (c) optionally accounting for the residual volume of material that may be in the syringe injection system after a full or maximum injection, e.g. residual volume in the syringe tip distal to the plunger or sliding seal of the syringe, and in the mixing tip or injection catheter or needle. The target-absorbed dose may be, for example, 18 Gy or 20 Gy to the surgical beds from resected breast lesions, and 150 Gy for hepatic lesions. The syringe and attached needle is then reinserted into the vial or bottle and is used to agitate and suspend the settled microspheres in the suspension liquid by moving the plunger of the syringe back and forth several times, e.g. 10 to 20 times, and/or until sufficient mixing is visually confirmed by the homogenous appearance of the suspension liquid and without any visibly settled microspheres. The target activity volume is then removed using the syringe. The syringe cap of the glue/matrix syringe is then removed, and the target activity volume of the suspension liquid with microspheres is then distributed between the two chambers of the glue/ matrix syringe in a 4:1 ratio to the BSA:glutaraldehyde chambers, or in a ratio corresponding to their cross-sectional areas or volumes of the matrix component chambers. For other syringe/injection systems, for example, where there is a 1:1, 1.5:1 or 2:1 volume or cross-sectional area ratio between the two chambers, the target volume will be distributed in a 1:1, 1.5:1 and 2:1 ratio. For a three-chamber delivery system, e.g. a 1:1:1 or 4:1:1 or 4:2:1 ratio injection system, the target volume would be distributed by the same ratio to the three chambers, respectively.

After distributing or loading the target activity volume into the matrix syringe, the syringe cap is placed back on the matrix syringe. A commercially available dose calibrator commonly used in a radio-pharmacy may be used to confirm the expected activity in the syringe, and correct it, if needed. The loaded matrix syringe is then placed back in its radioprotective container for storage or transport to the operating room or procedure facility.

At the operating room or procedure facility, the patient is prepped and draped in the usual sterile fashion, and anesthesia is achieved. The target lesion, e.g. hepatic lesion, is identified using an imaging modality such as ultrasound or fluoroscopy or based on prior imaging, the imaging performed with or without the use of any contrast agent. A stylet is inserted into the introducer needle, and is then percutaneously inserted into the target lesion, preferably with ultrasound or CT guidance. The pre-filled syringe previously loaded with the radiotherapeutic particles is removed from its radioprotective container and the syringe cap is removed by holding the syringe upright and rotating the cap from side to side. The bilateral cap of the coaxial catheter is then aligned with the two openings of the dual-chamber syringe. Indicia on the catheter may be provided to facilitate the alignment with the syringe. The catheter may then be locked onto the syringe using a locking collar or other locking mechanism, such as to resist inadvertent separation of the syringe and catheter.

Upon optionally reconfirming the position of the introducer/catheter combination, the plunger or actuator of the syringe/delivery system is actuated to dispense the mixture. In some examples, the syringe plunger or delivery system actuator may be actuated at a rate of approximately 0.5 mm to 1 mm per second, 0.5 mm to 2 mm per second, or 0.5 mm to 1.5 mm per second. Once delivery is completed, the introducer needle/catheter may be left in place for 30 to 60 seconds, or at least 5 seconds, 10 seconds, 15 seconds, 20 seconds or 30 seconds, and/or no more than 30 seconds, 45 seconds, 60 seconds, 90 seconds, or 120 seconds. This may ensure polymerization at the target location, after which the introducer needle/catheter may be removed from the target location, using an optional twisting motion to ensure adequate separation of the matrix from the introducer needle/catheter without seeding of the insertion tract or pulling of the target location due to incomplete separation of the injected matrix and the introducer needle/catheter. The introducer needle/catheter insertion site may then be checked for any fluid leakage and optionally stitched or sealed with non-radioactive bioglue or matrix, and then bandaged and dressed as needed. Any radioactive or biohazardous components are disposed as appropriate.

After the desired amount of the composition has been administered or delivered, the stylet is then removed from the inserted introducer while maintaining the position of the introducer. The syringe/catheter is then inserted through the introducer until the distal hub of the catheter locks with the proximal hub of the introducer.

In embodiments that do not require percutaneous access with a needle or catheter, in the procedure above a mixing tool tip may be attached to the mixture syringe instead of achieving access with the introducer followed by attachment of a needle and/or catheter. After attachment of the mixing tip, the syringe may be shaken to sufficiently mix the radioisotope suspension with the glue or matrix components. The syringe plunger or delivery system actuator may then be actuated at a rate of approximately 0.5 mm to 1 mm per second to apply the mixture to the surface of the surgical cavity. Once delivery is completed, the surgical cavity may be left exposed for 30 to 60 seconds to ensure polymerization at the target location. The surgical cavity may then be closed and dressed in the usual fashion. Any radioactive or biohazardous components are disposed as appropriate.

In other examples, the radioisotope microparticles may be premixed at the point of manufacture with one or both components of the matrix or glue of a prefilled syringe. For example, the $^{90}Y$ microspheres may be pre-mixed and loaded with the BSA and/or glutaraldehyde component of the prefilled syringe. In some variations, because of potentially different treatment concentrations that are necessary for particular lesion sizes or diseases, different sized syringes with different treatment concentrations may be provided. For example, 1 mL, 2 mL, 5 mL or 10 mL prefilled syringe injection systems may be provided but with different activities per mL pre-mixed with the BSA component but with no activity in the glutaraldehyde components. The syringes may comprise an activity concentration in the range of 5 MBq to 50 MBq per mL, 7 MBq to 45 MBq per mL, 7 MBq to 40 MBq per mL, 15 MBq to 40 MBq per mL, or 15 MBq to 30 MBq per mL. These concentrations may be used, for example, in the treatment of breast cancers. In other examples, the 1 or 2 mL syringes may comprise an activity concentration in the range of 0.1 MBq to 20 MBq per mL, or 0.2 MBq to 15 MBq per mL, and the 5 mL or 10 mL syringes may comprise an activity concentration in the range of 3 MBq to 30 MBq per mL, or 5 MBq to 25 MBq per mL. The concentrations of these syringes may be used with more radiosensitive tumors or where effects on the surrounding normal tissue need to be reduced, e.g. HCC. Specific examples of dose selection for hepatic and breast cancers are provided in certain examples later below.

Dosimetry

As noted previously, hepatocellular carcinoma (HCC) is the most common primary liver malignancy and is a leading cause of cancer-related death worldwide. It is an aggressive cancer typically occurring in the setting of cirrhosis. Unfortunately, it commonly presents in advanced stages, when patients have become symptomatic and have some degree of liver impairment. In the United States, a total of 30,640 new liver and intrahepatic bile duct cancers occurred in 2013, in addition to 21,670 deaths. HCC occurred more often in males than females (2.4:1), with a higher incidence in Eastern and Southern Asia, Middle and Western Africa, Melanesia, and Micronesia/Polynesia. Despite major advances in prevention techniques, new technologies and screening procedures (in both diagnosis and treatment), incidence and mortality are increasing, with cirrhosis being the most important risk factor for the development of HCC regardless of etiology. Today, multiple treatment modalities exist. However, only orthotopic liver transplantation or surgical resection may be regarded as curative. Other treatment modalities include transarterial chemoembolization, radioembolization, percutaneous ethanol injection, radiation therapy, and ablation therapies. In particular, percutaneous ablation is a promising approach to treating inoperable primary tumors or metastases in the liver. In fact, in the treatment of HCC, fewer than 40% of patients are candidates for surgery, and the possibility of recurrence after curative surgery is generally high. Against this backdrop, percutaneous techniques represent a successful therapeutic option and are widely used today for the treatment of metastatic and small primary tumors. Among these techniques, methods such as chemical ablation, cryoablation, high temperature ablation (e.g. radiofrequency, microwave, laser, and ultrasound) have gained wide acceptance for the treatment of liver tumors as they may serve as a bridge for transplant candidates, especially in relation to small primary lesions. Selection of a treatment modality is based on tumor size, location, extrahepatic spread, and underlying liver function.

Due to the lack of effective systemic therapies for HCC, researchers have been investigating the use of locoregional tumor control with $^{90}$Y radioembolization since the 1960s. Today radioembolization (or Selective Internal Radio Therapy, SIRT, also known as Trans Arterial Radio Embolization, TARE) is an established and effective treatment for liver malignancies based on trans-arterial infusion of $^{90}$Y-laden microspheres. Radiation dose distributions arising from intrahepatic arterial infusion of $^{90}$Y microspheres have been investigated by a number of authors in the past. At present, there are two clinically available microsphere devices in which $^{90}$Y is incorporated: one with microspheres made of glass (TheraSphere; MDS Nordion, Ottawa, Ontario, Canada) and the other with microspheres made of resin (SIR-Spheres; Sirtex Medical, Sydney, Australia). The resin microsphere device consists of biocompatible $^{90}$Y-bearing microspheres with diameters of 20-40 µm. Once administered, the spheres remain in the liver as a permanent implant.

In the traditional catheter-based approach, radioembolization involves intra-arterial infusion of microspheres. However, in recent years a number of studies have addressed the problem of dosimetry in therapies based on the use of intratumoral administration of $^{90}$Y-conjugates by percutaneous puncture. In recent years, this technique has been successfully applied to patients treated with Y-labeled [DOTA$^0$-D-Phe$^1$-Tyr$^3$]octreotide ($^{90}$Y-DOTATOC) for malignant gliomas.

Furthermore, based on the clinical experience gained in liver radioembolization, percutaneous ablation of HCC through the intratumoral injection of an appropriate activity of $^{90}$Y has the potential to reduce drastically the chances of local recurrence. In this context, there is growing interest in the development of new intratumoral procedures for HCC throughout a localized administration of $^{90}$Y in the form of microspheres mixed with biocompatible compounds.

As a rule, intratumoral administration of radionuclides raises questions about the dosimetry of small lesions as this approach allows sub-centimeters tumors to be selectively treated. To date, there is no simple way to assess exactly the absorbed dose to tumors and normal liver tissue when $^{90}$Y is administered. This is because $^{90}$Y only emits pure beta radiation with limited penetration range in tissue. Consequently, the delivered dose is highly dependent on the distribution of microspheres and the tumor mass. In particular, the current analytic formalism used to assess the absorbed dose to the liver and to the tumor masses inside the liver parenchyma is based on the assumption that all particles released from $^{90}$Y within a given organ are fully absorbed by that organ. However, when the tumor size is small this assumption may no longer be true and the current analytic approach is likely to provide inaccurate dose results when used to assess the dose in small target regions.

Thus, the current analytic formalism used to assess the absorbed dose after the administration of $^{90}$Y-microspheres may provide inaccurate results when used to calculate the dose in small target regions, as it is based on the assumption that all β-particle energy is fully absorbed by the treated mass. The present work assesses the absorbed dose in a scenario of intratumoral injection of $^{90}$Y in lesions of varying size, and provides a dosing regimen that accounts for partially absorbed β-particle energy that is fully absorbed by the treated mass.

In one example, the absorbed dose in small lesions are assessed, assuming a selective delivery of $^{90}$Y into the tumor (i.e. in a scenario of percutaneous ablation of HCC through the intratumoral injection of the radionuclide). A simplified model for tumor masses was implemented into MCNP4C Monte Carlo (MC) code with the aim to determine the absorbed dose to the lesion when the tumor mass is uniformly filled with $^{90}$Y.

In some variations, the absorbed dose-per-unit administered activity was assessed using Monte Carlo calculation in spheres of different size (diameter 0.5-20 cm). The spheres are representative of tumor regions and are intended to be uniformly filled with $^{90}$Y. Monte Carlo results were compared with the well-established analytic approach.

The initial results indicate that the use of the current analytic model provides dose overestimations below 10% for lesions with a diameter larger than approximately 2 cm. However, for lesions with a diameter smaller than 2 cm, the analytic model is likely to deviate significantly (>10%) from Monte Carlo results, providing dose overestimations larger than 50% for lesions of 0.5 cm diameter. An alternative equation is provided for the calculation of the absorbed dose in small target regions.

$^{90}$Y disintegrates by p emission mainly (99.983%) to the stable Y ground state level. A weak beta branch occurs to the 1760 keV excited level that decays by an E0 gamma transition. This $0^+$-$0^+$ transition is followed by the emission of two gammas, or an electron-positron pair, or internal conversion. The adopted half-life of $^{90}$Y ground state is 64.041 hours or 2.6684 days.

Among the radionuclides used in clinical practice, $^{90}$Y has attractive physical and radiobiologic features that make this radionuclide suitable for a loco-regional therapeutic option. The high-energy β-particles (maximum energy 2278.7 keV, average energy 926.7 keV) and their penetration depth (maximum particle range in tissue, 11 mm; range in tissue after which 50% of the energy particles is transferred, 4 mm) allows high radiation doses to be selectively delivered to the target area, while sparing surrounding tissues and normal organs. In particular, the penetration depth of the high-energy β-particles is a key element of this radionuclide's success in radioembolization, allowing for high-dose deposition into the tissues between embolized capillaries. In the traditional dose calculation formalism (after locoregional administration of $^{90}$Y), two important simplifying assumptions are generally made:

β radiation released from $^{90}$Y within a given organ is fully absorbed by that organ. In most cases, this assumption is supported by the average 4 mm $^{90}$Y β range in tissue.
permanence of $^{90}$Y in the area where they have been delivered (i.e. no migration of the radiopharmaceutical outside the tumor region).

Combining these two assumptions allows for easy calculation of average absorbed dose to an organ of interest on a macroscopic scale. The calculation, carried out using most up-to-date nuclear data for $^{90}$Y, is illustrated below and it is generally referred to as the MIRD (Medical Internal Radiation Dose) approach:

$$E_{avg} = \int_0^\infty E\varphi(E)dE = 926.7 \text{ keV} = 1.485 \cdot 10^{-13} \text{ J} \tag{1}$$

$$E_{tot} = A_0 E_{avg} \int_0^\infty e^{-\lambda t} dt = \frac{A_0}{\lambda}(1.487 \cdot 10^{-13} J) = A_0 \cdot k \tag{2}$$

where $E_{avg}$ is the average energy released per decay of $^{90}$Y based on the probability density function $\varphi(E)$ for emission, $\lambda$ is the $^{90}$Y decay constant based on the half-life of 64.041 hours, and k a constant term. $A_0$ is the activity present in the organ in GBq and $E_{tot}$ is the total energy released by $A_0$ from the time that it is infused until it has fully decayed.

Assuming that all of the energy of the β-decay is absorbed in the volume where the decay occurs, the constant term, k, can be calculated taking the given physical values and their statistical uncertainties:

$$k = \frac{1.487 \cdot 10^{-13} J}{\lambda} = \frac{1.487 \cdot 10^{-13} J \cdot 230547 s}{0.69315} \cdot \frac{10^9 \frac{dis}{s}}{GBq} = 49.38 (J/GBq) \tag{3}$$

The constant factor 49.38 (J/GBq) is the energy released per unit activity of $^{90}$Y. The adopted uncertainties on the nuclear data reported in the equation below lead to a relative standard uncertainty of 0.1% on the constant term, i.e. 49.38(5) (J/GBq), in line with recommendations from the American Association of Physicists in Medicine.

Finally, the absorbed dose D (expressed in Gy) can be obtained by dividing the delivered energy, $E_{tot}$, by the mass of the target region m (expressed in kg):

$$D_{avg}(Gy) = \frac{A_0(GBq) \cdot 49.38(J/GBq)}{m \text{ (kg)}} \tag{4}$$

Of note, the same formula with a slightly different constant term, k, has been reported in other publications (e.g. 49.98, 49.67).

According to the partition model, the equation above can be used to calculate the absorbed dose in the tumor, once the fractional tumor uptake $FU_{tumor}$ (i.e. the fraction of the administered activity accumulated in the tumor) is known:

$$D_{tumor}(Gy) = \frac{A_0(GBq) \cdot 49.38(J/GBq) \cdot FU_{tumor}}{m \text{ (kg)}} \tag{5}$$

It must be reiterated that equations (4) and (5) above are only valid for $^{90}$Y radioembolization and only representative of average absorbed dose in an organ or a large lesion, i.e. on a macroscopic scale. It is hypothesized herein that these equations may not hold for very small tumor masses, as the assumption that the energy emitted during decay is totally absorbed by the mass of interest m is no longer true. In particular, when the size of the lesion is very small (especially in the sub-centimeter region), the energy released per unit activity of $^{90}$Y may decrease significantly. Therefore, hereafter the constant term k in equation (3) will be treated as a function of the lesion radius (r) and indicated as k(r).

In the present study, the absorbed dose-per-unit administered activity was assessed using Monte Carlo calculations in a simplified geometry. MC code MCNP4C has been used for this purpose. MCNP is a general-purpose, continuous-energy, generalized-geometry, time-dependent, coupled neutron/photon/electron Monte Carlo transport code. For photon transport, the code takes into account photoelectric absorption, with the possibility of K- and L-shell fluorescent emission or Auger electron, coherent and incoherent scattering and pair production. The photoelectric cross sections are based on Storm and Israel whereas the scattering cross sections are taken from ENDF tabulations. The continuous slowing down approximation energy loss model is used for electron transport.

Spherical lesions of different size (diameters in the range 0.5-20 cm) were simulated for two different densities: ρ=1.00 g/cm$^3$ (water density) and ρ=1.05 g/cm$^3$ (liver density). In both scenarios, spheres were assumed to be immersed in a semi-infinite medium with the same density of the sphere. The spheres are representative of tumor regions and are supposed to be uniformly filled with $^{90}$Y, while the surrounding medium is assumed to contain no radioactivity.

Calculations were performed in coupled electron-photon mode [MODE P E] using the e103 electron interaction data library (ELIB=03E) and the mcnplip2 photon interaction data library (PLIB=02P). Simulations were carried out taking into account all the available advanced options, such as electron production by photons, Bremsstrahlung effect and knock-on electron production. MCNP simulations were run for an adequate time to get a statistical uncertainty on the absorbed dose below 0.01%.

Figure 18:
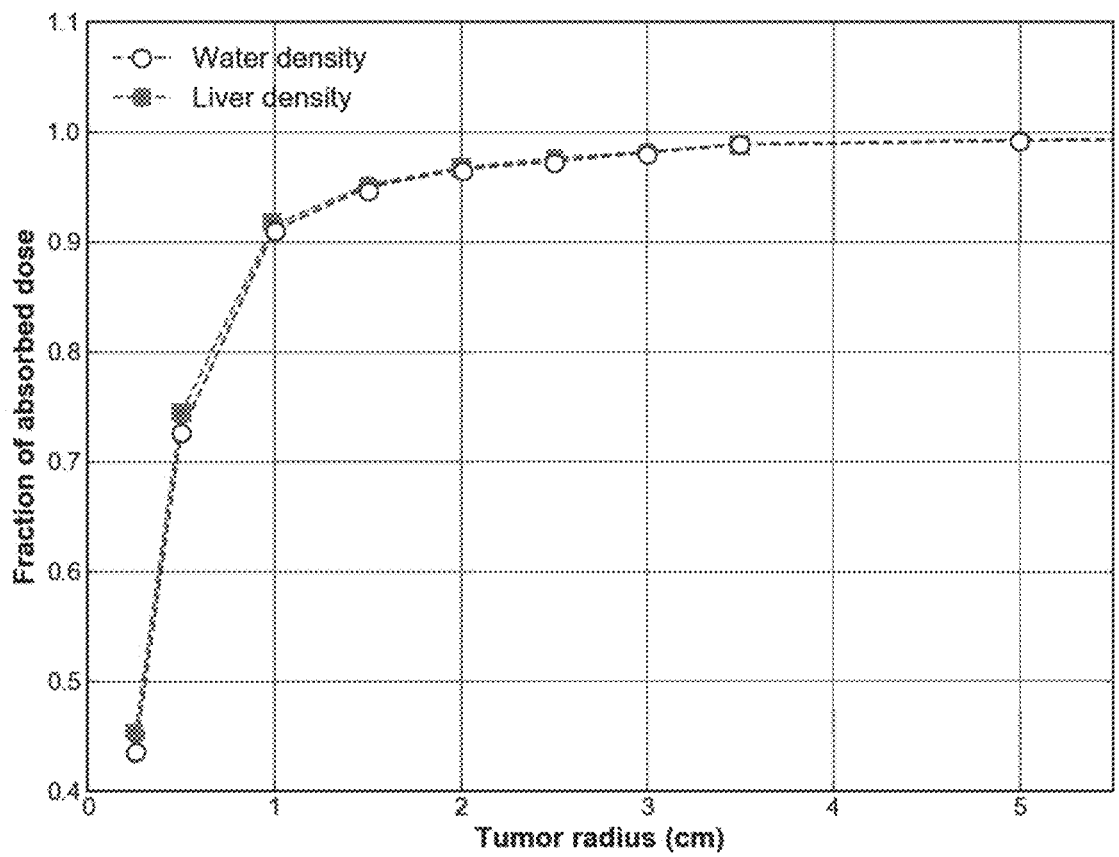
FIG. 18 is a graph of the faction of $^{90}$Y absorbed dose into the tumor as a function of tumor size, with simulations performed for $\rho=1.00$ g/cm$^3$ (water density) and $\rho=1.05$ g/cm$^3$ (liver density)
Figure 19:
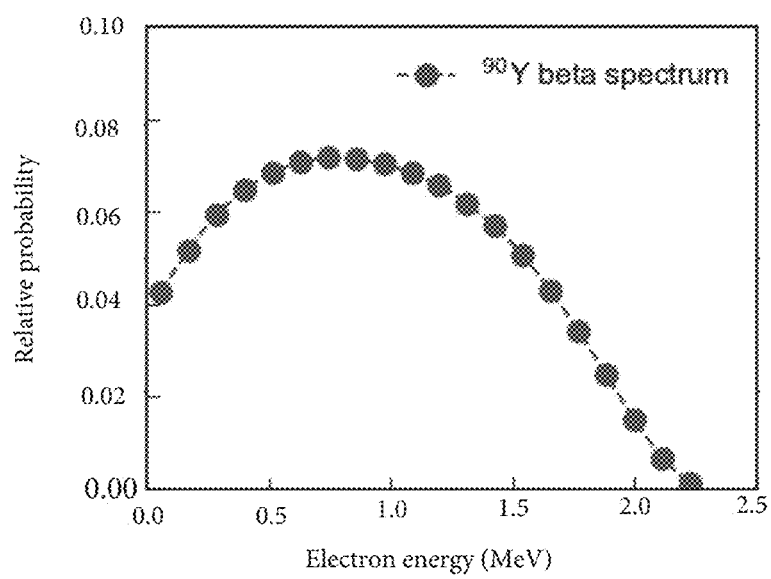
FIG. 19 is a graph of the $^{90}$Y beta spectrum implemented in the model used in FIG. 18A.
Figure 20:
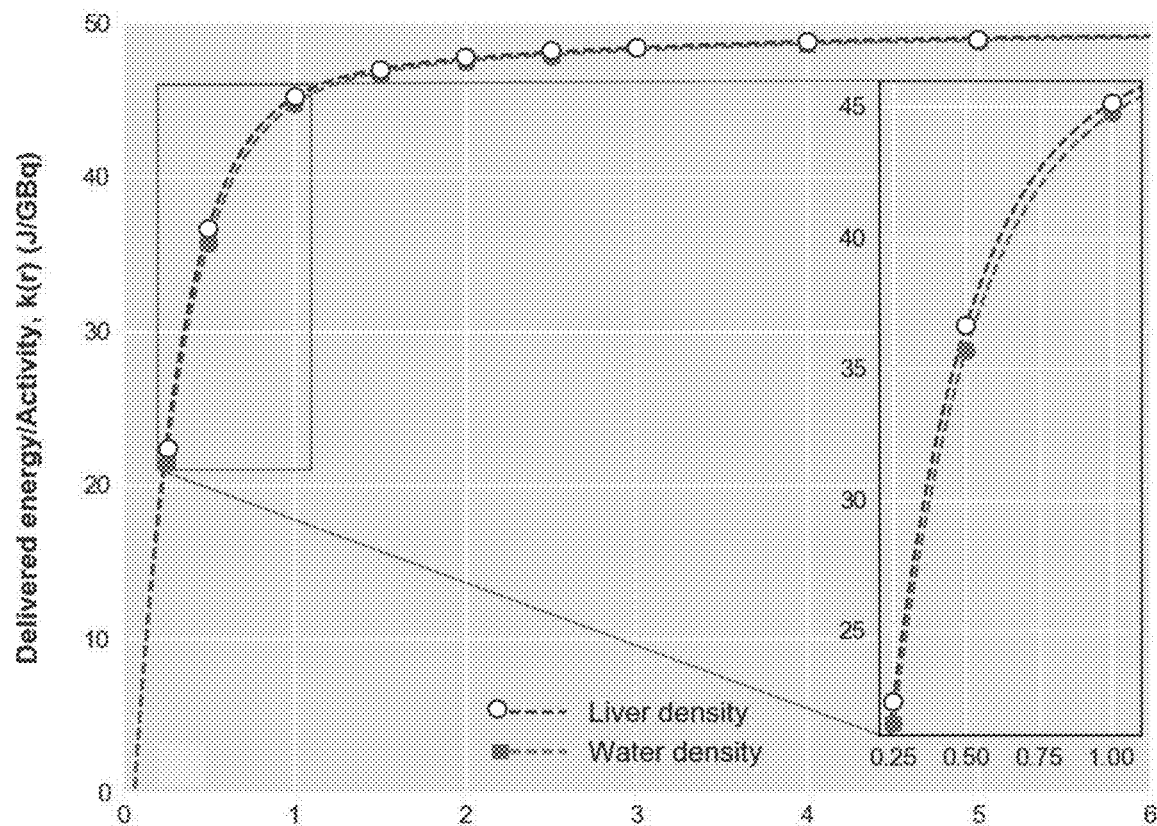
FIG. 20 is a graph of the delivered energy per unit activity of $^{90}$Y, k(r), calculated with MCNP4c as a function of the tumor diameter.

FIG. 18 shows the fraction of $^{90}$Y absorbed dose into the tumor as a function of the tumor size, obtained from MCNP simulations. The $^{90}$Y beta spectrum implemented in the model is also reported in the FIG. 19. Calculations were performed both for water spheres (ρ=1.00 g/cm$^3$) and for spheres made of liver tissue (ρ=1.05 g/cm). In both cases, when the lesion diameter drops below 2 cm, a greater amount of the β particle energy is delivered outside the sphere and the first of the above mentioned assumptions (radiation released from microspheres within a given organ is fully absorbed by that organ) does not hold. Consistently, the delivered energy per unit activity, k(r), shows the same trend (FIG. 20) confirming that when the tumor size is small, such term deviates significantly from its constant value of 49.38 (J/GBq), considered in equation (4). In order to use information reported in FIG. 20 at the clinical level, k(r) data obtained from MC calculations were fitted with the following function:

$$k(r) = k_0 + A \cdot \left(1 - \exp\left(-\frac{r}{a}\right)\right) + B \cdot \left(1 - \exp\left(-\frac{r}{b}\right)\right) \tag{6}$$

where r is the lesion radius in cm (assuming spherical tumors) and $k_0$, A, a, B, b are parameters determined by the fit, as reported in Table 1 below for both for water and liver density:

Fitting parameters of equation (6) with relative standard uncertainties, for water and liver density (denoted with superscripts $^W$ and $^L$, respectively). $R^2 = 0.999$ in both cases.

| Parameter | Value$^W$ | $U_{rel}^W$/% | Value$^L$ | $U_{rel}^L$/% |
|---|---|---|---|---|
| $k_0$ | −11.883 | 1.10 | −12.999 | 1.00 |
| A | 4.416 | 1.15 | 4.654 | 1.10 |
| a | 2.190 | 0.90 | 1.909 | 1.00 |
| B | 56.820 | 0.05 | 57.701 | 0.05 |
| b | 0.290 | 0.15 | 0.271 | 0.10 |

Figure 21:
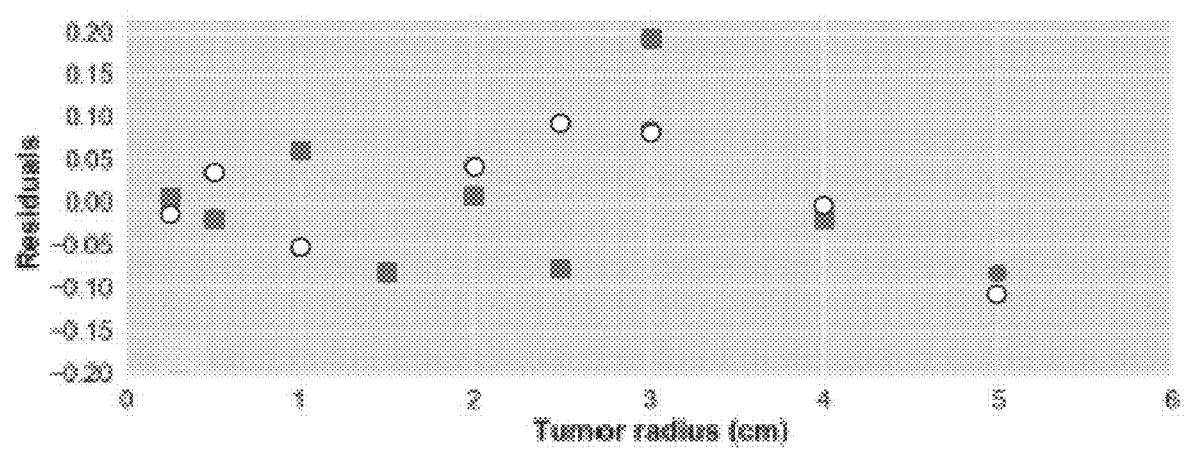
FIG. 21 is a graph of the residuals as a function of the tumor diameter.

An $r^2=0.999$ was obtained from the fit, both for water and liver density. Furthermore, goodness-of-fit was also assessed through the analysis of residuals (FIG. 21), which shows maximum deviations below 0.2 between calculated and fitted data, confirming the accuracy of the fit. Based on the fitting function described in equation (6), equation (4) can be rewritten in the following form:

$$D_{avg}(r) = \frac{A_0 \cdot k(r)}{m} \quad (7)$$

For a given activity $A_0$, equation (7) can be used to accurately calculate the absorbed dose for very small lesions (down to 0.5 cm diameter). The absorbed dose to lesions calculated using equation (7) provides results in good agreement with MC calculations (maximum deviation below 0.5%). As expected, when ideally r→∞ equation (7) reduces to equation (4). Of note, the energy per unit activity, k(r), obtained from equation (6) when x→∞ is 49.35 (J/GBq), against the accepted value of 49.38 (J/GBq) derived from equation (4) (0.06% deviation).

Figure 22:
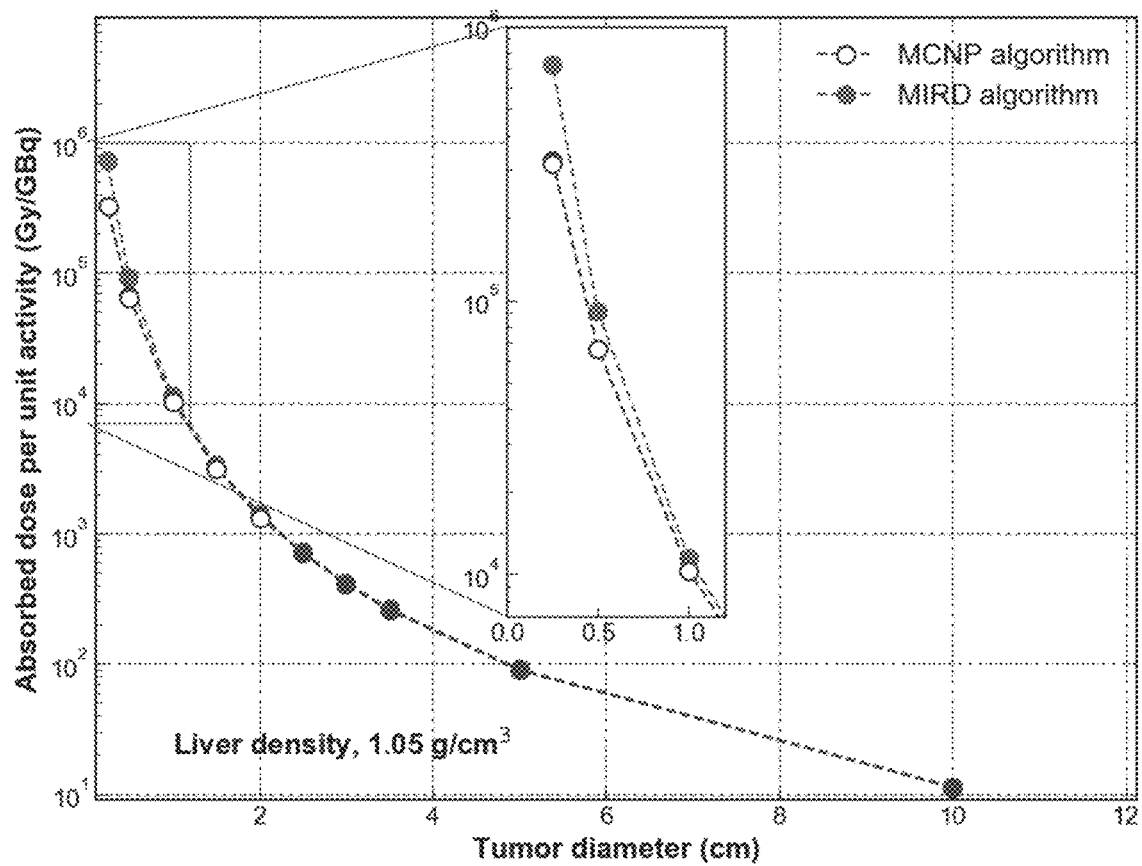
FIG. 22 is a graph of the absorbed dose per unit administered activity (GBq), for $\rho=1.05$ g/cm$^3$ (liver density), with an inset depicting the detail in the range from 0 cm to 1 cm lesion diameter.
Figure 23:
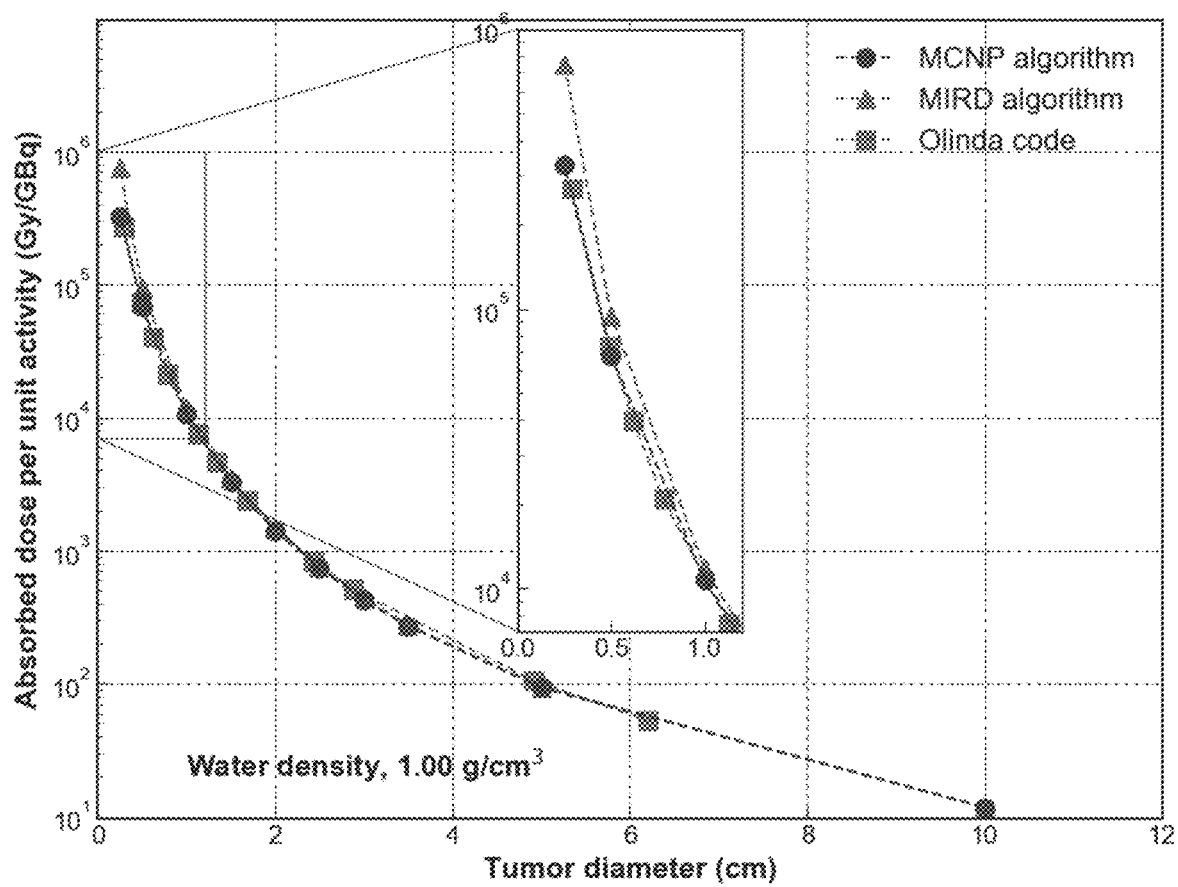
FIG. 23 is a graph of the absorbed dose per unit administered activity for $\rho=1.00$ g/cm$^3$ (water density), with an inset depicting the detail in the range from 0 cm to 1 cm lesion diameter.

FIG. 22 compares absorbed doses per unit activity (Gy/GBq) calculated with Monte Carlo with those obtained using the MIRD analytic approach, for spherical lesions of different size and for ρ=1.05 g/cm³. The same results for ρ=1.00 g/cm³ are shown in FIG. 23. In addition, FIG. 23 reports absorbed doses calculated using the well-established Olinda/EXM code, developed by the Radiation Dose Assessment Resource (RADAR) Task Group of the Society of Nuclear Medicine. As illustrated in FIG. 23, absorbed dose values calculated with the MC approach concur well with those obtained using Olinda/EMX. Significant deviations were found between MC calculated dose values and those obtained using the MIRD analytic approach when the lesion diameter drops below 2 cm (FIG. 23, inset).

Ultimately, Tables 2 and 3 below compare absorbed dose values per GBq of administered activity obtained with MC calculations ($D_{MCNP}$) and with the MIRD analytic approach ($D_{MIRD}$). The percentage differences between the two methods (last column of both tables, Δ) is also reported, calculated as $100 \cdot (D_{MCNP} - D_{MIRD})/D_{MIRD}$. The difference in absorbed dose values is within ~10% as long as the diameter of the lesion exceeds 2 cm. The two calculation approaches deviate significantly when the lesion size drops below 2 cm, due to significant energy deposition outside the sphere. This is consistent with the maximum particle range in tissue for $^{90}$Y (about 11 mm). In this case, for water (liver) density, the MC calculations provide absorbed doses −9.3% (−9.6%), −27.8% (−26.7%), −56.7% (−55.4%) lower than the MIRD analytic approach for tumor diameter of 2 cm, 1 cm and 0.5 cm, respectively (Tables 2 and 3).

TABLE 2

Dose per unit activity calculated with MCNP4C for spherical lesions of different size uniformly filled with $^{90}$Y. The lesions are assumed to have a density of ρ = 1.05 g/cm³ (liver density). The same quantity (dose-per-unit activity) has been calculated using the MIRD analytic approach described by equation (4). The last column of the table (Δ) shows the percentage deviation between the two methods, calculated as $100 \cdot (D_{MCNP} - D_{MIRD})/D_{MIRD}$.

| Lesion diameter | Mass (kg) | Dose/particle (GY/p) | MCNP Gy/GBq | MIRD Gy/GBq | Δ |
|---|---|---|---|---|---|
| 20 cm | 4.40 | $3.38 \cdot 10^{-14}$ | $1.12 \cdot 10^1$ | $1.14 \cdot 10^1$ | −1.8% |
| 10 cm | $5.50 \cdot 10^{-1}$ | $2.68 \cdot 10^{-13}$ | $8.91 \cdot 10^1$ | $9.10 \cdot 10^1$ | −2.1% |
| 8.0 cm | $2.81 \cdot 10^{-1}$ | $5.21 \cdot 10^{-13}$ | $1.73 \cdot 10^2$ | $1.78 \cdot 10^2$ | −2.8% |
| 6.0 cm | $1.19 \cdot 10^{-1}$ | $1.23 \cdot 10^{-12}$ | $4.08 \cdot 10^2$ | $4.21 \cdot 10^2$ | −3.1% |
| 5.0 cm | $6.87 \cdot 10^{-2}$ | $2.11 \cdot 10^{-12}$ | $7.01 \cdot 10^2$ | $7.28 \cdot 10^2$ | −3.7% |
| 4.0 cm | $3.52 \cdot 10^{-2}$ | $4.08 \cdot 10^{-12}$ | $1.36 \cdot 10^3$ | $1.42 \cdot 10^3$ | −4.2% |
| 3.0 cm | $1.47 \cdot 10^{-2}$ | $9.51 \cdot 10^{-12}$ | $3.16 \cdot 10^3$ | $3.34 \cdot 10^3$ | −6.2% |
| 2.0 cm | $4.40 \cdot 10^{-3}$ | $3.09 \cdot 10^{-11}$ | $1.03 \cdot 10^4$ | $1.14 \cdot 10^4$ | −9.6% |
| 1.0 cm | $5.50 \cdot 10^{-4}$ | $2.01 \cdot 10^{-10}$ | $6.67 \cdot 10^4$ | $9.10 \cdot 10^4$ | −26.7% |
| 0.5 cm | $6.87 \cdot 10^{-5}$ | $9.77 \cdot 10^{-10}$ | $3.25 \cdot 10^5$ | $7.28 \cdot 10^5$ | −55.4% |

TABLE 3

Dose per unit activity calculated with MCNP for spherical lesions of different size uniformly filled with $^{90}$Y. The lesions are assumed to have a density of ρ = 1 g/cm³ (water density). The same quantity (dose per unit activity) has been calculated using the MIRD analytic approach described by equation (4). The last column of the table (Δ) shows the percentage deviation between the two methods, calculated as $100 \cdot (D_{MCNP} - D_{MIRD})/D_{MIRD}$.

| Lesion diameter | Mass (kg) | Dose/particle (GY/p) | MCNP Gy/GBq | MIRD Gy/GBq | Δ |
|---|---|---|---|---|---|
| 20 cm | 4.19 | $3.54 \cdot 10^{-14}$ | $1.18 \cdot 10^1$ | $1.18 \cdot 10^1$ | −0.0% |
| 10 cm | $5.23 \cdot 10^{-1}$ | $2.81 \cdot 10^{-13}$ | $9.33 \cdot 10^1$ | $9.44 \cdot 10^1$ | −1.21% |
| 8.0 cm | $2.68 \cdot 10^{-1}$ | $5.47 \cdot 10^{-13}$ | $1.81 \cdot 10^2$ | $1.84 \cdot 10^2$ | −1.5% |
| 6.0 cm | $1.13 \cdot 10^{-1}$ | $1.29 \cdot 10^{-12}$ | $4.27 \cdot 10^2$ | $4.37 \cdot 10^2$ | −2.3% |

TABLE 3-continued

Dose per unit activity calculated with MCNP for spherical lesions of different size uniformly filled with $^{90}$Y. The lesions are assumed to have a density of $\rho = 1$ g/cm$^3$ (water density). The same quantity (dose per unit activity) has been calculated using the MIRD analytic approach described by equation (4). The last column of the table ($\Delta$) shows the percentage deviation between the two methods, calculated as
$100 \cdot (D_{MCNP} - D_{MIRD})/D_{MIRD}$.

| Lesion diameter | Mass (kg) | Dose/particle (GY/p) | MCNP Gy/GBq | MIRD Gy/GBq | $\Delta$ |
|---|---|---|---|---|---|
| 5.0 cm | $6.54 \cdot 10^{-2}$ | $2.20 \cdot 10^{-12}$ | $7.31 \cdot 10^2$ | $7.55 \cdot 10^2$ | $-3.2\%$ |
| 4.0 cm | $3.35 \cdot 10^{-2}$ | $4.27 \cdot 10^{-12}$ | $1.42 \cdot 10^3$ | $1.47 \cdot 10^3$ | $-3.4\%$ |
| 3.0 cm | $1.41 \cdot 10^{-2}$ | $9.95 \cdot 10^{-12}$ | $3.30 \cdot 10^3$ | $3.49 \cdot 10^3$ | $-5.4\%$ |
| 2.0 cm | $4.17 \cdot 10^{-3}$ | $3.22 \cdot 10^{-11}$ | $1.07 \cdot 10^4$ | $1.18 \cdot 10^4$ | $-9.3\%$ |
| 1.0 cm | $5.23 \cdot 10^{-4}$ | $2.05 \cdot 10^{-10}$ | $6.82 \cdot 10^4$ | $9.44 \cdot 10^4$ | $-27.8\%$ |
| 0.5 cm | $6.54 \cdot 10^{-5}$ | $9.86 \cdot 10^{-10}$ | $3.27 \cdot 10^5$ | $7.55 \cdot 10^5$ | $-56.7\%$ |

Dosimetry with $^{90}$Y has received much attention in the past two decades. However, few researchers have addressed the problem of dosimetry in very small liver lesions. The maximum range of $^{90}$Y β-particles is 11 mm in tissue, while average energy β-particles have a range of about 4 mm. It is worth noting that the penetration depth of the high-energy $^{90}$Y β-particles is a critical component of this radionuclide's success in liver radioembolization, allowing for high dose delivery into the tissue between embolized capillaries.

The present work aims to assess the absorbed dose per unit activity in a scenario of percutaneous ablation of HCC through the intratumoral injection of $^{90}$Y in lesions of varying size. A simplified model tumor area was implemented into MCNP4C MC code with the aim to determine the absorbed dose to the lesion when the tumor mass is uniformly filled with $^{90}$Y. Spherical lesions of different size (diameter in the range 0.5-20 cm) were simulated for two different densities: $\rho=1.00$ g/cm$^3$ (water density) and $\rho=1.05$ g/cm$^3$ (liver density). In both scenarios, lesions were assumed to be immersed in a semi-infinite medium with the same density of the lesion. The MIRD analytic approach and MCNP calculations provide results within 10%, no matter the density of the lesion, as long as the lesion diameter exceeds 2 cm. When the lesion diameter drops below 2 cm, significant differences were obtained between MC calculations and the MIRD approach (i.e. deviations>10%). As a general conclusion, the MIRD approach tends to overestimate the absorbed dose in small lesions, as the basic assumption of the model is that β radiation is fully absorbed by the tumor or tissue where the decay occurs. When the radius of the tumor is smaller than the maximum range of the β radiation in the medium, a significant amount of the energy is delivered out of the lesion, thus providing smaller absorbed dose values.

Presently, despite the availability of different dose algorithms, the MIRD analytic algorithm described by equation (4) is still widely used to assess the absorbed dose in tumor and in the liver compartment at the clinical level. For liver lesions that are larger, equation (4) may provide accurate dose estimates (provided that accurate input parameters are introduced, among which the fractional uptake of the target). However, when this approach is applied to assess the absorbed dose to small tumor masses (i.e. approximately below 2 cm diameter) inaccurate dose estimates may be obtained.

In addition, the MIRD analytic algorithm has been safely used for treatment planning with glass microspheres. The foundational principle is based on equation (4), which describes the average dose in a tissue volume as a function of $^{90}$Y activity. During treatment planning, equation (4) can be solved for the treatment activity $A_0$. The results obtained in the present example raise questions as to whether the MIRD analytic approach should be used to assess the prescribed $^{90}$Y activity in order to achieve a given tumoricidal endpoint in small liver lesions. This is especially true when intratumoral injection of $^{90}$Y is performed. For example, for HCC, 120 Gy is typically considered a reasonable minimum target dose. Therefore, when treating an HCC patient with $^{90}$Y β-particles, one may wish to set $D_{tumor}$ to a minimum of 120 Gy. Equation (5) can be rearranged to derive the prescribed treatment activity:

$$A(GBq) = D_{tumor} \cdot m_{tumor}(kg)/49.38(J/GBq) \cdot FU_{tumor}$$

Assuming, for example, a tumor mass, $m_{tumor}$, of 0.52 mg (diameter 1 cm), $FU_{tumor}=1$ and $D_{tumor}=120$ Gy, equation (5) would yield a treatment activity of 1.21 MBq (considering $\rho=1.05$ g/cm$^3$). On the other hand, if equation (7) is used instead of equation (4), a prescribed activity of 1.62 MBq is obtained. As previously outlined, the cause of this difference is a result of a significant energy deposition outside the sphere (about 26% of the β-particles energy is delivered outside the sphere, as reported in FIG. 18A). Consequently, a therapeutic activity of 1.21 MBq would actually correspond to an absorbed dose of about 90 Gy, well below the therapeutic endpoint.

As mentioned, the intratumoral injection of $^{90}$Y is likely to pose specific treatment planning issues related to the possibility of treating very small lesions very selectively. In his paper, Ariel reported the first interstitial use of $^{90}$Y microspheres for the treatment of a rhabdomyosarcoma (Ariel I 1978 *Cure of an embryonal rhabdomyosarcoma of the nose of an infant by interstitial $^{90}$Yttrium microspheres: A case report International Journal of Nuclear Medicine and Biology* 5 37-41). A nodule measuring 1.5 cm in diameter was successfully treated with interstitial injection of 185 MBq of microspheres. In another study (Tian J H, Xu B X, Zhang J M, Dong B W, Liang P, Wang X D 1996 *Ultrasound-guided internal radiotherapy using yttrium-90-glass microspheres for liver malignancies Journal of Nuclear Medicine* 37 958-63), $^{90}$Y-glass microspheres were injected into predetermined tumor sites using an ultrasound-guided procedure. Tumor size ranged from 1.9 to 8.8 cm, with most lesions being less than 5 cm in diameter. More recently, Ferrari and co-workers assessed the absorbed doses to small-volume brain neocavities and surrounding tissues after local $^{90}$Y-DOTATOC injection (Ferrari M, Cremonesi M, Bartolomei M, Bodei L, Chinol M, Fiorenza M, Tosi G, Paganelli G. *Dosimetric model for locoregional treatments of brain tumors with $^{90}$Y-conjugates: clinical application with $^{90}$Y-DOTATOC, J Nucl Med.* 2006 January; 47(1):105-

12.). A recent review of the literature on the intratumoral treatment with radioactive beta-emitting microparticles can be found in Bakker R, Lam M, van Nimwegen S, Rosenberg A, van Es R and Nisen J 2017 *Intratumoral treatment with radioactive beta-emitting microparticles: a systematic review Journal of Radiation Oncology* 6 323-341.

Described herein is a procedure whereby microspheres are delivered to the target using a direct, image-guided intratumoral injection of $^{90}Y$ microspheres (embedded in a biocompatible matrix) using a delivery system as described herein. This procedure is also known as percutaneous radioablation and is a minimally invasive treatment for patients with small (below approximately 3 cm) liver tumors performed using a combination of the following components: i) BIOGLUE® (Cryolife, Atlanta, US), a FDA-approved mixture of bovine serum albumin and glutaraldehyde in a 4:1 ratio, approved for use in soft tissue repair or to seal damaged parenchyma ii) SIR-SPHERES® coated with $^{90}Y$ (Sirtex Medical, Sydney, Australia) approved for implantation into hepatic tumors via the hepatic artery and the iii) MIPP-KIT® (Svas Biosana, Naples, Italy) a dedicated coaxial dual-lumen catheter for the direct, imaging-guided intra-tumoral injection of the glue and $^{90}Y$ microsphere mixture. The evidence from this study suggests that caution must be taken when planning the treatment of very small lesions with $^{90}Y$, implementing the standard analytic approach. This is particularly true when intratumoral administration of $^{90}Y$ is performed, as this approach allows sub-centimeters tumors to be selectively treated. In such a scenario, the use of the analytic approach to calculate the therapeutic activity needed to achieve a given tumoricidal endpoint may result in important dose underestimations.

In some embodiments, the alternative algorithm presented by equation (7) can be usefully employed in treatment planning for intratumoral injection of microspheres, providing results in close agreement with Monte Carlo calculations (maximum deviation below 0.5%).

In conclusion, for a given activity $A_0$, the analytic equation proposed by the MIRD model (equation 4) is likely to overestimate the absorbed dose in lesions below 2 cm. Conversely, activity underestimations can be obtained if the analytic approach is used to assess the prescribed $^{90}Y$ activity. This is because the basic assumption made to derive equation (4) (full absorption of the β particle into the target volume) is no longer true for small lesions. However, overestimations are below 10% for lesions with a diameter larger than approximately 2 cm. As a rule, the larger the lesion size, the better the agreement of the MIRD model with Monte Carlo calculations. When the lesion size drops below 2 cm the two calculation approaches deviate significantly, with the analytic algorithm providing dose overestimations up to 57% (for lesions of 0.5 cm diameter). Therefore, caution is advised when using equation (4) for absorbed dose determination in very small lesions. In particular, for the assessment of the absorbed dose in small tumor regions the use of equation (7) is suggested instead of equation (4).

Example 1: Pre-Clinical Study

Figure 2B:
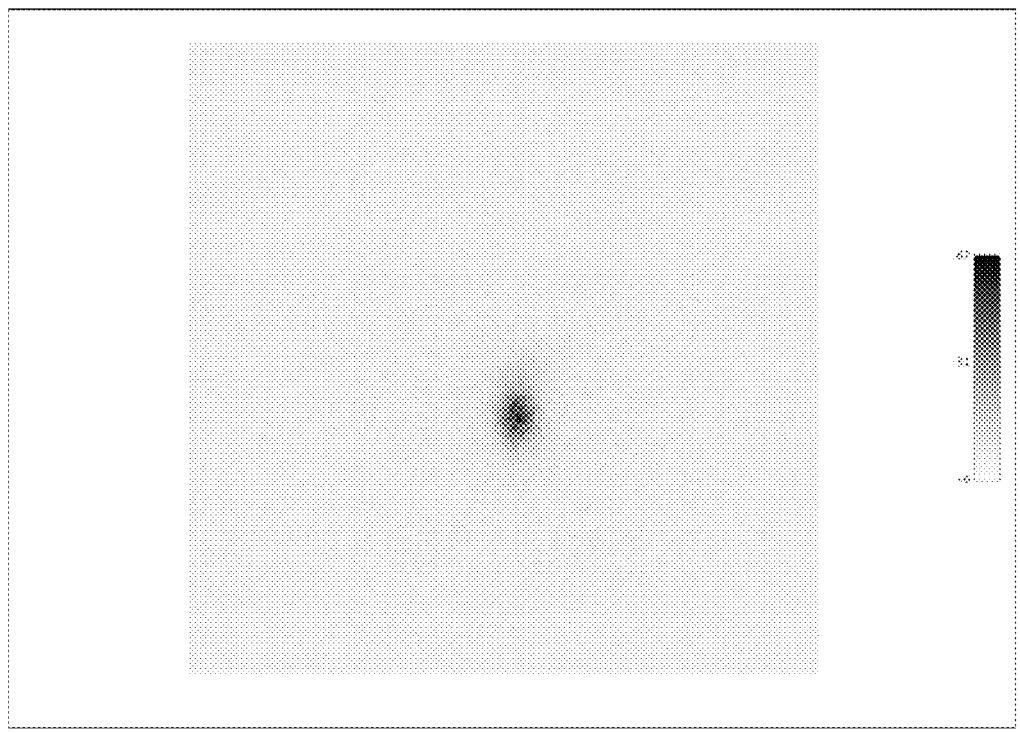
Figure 3A:
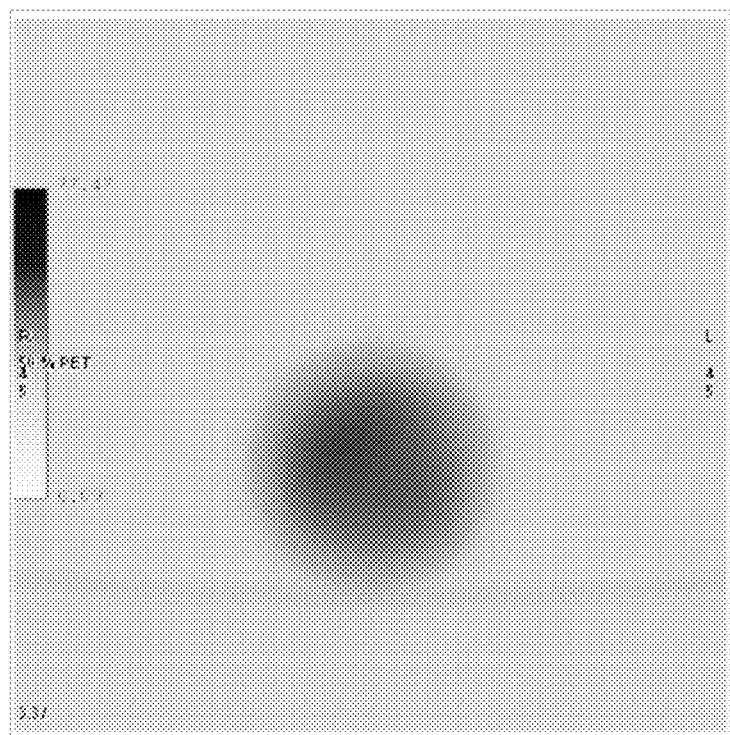
FIGS. 3A and 3B are PET/CT and CT scans, respectively, of a radiogel loaded in a plastic sphere.
Figure 3B:
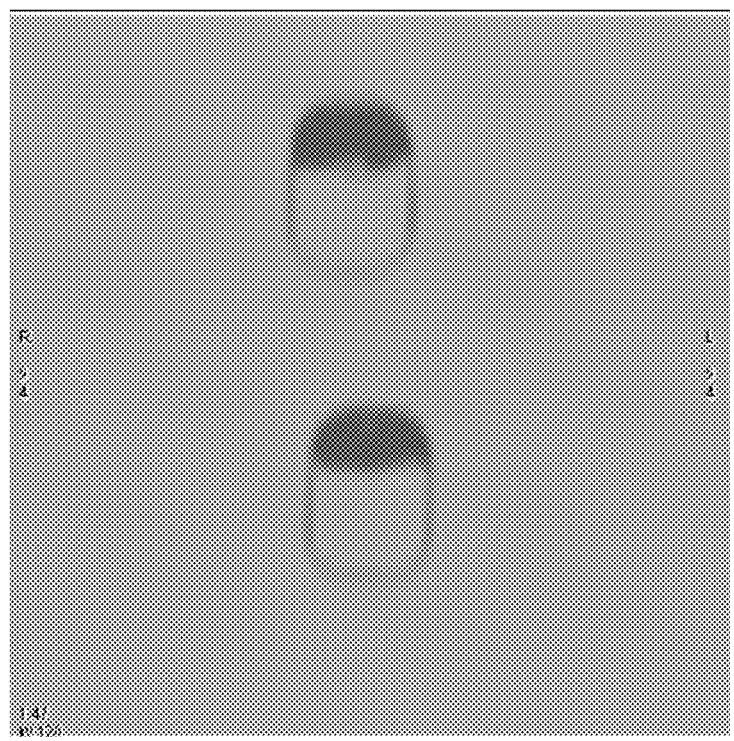

In one example, a homogeneous distribution of $^{90}Y$-labelled particles is demonstrated in a set of experiments using $^{90}Y$ microspheres mixed with a hydrogel or tissue glue. By solidifying during the injection or implantation process, the radioactive glue or gel can be distributed uniformly, and it can resist undesired effects from gravity, dispersion or leakage into the blood or lymph vessels, hematomas, etc. FIGS. 2A and 2B depict gamma camera views of 1mCi (37 MBq) of $^{90}Y$ microspheres in BIOGLUE®, which is a mixture of 45% wt/vol bovine serum albumin and 10% wt/vol glutaraldehyde, in a 4:1 ratio in a 2.5 mL syringe cylinder. Additional studies were performed using 5 mL plastic spheres which were filled with $^{90}Y$ microspheres and a gel carrier or matrix material, such as BIOGLUE, COSEAL (PEG/HCl/NaPhos/NaCO$_3$; Baxter Healthcare, Hayward, Calif.) or BERIPLAST (fibrinogen/thrombin; CSL Behring GmbH; Marburg, German), at activity levels in the range of 370 to 740 MBq, filled using a dual-lumen coaxial catheter. In these studies, gamma camera and PET/CT imaging was performed using 4 mm slices to more precisely assess the distribution of radioactivity in the solidified carrier, as shown in FIGS. 3A and 3B. The PET/CT imaging in FIG. 3A also demonstrated that there was no separation of the liquid used to suspend the microspheres in the solid carrier material in the cavities after mixing, and that there were no changes in the homogenous distribution or other changes to the solidification process within the cavities at the larger sizes.

Figure 4A:
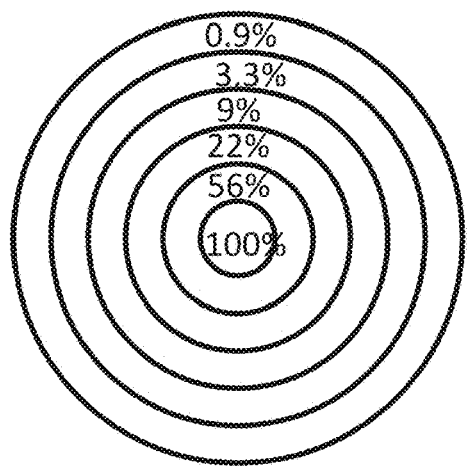
FIGS. 4A to 4C depict the absorbed doses of 0.5 mL, 4.2 mL and 11.4 mL volumes, respectively, filled with a $^{90}$Y-matrix composition.
Figure 4B:
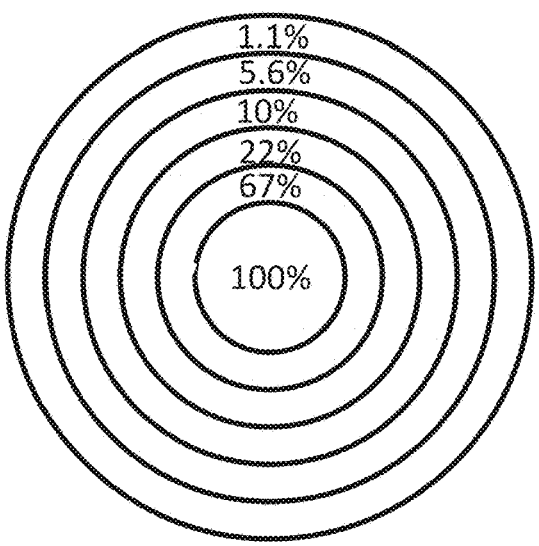
Figure 4C:
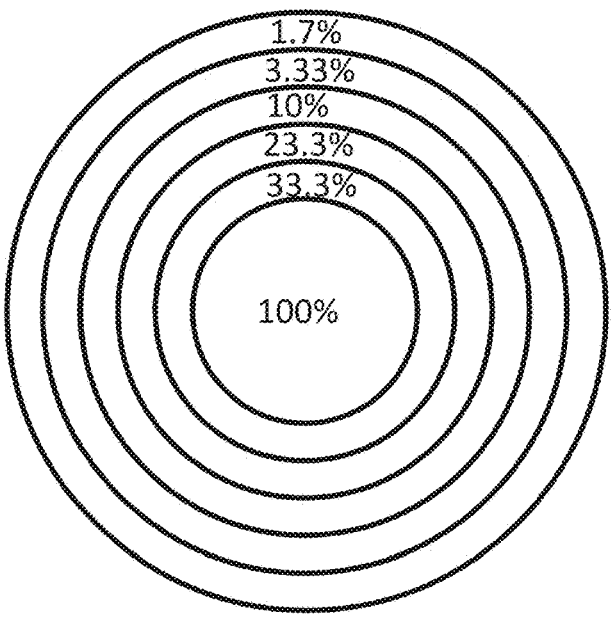

The use of the gamma camera and PET/CT imaging was also used to evaluate the dosimetry distribution of the $^{90}Y$ microspheres and solidified matrix. FIGS. 4A to 4C depict the relative absorbed doses in cavities of 0.5 mL, 4.2 mL and 11.4 mL spherical volumes (0.5 cm, 1 cm and 1.5 cm radii, respectively), as measured from the center of each corresponding volume and shell volumes 1 mm thick from the sphere surface.

Figure 5:
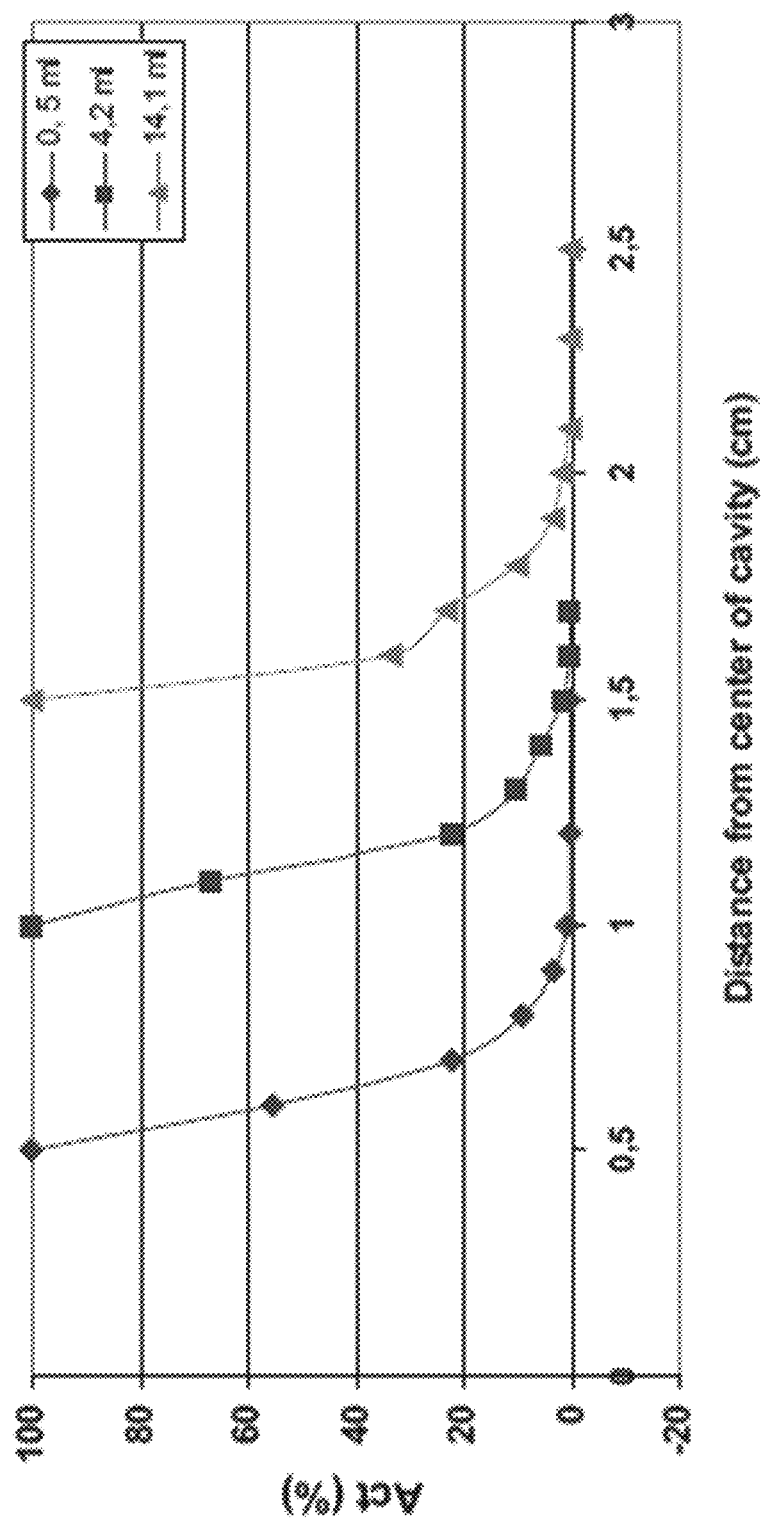
FIG. 5 is a graphical plot of the percentage activity per distance from the center of the three cavities in FIGS. 4A to 4C.

FIG. 5 depicts the percent activity of the $^{90}Y$ microsphere-BIOGLUE® composition in each of the volumes described hereabove in FIGS. 4A to 4C. For each of the 0.5, 1 cm and 1.5 cm radii volumes, the percentage of activity effectively falls to less than 50% activity within a 0.5 cm distance of the radius from the volume surface, or within a 150% radius distance from the center of the volume. For the 0.5 cm radius volume, the percentage activity falls to less than 10% or 5% within 0.5 cm from its surface and to zero within 1 cm of its surface, or 1 cm from its center and 1.5 cm from its center, respectively. For the 1 cm radius volume, the percentage activity falls to less than 10% or 5% within 0.5 cm from its surface and to less than 1% within 1 cm from its surface, or 1.5 cm from its center and 2 cm from its center, respectively. For the 1.5 cm radius volume, the percentage activity falls to less than 10% or 5% within 0.5 cm from its surface and to less than 1% within 1 cm from its surface, or 2 cm from its center and 2.5 cm from its center, respectively. The estimated absorbed doses for these volumes are provided below:

0.5 mL volume with 0.5 cm radius and activity of 185 MBq:

| Distance from Center (cm) | Gy/MBq | Gy |
|---|---|---|
| 0.5 | 62.9 | 11640 |
| 0.6 | 35.0 | 6467 |
| 0.7 | 14.0 | 2587 |
| 0.8 | 5.6 | 1035 |
| 0.9 | 2.1 | 388 |
| 1 | 0.559 | 103 |
| 1.2 | 0.070 | 13 |
| 1.5 | 0.0002 | 0.04 |

4.2 mL volume with 1 cm radius and activity of 370 MBq:

| Distance from Center (cm) | Gy/MBq | Gy |
|---|---|---|
| 1 | 10.1 | 3732.3 |
| 1.1 | 6.7 | 2488.2 |
| 1.2 | 2.2 | 829.4 |
| 1.3 | 1.0 | 373.2 |
| 1.4 | 0.6 | 207.4 |
| 1.5 | 0.112 | 41.5 |
| 1.6 | 0.004 | 1.7 |
| 1.7 | 0.001 | 0.4 |

14.1 mL volume with 1.5 cm radius and activity of 1110 MBq:

| Distance from Center (cm) | Gy/MBq | Gy |
|---|---|---|
| 1.5 | 3.46 | 3843.2 |
| 1.6 | 1.15 | 1281.1 |
| 1.7 | 0.81 | 896.7 |
| 1.8 | 0.35 | 384.3 |
| 1.9 | 0.12 | 128.1 |
| 2 | 0.06 | 64.1 |
| 2.1 | 0.0092 | 10.2 |
| 2.3 | 0.0012 | 1.3 |

Figure 6:
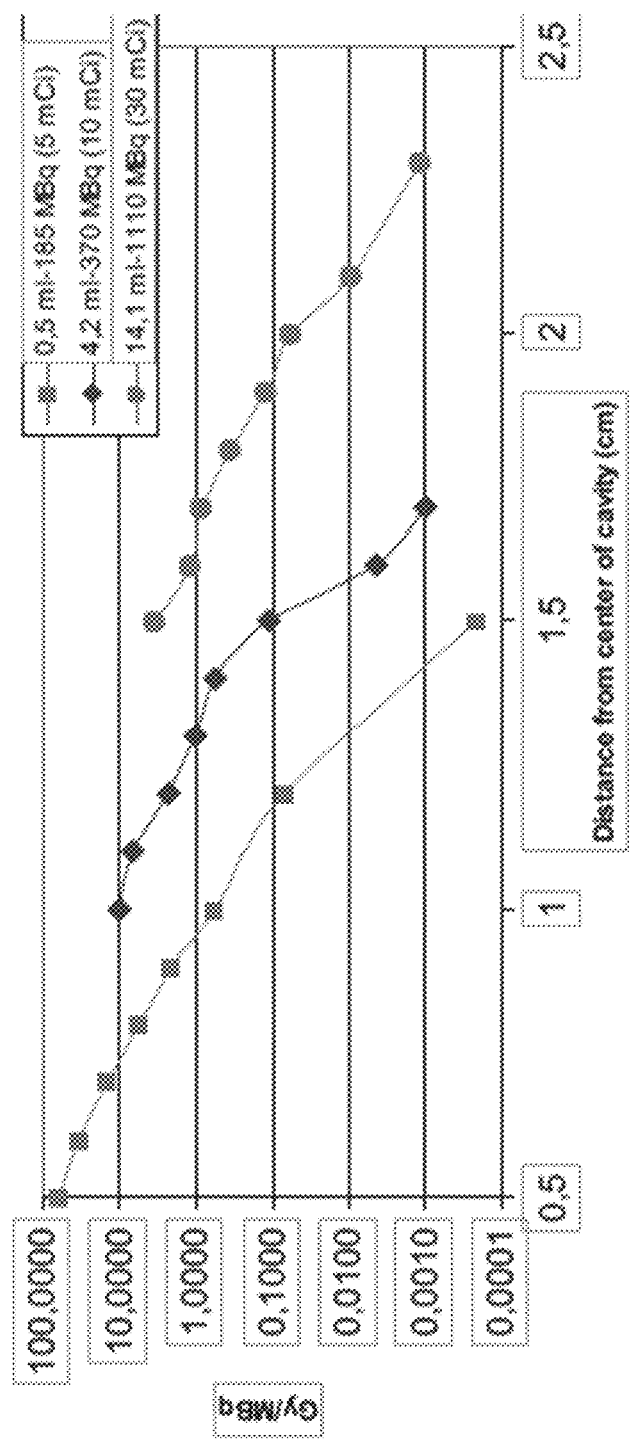
FIG. 6 is a graphical plot of the estimated Grays per MBq per distance from the center of the three cavities in FIGS. 4A to 4C.

FIG. 6 depicts the absorbed dose per unit (Gy/MBq) in adjacent shell volumes for the three volumes. These plots show that there is a decrease of at least 95%, or 1 to 2 orders of magnitude decrease in the absorbed dose within a 0.5 cm distance from the surface of the volume, and at least a 90% decrease within 150% of the radius.

Figure 7:
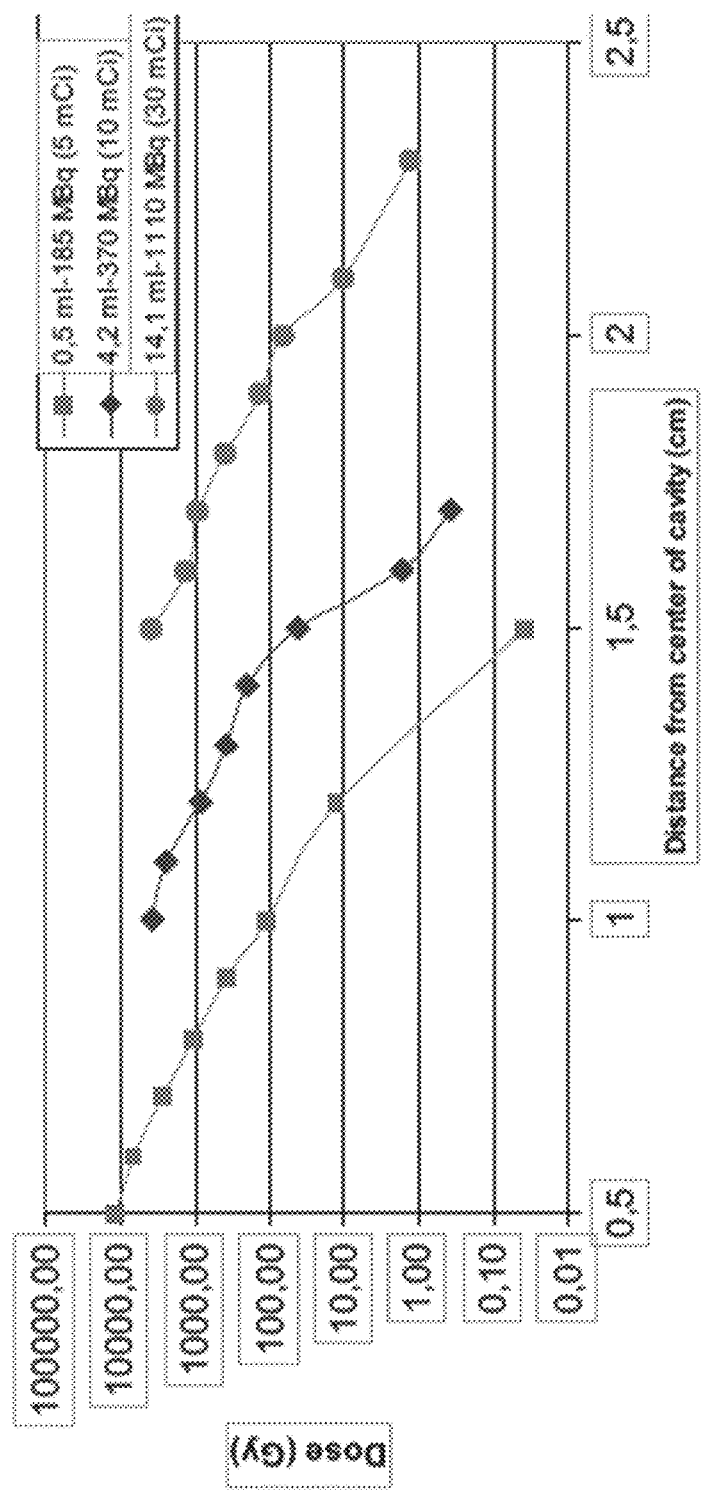
FIG. 7 is a graphical plot of the estimated total absorbed dose per distance from the center of the three cavities in FIGS. 4A to 4C.

FIG. 7 depicts the total absorbed dose in Grays in adjacent shell volumes for the three volumes. For the 0.5 cm radius volume, the absorbed dose within 0.5 cm from the surface (1 cm from the center) decreases by about 90%. For the 1 cm radius volume, the absorbed dose within 0.5 cm from the surface (1.5 cm from the center) decreases by more than 90%. For the 1.5 cm radius volume, the absorbed dose within 0.5 cm from the surface (2 cm from the center) decreases by more than 90%.

Example 2: Mice Study

In one study, an animal model of pancreatic cancer applicant used with human MIA-Paca-2 RFP cells in the thigh of CD1 nude mice to then apply the new matrix, which will act as a carrier for the $^{90}Y$ spheres, in the site of the induced tumor. Intra-tumoral application of the new matrix with $^{90}Y$ spheres led to increased levels of the compound in the tissues through its homogeneous distribution and made it possible to achieve effective doses for the treatment of the tumor by reducing the rate of spreading and avoiding and minimizing the systemic side effects of therapy.

The experimental protocol involved a locoregional treatment affecting tumor shrinkage with tangible benefits for the host. The results obtained from this and other studies herein can be translated into clinical practice, introducing significant benefits, as in the majority of cases pancreatic cancer is inoperable for locally advanced disease.

The radioisotope and matrix used for this study were the SIR-SPHERES® and the BIOGLUE® as described above. It is believed that the composition:
- can be administered intra-tumorally in order to cause complete necrosis of the tumor tissue surrounding the injection site, thus allowing the treatment of malignant tumor masses which cannot be surgically removed;
- can be applied as a coating or filling material for surgical wounds, following surgical resection or ablative treatments of malignant tumor masses in order to cause complete necrosis of any remaining tumor cells localized along the edges of these wounds;
- can lead to the increased efficacy of anticancer substances, producing a beneficial increase in the administration and dosing times of said substances at a local level, through increased concentration of the substances inside the treated tumor masses, or inside surgical wounds from surgical removal, or ablative treatments, of tumors;
- prevents anticancer substances from freely dispersing in the patient's body, thereby limiting systemic exposure to their toxic components; and/or
- avoids some of the side effects from application of methods of treatment alternative to surgical resection of malignant tumor masses.

It is believed that the radioisotope-matrix composition including a substance with adequate anticancer capacity, such as $^{90}Y$ or other similar type to Holmium, in a suitable viscous material capable of entrapping the microspheres, may provide homogenous distribution and act as a carrier of said substance. Necrosis of the tumor cells of interest is induced by adequate internal electron radiotherapy (IER) determined by localized emission of radioactive particles by the above-mentioned microspheres radiolabeled with $^{90}Y$. Through gamma camera and PET/CT/SPECT imaging studies, depicted in FIGS. 8A to 8F, it was found that the $^{90}Y$ is dispersed in an almost homogeneous manner inside the tumor mass into which it is injected or inside the surgical wound on which it is applied, on account of the viscous nature of the components forming the matrix, and that this homogeneous distribution is highly instrumental in the necrosis of the tumor cells located in these areas.

Figures 8D, 8E, 8F:
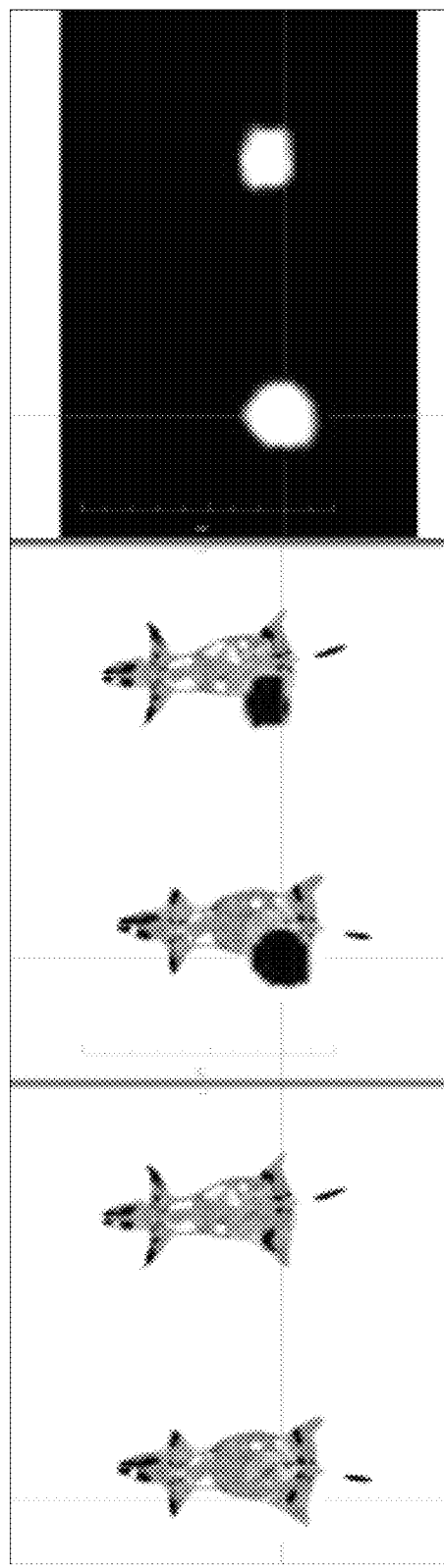
FIG. 8D are transverse CT views of another mouse with a thigh tumor, FIG. 8E are composite transverse CT/PET/SPECT views of the mouse in FIG. 8D depicting tumor activity.
FIG. 8F are the PET/SPECT image components from FIG. 8E.

Tumors were induced in mice following injection of the human MIA-Paca-2 RFP cells. FIGS. 8A and 8D depict PET/SPECT images of the matrix that did not contain any $^{90}Y$ spheres, while FIGS. 8B and 8E depict PET images of the mice injected with the combined $^{90}Y$-matrix composition. FIGS. 8C and 8F are corresponding SPECT images of the mice in FIGS. 8B and 8D, confirming that none of the $^{90}Y$ spheres had leaked or dispersed from the injection site, and that there is a homogenous distribution of the radioisotope within the tumor.

The results also show that, by using a hydrogel or matrix with a sufficient solidification rate as a carrier for the radiolabeled-microspheres, the possible dispersion of said microspheres in the patient's body potentially caused by factors such as gravity, circulation in the blood and/or lymphatic vessels, the presence of hematomas, etc. may be substantially limited, thus avoiding or greatly reducing possible side effects from potential leakage of the radioactive material in the patient.

The material forming the hydrogel or matrix is a viscous gel or matrix designed for direct intra-tumoral injection or for application of a surface of a tumor resection site. This matrix is configured to contain the $^{90}Y$ spheres, which, on account of their size and composition, (e.g. resin or glass), are trapped in the gel matrix and thus localized at the tumor or resection site for an extended period of time in order to increase or maximize the local dose level and duration of exposure. The overall effect of the matrix with $^{90}Y$ microspheres results in an increase in local $^{90}$Y microspheres concentrations, limiting or reducing peak systemic exposure.

Example 3: Matrix-Injector Development

Due to the different densities and viscosities of the two solutions forming a hemostatic gel, sealant or hydrogel, one solution may flow into the catheter in greater quantity than the other, whereby the following problems may occur:
  compound wastage;
  difficulty applying the compound on account of the considerable force the operator has to apply to the syringe with both hands;
  misapplication of the compound due to dislodgement of the end portion of the catheter because the operator is unable to use just one hand to hold said catheter in place during infusion; such dislodgement requires the operator to use a greater quantity of the compound in order to be sure that it has reached and covered the entire the target volume.

Moreover, the reduced flow rate of either of the two compounds facilitates activation of the compound near the end portion of the catheter where mixing takes place to activate the compound, i.e., near the outlet of the two substances, which causes the obstruction of said catheter, thus causing the operator to apply more force in order to overcome the resistance of the two solutions to the infusion. In addition, the greater the force required of the operator, the more difficult it is to hold the end portion of the catheter near the target in place; this involves the need to perform continuous ultrasound or X-ray monitoring of the correct positioning of the catheter and any repositioning that may be required.

Due to these potential problems, and until now, the various glues and matrices have only been used intraoperatively. Further there have been great difficulties with percutaneous administration or during laparoscopy due to the use of double-lumen catheters which are designed and developed for other purposes and are unable to convey the two solutions to the area concerned at the same time, resulting in obvious wastage of compounds or drugs and poor therapeutic results.

Therefore, the technical issue consists of ensuring that the two solutions with different viscosities and densities have the same flow rate, meaning that they must flow in and out from the distal end or outlet of the catheter at the same time.

Thus, it is beneficial to deliver a combination of a carrier matrix and $^{90}$Y-loaded microspheres with a device capable of transporting the compound to the target area in the desired ratio, and while preferably avoiding all the disadvantages existing thus far both in the case of percutaneous image-guided treatments and laparoscopic and intraoperative treatments.

In one example, a double-lumen catheter was developed for the infusion of a two-component compound, particularly for glues or agents containing thrombin and fibrinogen. The catheter comprises a first lumen intended for a first solution of a first component and a second lumen intended for a second solution of a second component. Said lumens respectively form, as per a catheter cross-section, a first area and a second area, with the ratio of said areas being proportional to the viscosity ratio of the respective fluids. According to a further aspect of the invention, it is preferable for said ratio of said areas to be greater than the square root of the ratio of the viscosities of the fluids passing through the respective lumens.

In particular, it is preferable for said ratio of said areas to be approximately equal to the square of the ratio of the viscosities of the fluids passing through the respective lumens. Said ratio value takes another aspect into account, namely that the viscosity varies according to the temperature.

Figure 9A:
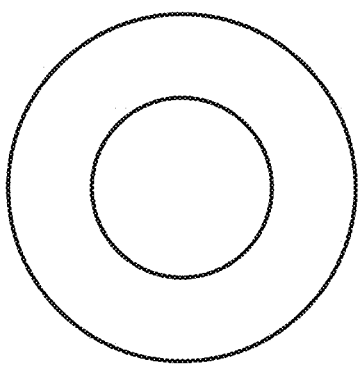
FIG. 9A is a schematic cross-sectional view of a dual-lumen catheter shaft with concentric lumens.

In some examples, the lumens have a circular cross section and are concentric, and that the first lumen incorporates the second lumen, as depicted in FIG. 9A. In this case, it is preferable for the first lumen to be configured and sized so as to receive the higher viscosity solution so that said solution might be more exposed to warming induced by contact of the catheter with the patient's tissues during infusion.

Therefore, the variant of the catheter allowing for better use of the penetration of warmth coming from outside requires the two lumens to have a circular cross-section and to be concentric and for the higher viscosity solution to flow in the outer lumen and therefore the outer lumen to have a larger cross-section than the inner lumen.

The catheter described above is applied in the medical/clinical field in minimally invasive percutaneous procedures, surgical, laparoscopic or interventional radiology procedures whenever necessary to administer the anticancer compound.

As a result of the present invention, it becomes possible to ensure that the two solutions have the same flow rate and so move along the catheter at the same time, i.e. exit the catheter in equal amounts so as to ensure the correct activation of the agent when infused in proximity to the patient's target tissues. As an advantage, it is possible to minimize infusion times and the amount of effort the operator is required to use during the infusion and it is also possible to minimize the quantities of the compound injected.

The features of a catheter according to the present invention prove to be very surprising because a technician in the field would have clearly applied Poiseuille's law, which states that the motion at constant speed of a viscous and incompressible fluid in a pipe having a constant cross section is laminar, i.e., consists of the relative sliding of an infinite number of cylinders coaxial to the tube axis.

Consequently, a pressure variation $\Delta p$ between two points located respectively at the inlet and outlet of the tube is given by:

$$\Delta p = \frac{8\eta L}{\pi r^4} Q_v$$

Where L is the length of the tube, r is the diameter of the tube, $Q_v$ is the flow rate of the viscous fluid in the tube and $\eta$ is the viscosity of the fluid.

Since it is required for the two solutions to have the same flow rate and the same pressure variation along the catheter in order to minimize the effort applied by the operator on the body of the dual-chamber syringe, therefore:

$$\frac{\eta_1}{\pi \cdot r_1^4} = \frac{\eta_2}{\eta \cdot r_1^4},$$

or $$\frac{\eta_1}{S_1^2} = \frac{S_1^2}{S_2^2}, \text{ therefore } \frac{\eta_1}{\eta_2} = \frac{S_1^2}{S_2^2}$$

Where $S_1$ and $S_2$ respectively represent the lumen cross-section areas. In other words, by applying Poiseuille's law, the result should be for the ratio of the cross sections of the two lumens to be proportional to the square root of the ratio of the respective viscosities.

To be more precise, the present invention stipulates a preferred proportion between the ratios of the areas and the ratios of the cross-sections, expressed using the following formula, which seems to go against the predicted said law of physics:

$$\frac{\eta_1^2}{\eta_2^2} = \frac{S_1}{S_2}$$

In fact, said law of physics is unable to contemplate the behavior of the two solutions forming the hemostatic agent when the temperature varies and particularly when the catheter is inserted in the patient's body. In fact, under said circumstances, the temperature of the two solutions varies from an ambient temperature of approximately 18° C. to approximately 37° C., the temperature of the human body.

Figure 9B:
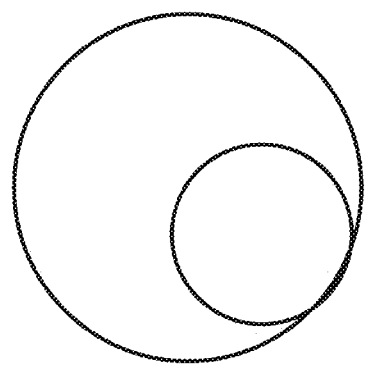
FIG. 9B is a schematic cross-sectional view of a dual-lumen catheter shaft with eccentric lumens.
Figure 9C:
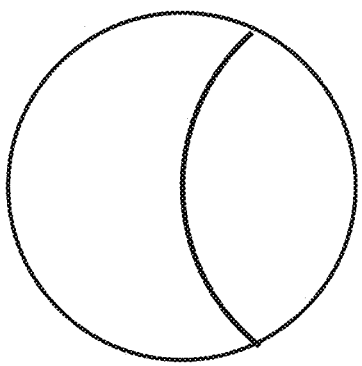
FIG. 9C is a schematic cross-sectional view of a dual-lumen catheter shaft with an arcuate septum between the two lumens.
Figure 9D:
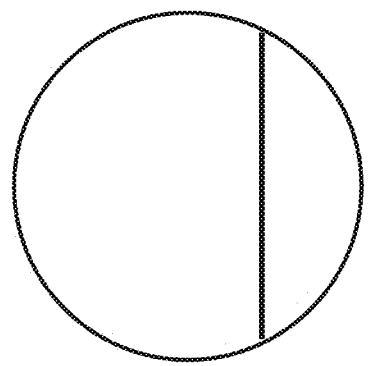
FIG. 9D is a is a schematic cross-sectional view of a dual-lumen catheter shaft with a straight septum between the two lumens.

Variations of the formula described above may be made in order to contemplate different positions of the inner lumen in relation to the outer lumen, for example with the axes of the lumens coincident (FIG. 9A), not coincident but parallel (FIG. 9B), or with the two lumens divided by a curved or straight septum (FIGS. 9C and 9D, respectively).

However, in some variations, the properties of the catheter are obtained according to the following relation, when the ratio between the areas of the lumen cross-sections is slightly greater than the square root of the ratio of the respective viscosities:

$$\sqrt{\frac{\eta_1}{\eta_2}} < \frac{S_1}{S_2}$$

One embodiment has an external diameter of 16G, corresponding to an external diameter of approximately 1.6 mm. In addition, the two lumens are concentric, therefore:
the first lumen has a diameter of 0.022 inches, i.e. 0.56 mm
the second lumen has a diameter of 0.010 inches, i.e. 0.25 mm Therefore, the cross-sectional area of the second lumen is $\pi \times 0.125^2 = 0.04906$ mm$^2$, the gross area of the first lumen is $\pi \times 0.28^2 = 0.24617$ mm$^2$, while the net area is $0.24617 - 0.04906 = 0.19711$ mm$^2$. This means that the ratio between the areas of the first and second lumen is approximately 4; therefore, it is suitable for solutions with a viscosity ratio of approximately the square root of 4, i.e. approximately 2. Externally, other embodiments of the catheter may have a standardized cross-section, for example 20G, 18G, 16G, or 14G.

Preferably, the catheter is made of a radiopaque material that is visible during x-rays and/or other imaging modalities. A length compatible with its use is approximately 20 cm and it is preferable for said material to make it semi-rigid, but in other examples may be flexible or rigid. Preferably, it comprises a rigid connector that can be connected to special syringes for injecting the two-component compound. In other examples, the catheter may have a shaft length in the range of 10 cm to 100 cm, about 20 cm to 70 cm, or 30 cm to 60 cm. It may comprise a rigid Y-connector specific to the two components, with a Luer-lock end connector that is a standard connector. Lastly, it is preferable for the catheter body to have specific markings at a set distance apart, for example at a distance of one centimeter apart, i.e. divided into centimeters for at least part of the catheter.

The kit may further comprise an introducer the same length as the catheter, for example 20 cm, and a cross-section compatible with one of the possible cross-sections of the catheter. In some variations, the distal tip of the catheter may be flush with the distal tip of the introducer. In other examples, the catheter tip may extend out or be spaced proximally from the distal end of the introducer by 1 mm to 10 mm, or 1 mm to 5 mm, or 2 mm to 4 mm. The introducer may also be divided into centimeters, i.e. markings a set distance apart and made of radiopaque material. Furthermore, it may have a removable steel core with a sharp tip slightly longer than the introducer, for example, 210 mm long, and may include a Luer-lock connector. The preferred material for the body of the catheter is GRILFLEX® ELG 6260 (PEBA). Lastly, the catheter ends with an orthogonal cut along the axis.

Figure 10A:
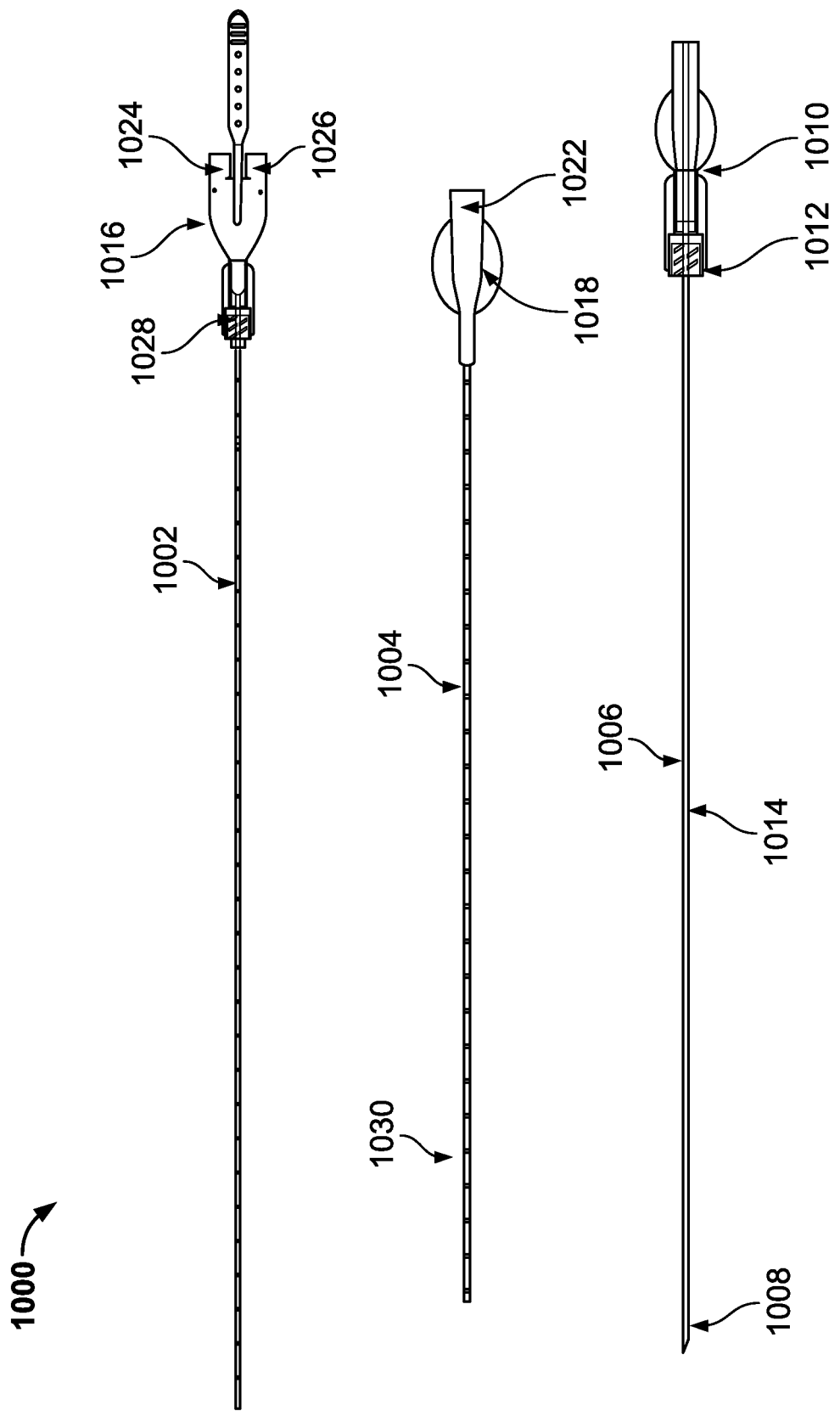
FIG. 10A is a photograph of another example of a dual-lumen catheter delivery kit.

FIG. 10A is a photograph of another exemplary kit 1000 that may be used for delivery of the $^{90}$Y-matrix composition, comprising a catheter 1002, an introducer 1004, an introducer core (not shown), and a needle 1006. To perform the procedure, the introducer 1004 together with its core is positioned using ultrasound, CT or MR imaging guidance. After removing the core of the introducer 1004, the needle 1006 is inserted through the introducer 1004. Any biopsy or other ablation procedure may be performed through the needle 1006. After the diagnostic and/or therapeutic procedure is performed, the needle 1006 is removed and the catheter 1002 is inserted into the introducer 1004 and the multi-chamber sealant injector (not shown) is attached to the catheter 1002. The sealant is then injected along the tissue tract as the combined injector and catheter are withdrawn from the tissue tract.

The distal end 1008 of the needle 1006 has a sharp, beveled tip and is preferably visible on ultrasound. For example, a cross-section of the needle could be 16G, that is, equivalent to an outer diameter of 1.60 mm and an inner diameter of 1.20 mm, made of AISI 304 with the tip being visible on ultrasound. The proximal hub 1010 of the needle 1006 may have an attached Luer-lock distal connector 1012, for example, comprising transparent ABS TERLUX® TR2812. The preferred length of the needle shaft 1014 is 200 mm, and shaft 1014 is configured to be inserted into the introducer 1004. The introducer 1004 may comprise a GRILAMID® L25 shaft, with an optional tapered distal tip. The inner diameter of the introducer 1004 is approximately 1.70 mm, while the length of the introducer 1004 should be preferably slightly longer than the needle 1006, e.g. 210 mm, or a length that is 1 mm to 20 mm, 5 mm to 10 mm, or 5 mm to 15 mm longer than the needle 1006. In other examples, the inner diameter of the introducer may be in the range of 0.8 mm to 2.2 mm, or 1 mm to 2.2 mm, or otherwise to accept a catheter or needle shaft with a size from 12G to 18G.

Figure 10B:
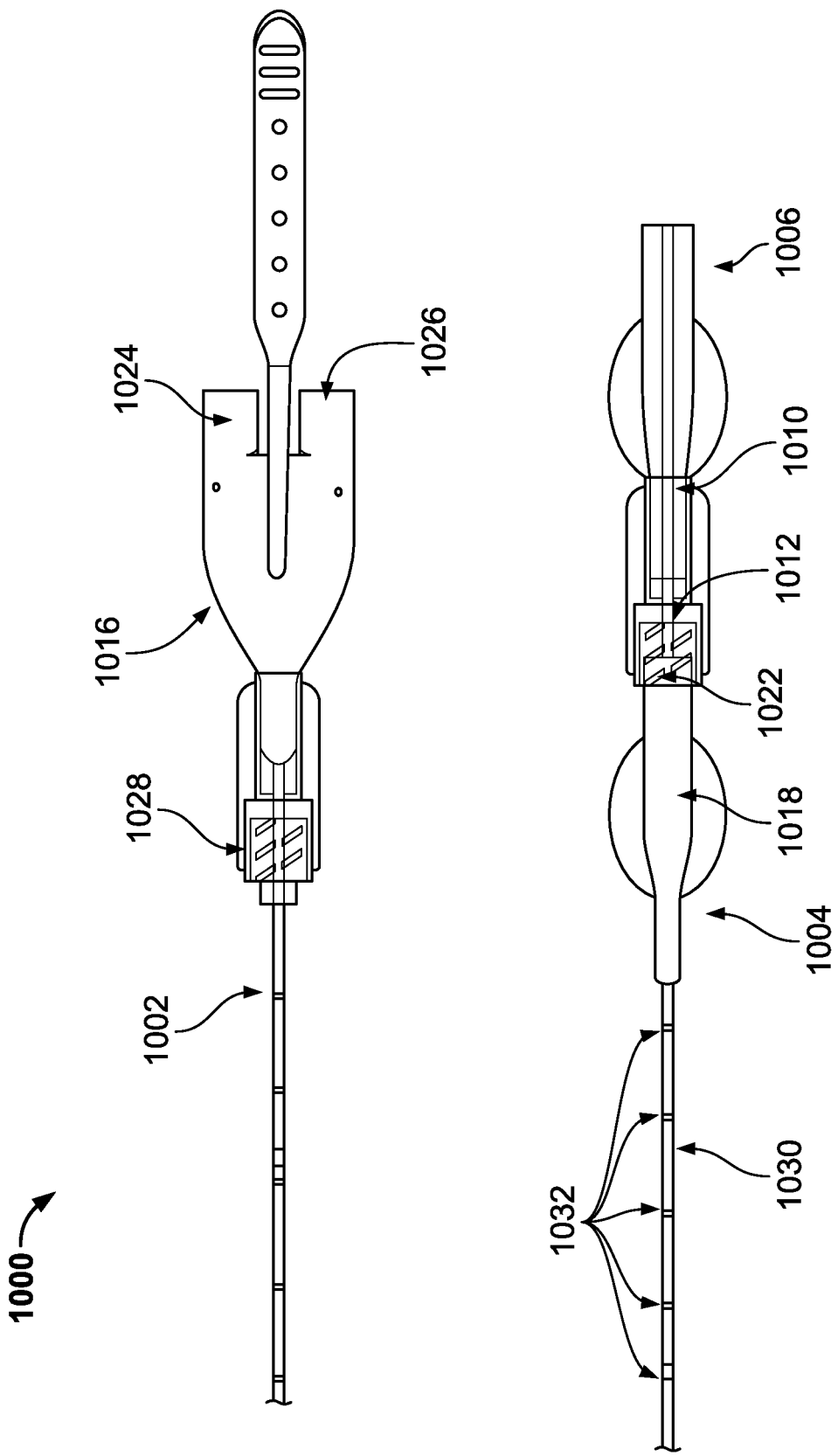
FIG. 10B is a close-up photograph of the proximal end of the catheter and the combined introducer and stylet.

FIG. 10B is a close-up photograph of the proximal hubs 1016, 1018, 1010 of the catheter 1002, introducer 1004, and needle 1006, respectively, with needle 1006 inserted into the introducer 1004 such that the proximal needle hub 1010 is engaged to the proximal introducer hub 1018 via complementary Luer locks 1012, 1022. The proximal hub 1016 of the catheter 1002 comprises two ports 1024, 1026 that are configured to attach to dual tips of a dual-chamber syringe (not shown). FIGS. 10C and 10D depict longitudinal cross-sections of the catheter 1002 with a male Luer-lock connector 1028 compatible with a female Luer-lock connector 1022 of the introducer 1004, respectively. This configuration permits both the needle 1006 and the catheter 1002 to be releasably locked to the introducer 1004 when inserted into the introducer 1004. The introducer 1004 may comprise a shaft 1030 with distance markings 1032 visible along its longitudinal length, and wherein the shaft 1030 is preferably radiopaque, e.g., loaded with 30% barium sulfate and inserted into a protective polythene tube. The catheter 1002 and introducer 1004 are also depicted with optional handles 1034, 1036 to facilitate handling during use.

Before a minimally invasive treatment takes place, the kit is prepared so that the introducer is inserted first, with the diameter corresponding to the catheter chosen according to the procedure to be performed, and it will be placed under ultrasound guidance, CT or MRI scanning. Once the core of the introducer is removed, the coaxial double-lumen catheter is then inserted and the compound is administered as needed, in order to fill the treatment area and if necessary the distance covered by the introducer, which is then slowly removed in order to release the compound including along the course of the introducer. This ensures effective functioning, ease of administration, conservation of drugs, and avoiding of additional invasive procedures for externally conveying the anticancer agent. The elements and features described above, in their various preferred embodiments, may be combined without departing from the scope.

Example 4: Pig Study

In another animal study, eight large white female pigs weighing 75±5 kg, selected from special farms, free of infection and previously immunized, underwent injection of bioglue-$^{90}$Y microspheres under ultrasound guidance of three different liver segments or lobes. For these procedures, 24 ml of glutaraldehyde crosslinked albumin (BIOGLUE®) containing 60/80mCi of $^{90}$Y microspheres was used in the left lobe, the right lobe, and the right lower paracaval lobe. The veterinarian examined all animals in order to assess their state of health and the absence of symptoms related to any disease and then underwent eight-hour preoperative fasting, anesthesia, and blood sampling. Blood samples taken from the jugular vein were performed: a) before surgery (T0), b) after surgery, before awakening (T1), and c) before explanation of the liver (T2). All pigs, divided into four groups of 2 animals each, after general anesthesia were subjected at different times to: median laparotomy, intraoperative ultrasound identification of an ablation area approximately 3.5 cm2, treatment of 3 different liver segments with the anti-cancer compound, organ explantation and euthanasia: the first group was sacrificed 7 days after treatment, the second after 14 days, the third after 21 days and the fourth after 28 days. The explanted liver was then used for macroscopic and microscopic evaluation.

After treatment, all pigs were transferred to the animal facility and monitored daily; facility conditions were compliant with applicable current legislation as all animals were free to roam and feed "ad libitum".

FIGS. 11A to 11F, 12A to 12F, and 13A to 13F are PET/SPECT images of three different porcine livers, respectively, that were explanted after 7 days. The blood samples taken from the pigs, according to the timings indicated in the protocol, did not document any significant abnormalities in blood coagulation parameters. The results of the anatomical and pathological evaluation of the explanted livers, shown in the tables below, characterize the area of ablation at different post-injection time periods of the $^{90}$Y matrix composition.

75 kg pig #1:

| Trial # | Location | Outside Length | Outside Width | Inside Length | Inside Width | Size |
|---|---|---|---|---|---|---|
| 1 | Left lobe | 5.0 | 4.8 | 4.6 | 4.0 | 4.4 × 3.8 |
| 3 | Right lobe | 5.2 | 4.6 | 4.3 | 4.0 | 4.3 × 3.8 |
| 4 | Inferior right lobe | 5.4 | 4.4 | 5.0 | 4.6 | 4.7 × 4.2 |

80 kg pig #2:

| Trial # | Location | Outside Length | Outside Width | Inside Length | Inside Width | Size |
|---|---|---|---|---|---|---|
| 1 | Left lobe second position | 4.0 | 5.0 | 4.5 | 4.2 | 4.3 × 4.0 |
| 3 | Left lobe | 4.0 | 4.0 | 4.1 | 4.2 | 4.0 × 4.1 |
| 3 | Lateral right lobe | 5.8 | 5.5 | 5.5 | 5.0 | 5.2 × 5.0 |

85 kg pig #3:

| Trial # | Location | Outside Length | Outside Width | Inside Length | Inside Width | Size |
|---|---|---|---|---|---|---|
| 1 | Medial right lobe | 4.5 | 4.2 | 4.9 | 4.5 | 4.7 × 4.5 |
| 2 | Lateral right lobe | 4.5 | 4.0 | 4.6 | 4.2 | 4.3 × 4.0 |
| 3 | Medial left lobe | 5.0 | 4.9 | 4.3 | 5.0 | 4.1 × 4.7 |

75 kg pig #4:

| Trial # | Location | Outside Length | Outside Width | Inside Length | Inside Width | Size |
|---|---|---|---|---|---|---|
| 1 | Medial left lobe | 5.4 | 5.1 | 5.1 | 4.1 | 5.0 × 4.0 |
| 2 | Medial right lobe | 6.0 | 5.2 | 5.5 | 4.9 | 5.3 × 4.8 |
| 3 | Lateral right lobe | 5.4 | 5.0 | 5.0 | 4.2 | 5.0 × 4.0 |

85 kg pig #5:

| Trial # | Location | Outside Length | Outside Width | Inside Length | Inside Width | Size |
|---|---|---|---|---|---|---|
| 1 | Medial left lobe | 5.5 | 4.5 | 5.2 | 4.2 | 5.0 × 4.0 |
| 2 | Deep right lobe | 5.2 | 4.3 | 4.2 | 4.0 | 4.0 × 4.0 |
| 3 | Lateral right lobe | 6.0 | 5.0 | 5.1 | 4.2 | 5.0 × 4.0 |

100 kg pig #6:

| Trial # | Location | Outside Length | Outside Width | Inside Length | Inside Width | Size |
|---|---|---|---|---|---|---|
| 1 | Medial left lobe | 6.2 | 5.1 | 5.4 | 4.2 | 5.3 × 4.2 |
| 2 | Medial right lobe | 5.5 | 4.1 | 5.0 | 4.0 | 4.8 × 4.0 |
| 3 | Lateral right lobe | 5.0 | 4.6 | 4.6 | 4.2 | 4.5 × 4.0 |

| 90 kg pig #7: | | | | | | |
|---|---|---|---|---|---|---|
| Trial # | Location | Outside Length | Outside Width | Inside Length | Inside Width | Size |
| 1 | Medial left lobe | 5.1 | 4.5 | 4.8 | 4.5 | 4.8 × 4.5 |
| 2 | Medial right lobe | 5.0 | 4.5 | 4.0 | 4.0 | 4.5 × 4.0 |
| 3 | Lateral left lobe | 6.0 | 5.0 | 5.0 | 4.5 | 5.0 × 4.5 |

| 80 kg pig #8: | | | | | | |
|---|---|---|---|---|---|---|
| Trial # | Location | Outside Length | Outside Width | Inside Length | Inside Width | Size |
| 1 | Medial right lobe | 5.2 | 4.5 | 5.0 | 4.5 | 5.0 × 4.5 |
| 2 | Medial right lobe | 5.7 | 4.8 | 4.7 | 4.2 | 4.7 × 4.0 |
| 3 | Lateral right lobe | 5.0 | 5.0 | 4.5 | 4.5 | 4.5 × 4.3 |

Based on the results above, the use of a locoregional approach to treatment of hepatic lesions appears to be potentially useful and appropriate for human treatment, based on ablation sizes ranging from 3.7 to 5.3 cm in length and 4.0 to 5.0 cm in width, and absence of side effects on organs and bone marrow.

Example 5: Rabbit Study

Figure 14A:
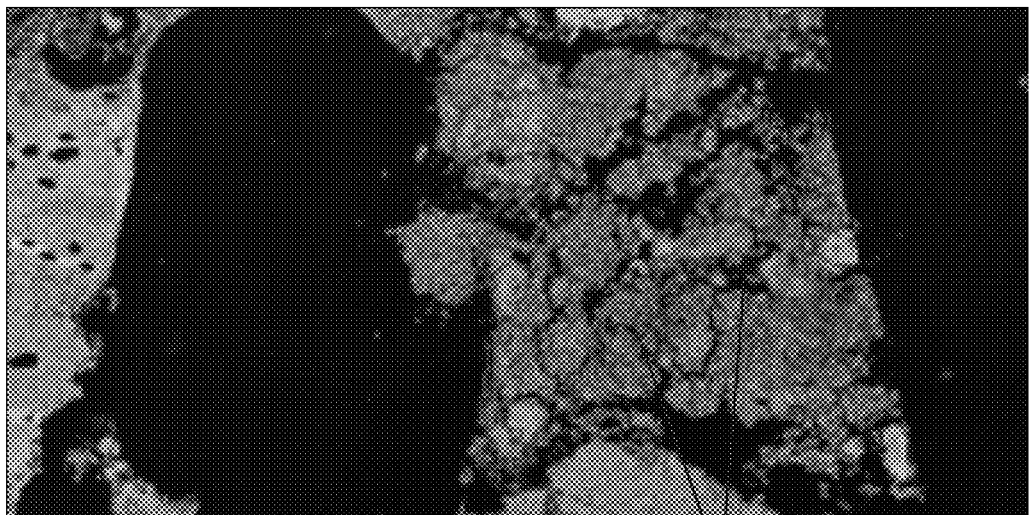
FIGS. 14A and 14B are 20× magnification histology slides post-treatment 7 and 14 days of a resection bed in an animal following intra-tumoral injection of a $^{90}$Y-matrix, with arrows indicating the areas of necrosis.
Figure 14B:
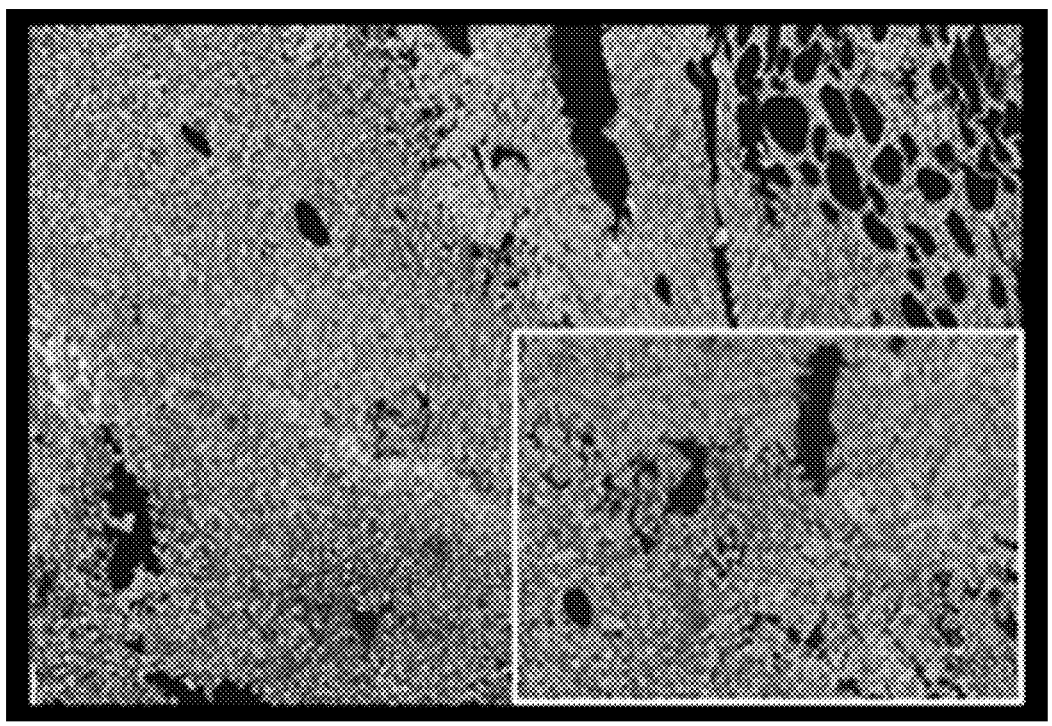

In another animal study, intra-tumoral injection of a $^{90}$Y-loaded hydrogel matrix was used for the treatment of unresectable primary or secondary solid tumors and/or intra-operative local application to prevent or delay local recurrence after resection with positive margins and to confirm efficacy and safety of the procedure. In one study, a $^{90}$Y microsphere-BIOGLUE® composition was used to treat seventy New Zealand rabbits with induced para-renal tumors. The tumors were injected with a $^{90}$Y microsphere-matrix composition and monitored over time. The antineoplastic effect was found to be directly proportional to the time of exposure to the $^{90}$Y microsphere-BIOGLUE® composition, with treated tumors exhibiting 10% average necrosis at day 7, 30% average necrosis at day 14, and 90% average necrosis at day 21. The results of this study showed that the histological examination of the positive resection margin of the bed after nephrectomy and treatment with $^{90}$Y-microspheres hydrogel mixture demonstrated almost total necrosis of viable VX2 carcinoma tumor cells after 21 days. FIGS. 14A and 14B depict the histological tissue analysis of the positive resection margin of the bed after nephrectomy and treatment with a hydrogel matrix and $^{90}$Y microspheres after 7 and 14 days, respectively. FIG. 14A shows that 7 days after treatment, the percentage of necrotic cells is 70%, while FIG. 14B shows that after 14 days, the percentage of necrotic cells is 90%, with the arrows indicating areas of necrosis.

Figure 15A:
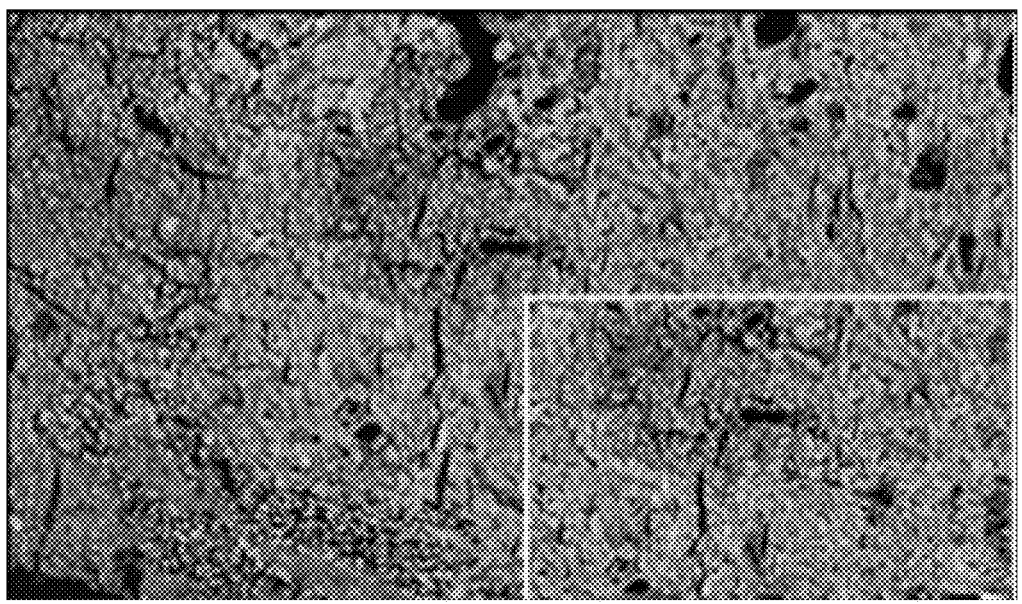
FIGS. 15A and 15B are 20× magnification histology slides post-treatment 7 and 14 days of a resection bed in an animal following intra-tumoral injection of a matrix without any $^{90}$Y.
Figure 15B:
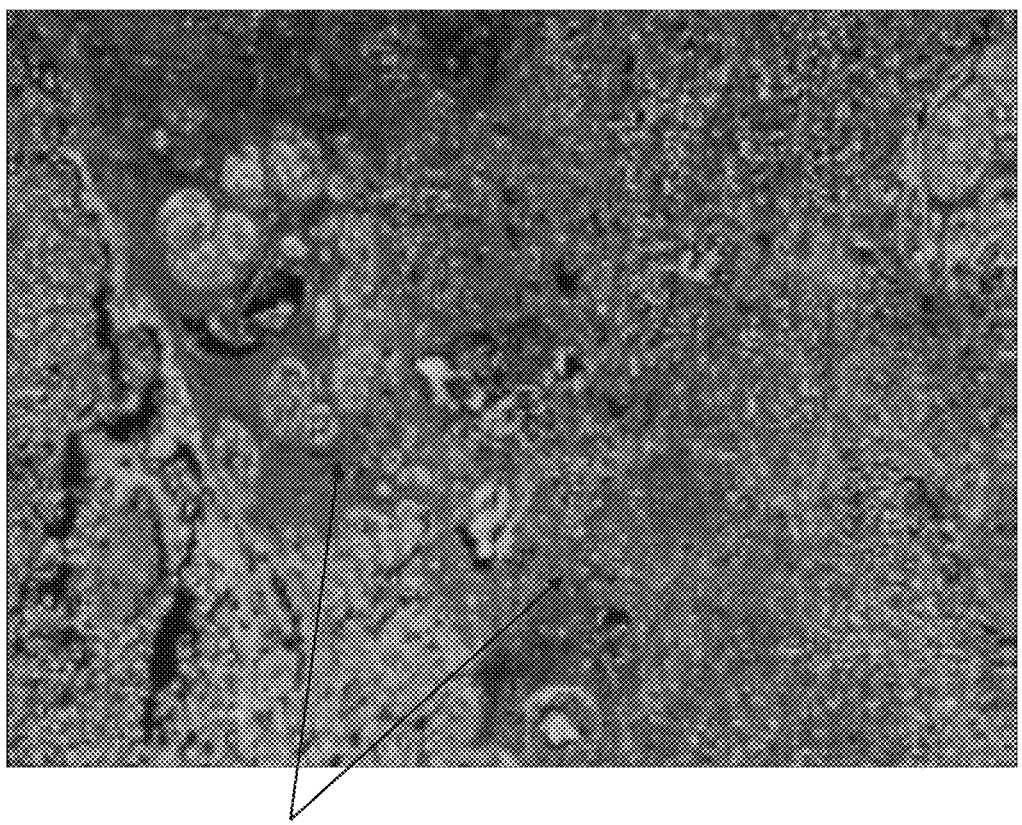
Figure 16A:
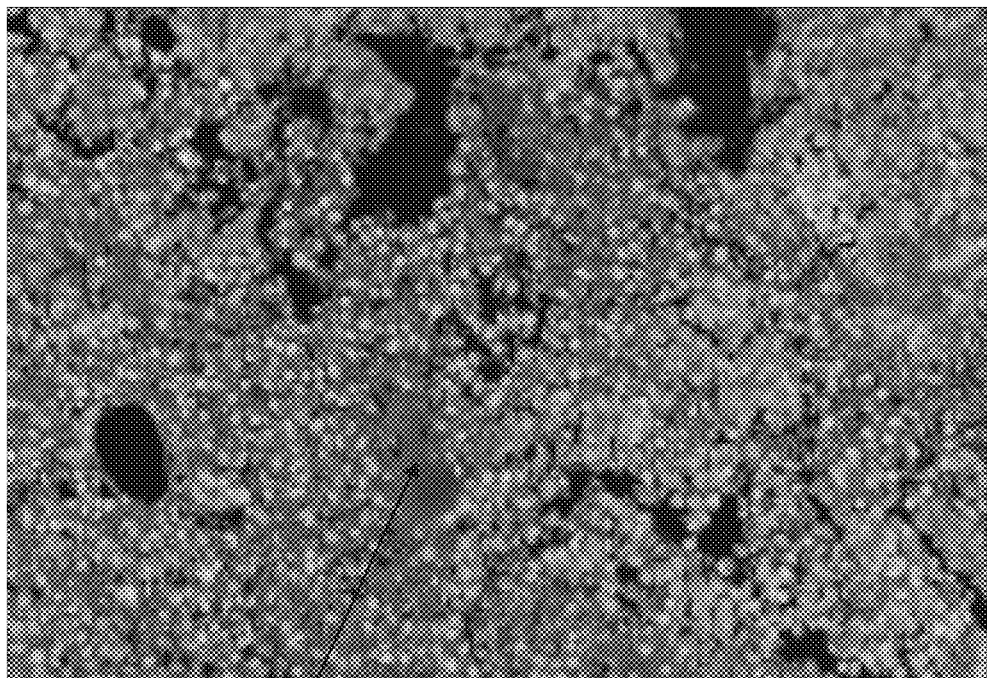
FIGS. 16A and 16B are 20× magnification histology slides post-treatment 7 and 14 days of a resection bed in an animal following intra-tumoral injection of $^{90}$Y without any matrix.
Figure 16B:
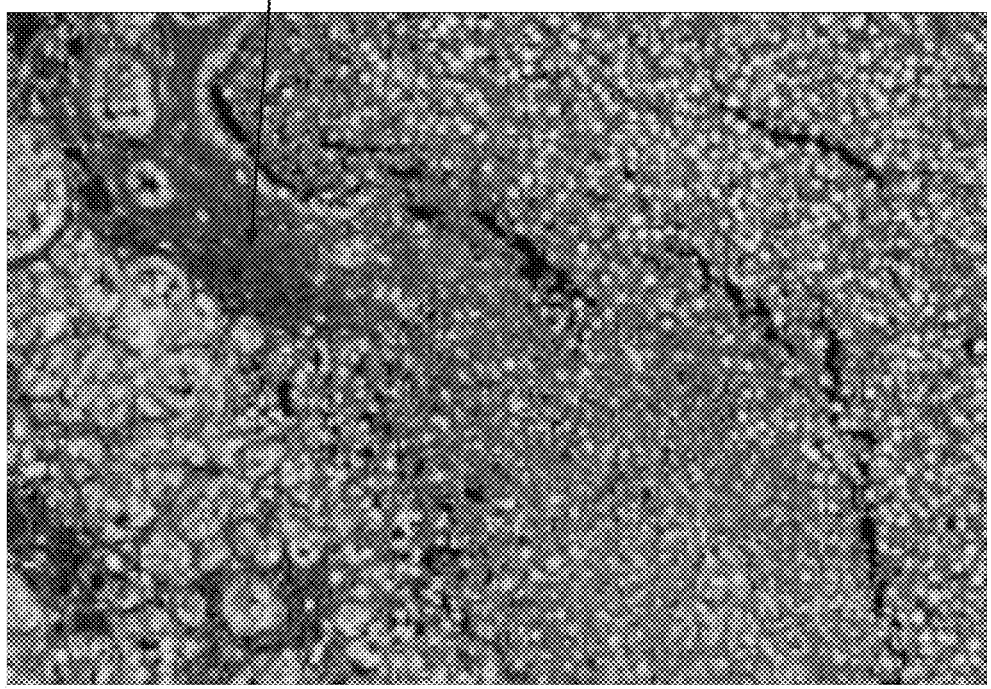

In comparison, the tissue in the resection bed of the animals treated with Hydrogel or $^{90}$Y-microspheres alone showed a palpable macroscopic tumor growth and a histological examination showed the presence of viable VX2 carcinoma cells after 7, 14 and 21 days. FIGS. 15A and 15B depict the histology of a positive resection margin of the tumor bed after nephrectomy and treatment with a hydrogel-only after 7 and 14 days, respectively, and FIGS. 16A and 16B depict the histology of a positive resection margin of the tumor bed ater nephrectomy and treatment with $^{90}$Y microspheres-only after 7 and 14 days, respectively. In FIGS. 15A and 15B histology slides, viable tumor cells can be seen, as indicated by the arrows, within a 5% area of necrosis after treatment with a hydrogel. FIGS. 16A and 16B depict that the percentage of necrotic cells ater 7 and 14 days with injection of Y microspheres-only is 20%.

The total levels of $^{90}$Y in the resected tissue in the rabbits treated with a $^{90}$Y-matrix composition and $^{90}$Y-only (without matrix) are included below:

| $^{90}$Y (CPM) | Organ | # Days post-treatment | Treatment type |
|---|---|---|---|
| 75727 | Injection site | 7 | $^{90}$Y + matrix |
| 10106 | Injection site | 14 | $^{90}$Y + matrix |
| 287 | Liver | 7 | $^{90}$Y + matrix |
| 176 | Liver | 14 | $^{90}$Y + matrix |
| 351 | Lung | 7 | $^{90}$Y + matrix |
| 282 | Lung | 14 | $^{90}$Y + matrix |
| 411 | Heart | 7 | $^{90}$Y + matrix |
| 216 | Heart | 14 | $^{90}$Y + matrix |
| 400 | Right kidney | 7 | $^{90}$Y + matrix |
| 280 | Right kidney | 14 | $^{90}$Y + matrix |
| 6000 | Injection site | 7 | $^{90}$Y only |
| 4000 | Injection site | 14 | $^{90}$Y only |
| 200 | Liver | 7 | $^{90}$Y only |
| 150 | Liver | 14 | $^{90}$Y only |
| 200 | Lung | 7 | $^{90}$Y only |
| 130 | Lung | 14 | $^{90}$Y only |
| 197 | Heart | 7 | $^{90}$Y only |
| 106 | Heart | 14 | $^{90}$Y only |
| 300 | Right kidney | 7 | $^{90}$Y only |
| 120 | Right kidney | 14 | $^{90}$Y only |

Furthermore, due to the application of the hydrogel matrix containing $^{90}$Y microspheres, the system described in this study for administering the composition in the resection bed represents a multimodal approach to the treatment of solid tumors that appears to achieve higher counts than $^{90}$Y injection alone, using the same activity level.

The viscosity and density of the hydrogel matrix (hydrogel) allows the hydrogel mixture to be directly injected or layered within the resection site, ensuring homogeneous distribution, an increase in the local concentration of the $^{90}$Y radiation agent, longer retention in situ and low or no dispersion of the $^{90}$Y spheres, thus potentially limiting systemic side effects.

Through this study, a high concentration of $^{90}$Y levels in the $^{90}$Y-loaded matrix persisted at the administration site for a longer period of time, when compared to the treatment of rabbits injected with $^{90}$Y spheres alone, achieving complete destruction of residual tumor cells (positive margins) created in our animal model.

These results demonstrate that use of the $^{90}$Y microspheres and hydrogel combination achieves a high concentration of $^{90}$Y for a prolonged period compared to the administration of $^{90}$Y microspheres alone, and also achieves homogeneous distribution, thus treating tumor cells in the animal model and potentially reducing the relative risk of local recurrence in the animals who received treatment with $^{90}$Y-matrix compared to those receiving $^{90}$Y alone. In addition, the evaluations carried out in animals treated with $^{90}$Y-matrix, compared to the controls, revealed no levels of radioactivity in the blood, no myelosuppression, no renal, cardiac or pulmonary toxicity and no intestinal perforations or bleeding related to the spread of the $^{90}$Y microspheres, as opposed to the findings observed in the animals receiving $^{90}$Y alone.

Figure 17A:
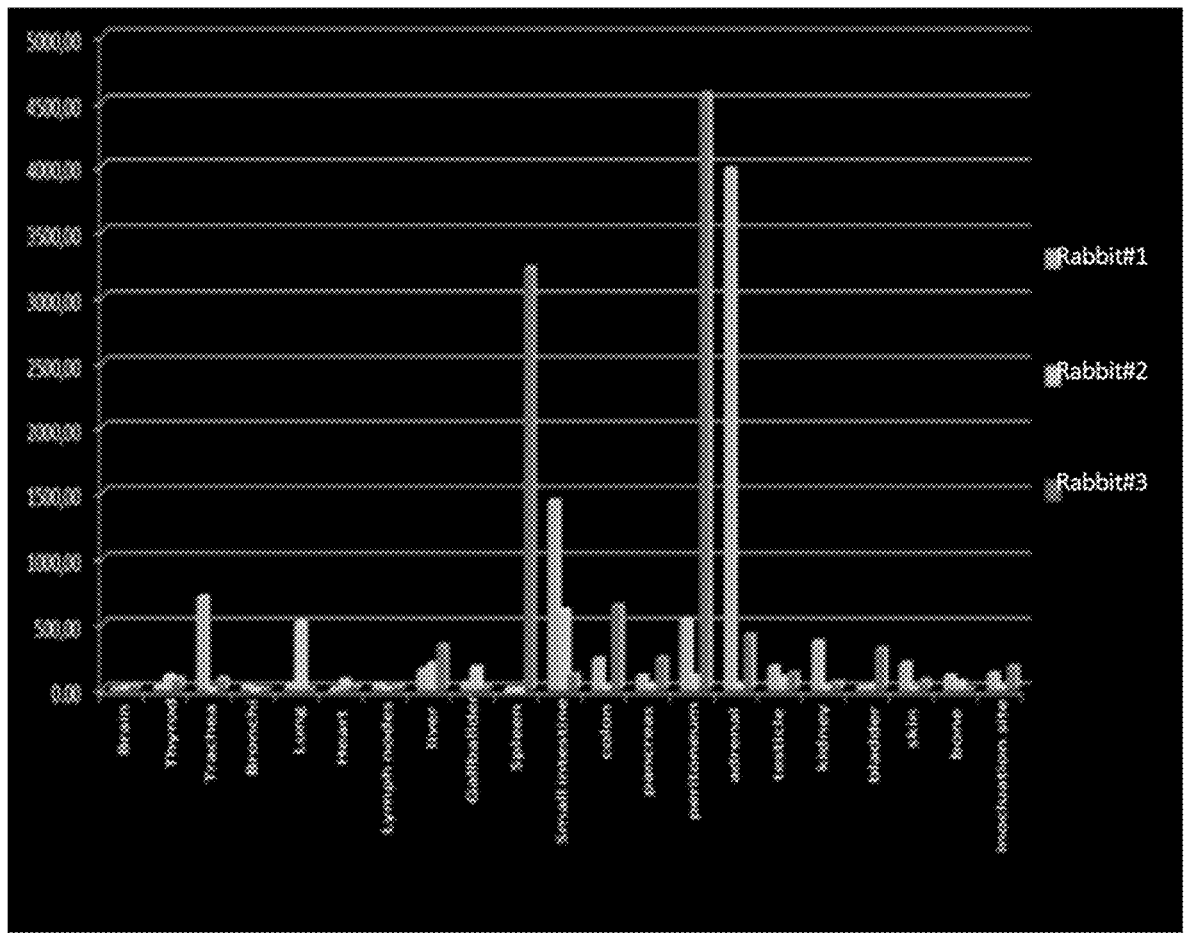
FIGS. 17A and 17B depict the organ system biodistribution of $^{90}$Y microspheres and $^{90}$Y-matrix, respectively.
Figure 17B:
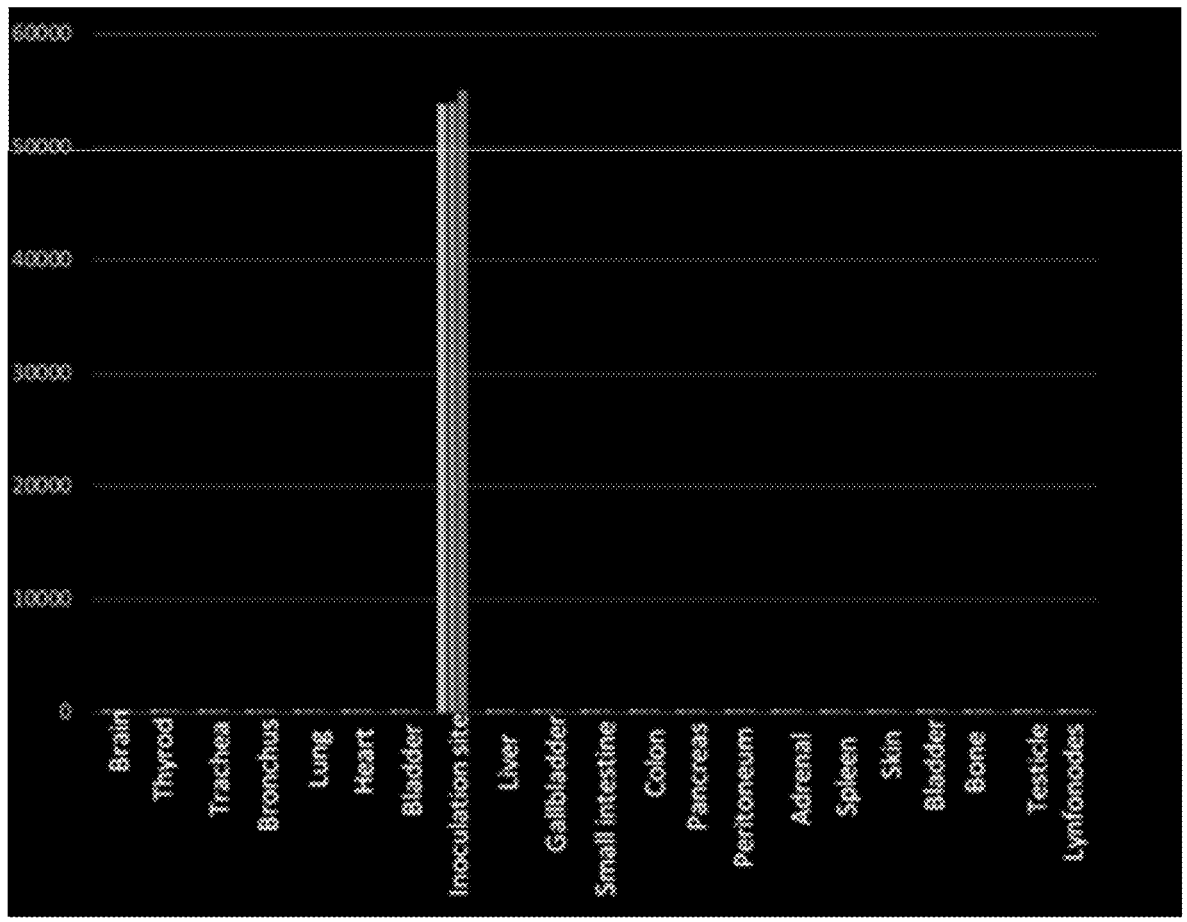

Three rabbits were also injected with $^{90}$Y microspheres at a target location and a beta counter was used to quantify the distribution of $^{90}$Y throughout the body. FIG. 17A illustrates that little activity remained at the target locations of each rabbit, and some activity was detected at every organ location, but with substantial activity concentrated at the spleen, small intestine, peritoneum and adrenal glands of at least some of the animals. In contrast, the same three rabbits also underwent injection with the $^{90}$Y-matrix at the same location. Activity was detected only at the target locations, with negligible or no activity detected at any of the other organ locations.

Example 6 Breast Cancer

With the increasing occurrence of very small, radiologically detected subclinical lesions, several teams started considering, in the 1990's, most DCIS diagnoses as a possibly "indolent disease" and claimed that lumpectomy alone could be the treatment of choice in patients presenting with small size unifocal DCIS. The administration of 50 Gy in 25 fractions over 5 weeks to the whole breast was considered the standard until a few years ago, when the publication of the long-term results of important British and Canadian randomized studies proved the effectiveness and efficiency of schemes administered over shorter times (hypo-fractionated radiotherapy). DCIS is not normally palpable; the widespread use of screening mammography has allowed the diagnosis of increasing numbers of patients with DCIS, who now account for 20-30% of all mammographically detected breast cancers.

Women diagnosed with DCIS are treated with breast-conserving surgery (BCS) in more than ⅔ of the cases, with or without adjuvant therapy. The ipsilateral recurrence rate for women operated on by BCS for DCIS is 1-3% per year, long-term local recurrence rates can be higher than 35% for women operated by surgery alone and are much lower (15% at 10 yrs.) if external beam is added to surgery. Several factors are associated with the increased risk of local recurrence after BCS, among which the strongest one is whether DCIS has been fully excised or not:

1. Margins that are clear from cancer or are more than 1 mm away from cancer have a much lower risk. If margins are not clear from cancer, patients should undergo new surgery to achieve a radical treatment; this can occur in around 20% of patients.

2. Intraoperative radiotherapy (IORT), in which postoperative whole-breast irradiation is substituted by one session of radiotherapy with a dose of 16-20 Gy after surgical resection, allows the treatment to be completed on the same day.

3. Recent trials such as electron intraoperative radiotherapy versus external beam radiotherapy for early breast cancer (ELIOT trial) and targeted intraoperative radiotherapy versus whole breast radiotherapy for breast cancer (TARGIT-A trial) have demonstrated that IORT in selected groups of low-risk early breast cancer patients results in acceptable outcomes in terms of local disease control and could, therefore, serve as an alternative to conventional WBRT, representing a good compromise between treating all patients with external beam radio-therapy and not treating patients at all.

In the Consensus Statement regarding Accelerated Partial Breast Irradiation published on 2017 by American Society for Radiation Oncology (ASTRO), were provided some recommendations on selection criteria for "suitable" patients with low-risk DCIS. On the basis of the clinical experience accumulated in over 15 years of treatments based on trans-arterial infusion of $^{90}$Y-coated microspheres, it is reasonable to assume that the administration of the appropriate activity of $^{90}$Y in the surgical bed of the resected mammary gland should overcome some limitations of WBRT and IORT, and reduce drastically the chances of local recurrence which occurs in the vast majority of cases in the surgical bed. From data available in literature, a target dose of 20 Gy (≥18 Gy) is believed to be sufficient to effectively ablate the tissue surrounding the surgical bed of a resected DCIS lesion.

In one example, a clinical study on the use of a $^{90}$Y-matrix composition was performed. The $^{90}$Y-matrix composition comprised a combination of BIOGLUE® with SIR-SPHERES® loaded with Yttrium-90. In the study, microspheres pre-loaded with $^{90}$Y were blended with a surgical glue for the radio-ablation of surgical margins following the resection of breast DCIS. The study was a multi-center, non-inferiority, pre-market, First-In-Human pilot study for patients with biopsy-proven breast DCIS, eligible to receive breast-conserving surgery. The primary objectives of this study are to assess the ability to reach the surgical bed of a DCIS resection as planned, and to deliver a pre-determined dose without treatment-limited clinical complications. Alternatively, the primary objective may be to assess the performance of the $^{90}$Y-matrix composition in the delivery of an absorbed dose of 20 Gy (≥18 Gy) for the radio-ablative procedure of surgical margins following DCIS resection. The secondary objectives of this study were to evaluate the performance of the $^{90}$Y-matrix composition through imaging procedures (PET-CT and DW-MRI), to assess local and systemic toxicity, and to assess quality of life of enrolled patients. The subjects will be followed up for 1 to 3 months after radio-ablation of surgical margins with the $^{90}$Y-matrix composition following DCIS resection. The study, however, will be considered concluded for each subject after the examination of the Magnetic Resonance-Diffusion Weighted Imaging or mammography. The total study duration per patient is of 15 weeks, with an enrollment period of 6 months. The primary endpoint of the study will be the ability to reach the surgical bed of the DCIS resection as planned, and to deliver a pre-determined dose without treatment-limiting clinical complications. The secondary endpoints will be (1) the volume/extent of surgical margin tissue ablated by the use of the $^{90}$Y-glue matrix composition, following surgical resection of the segment containing the lesion, as measured by PET-CT (Positron Emission Tomography-Computerized Tomography) 2-6 hours after surgery and 24 hours after surgery, and by mammography or (if available) Magnetic Resonance-Diffusion Weighted Imaging (MRI-DW, Day 30); (2) the safety of the procedure, as determined by vital signs, laboratory tests, type and severity of any adverse events and/or device deficiency or usability associated with the procedure of radio-ablation following surgical resection; and (3) the quality of life of the enrolled patients, as measured by the EORTC QLQ-C30 and BR23 Questionnaires.

A sample size of 10 to 20 subjects will be enrolled. In further embodiments, a sample size of 20 subjects can achieve an 80% power to detect a non-inferiority primary endpoint using a one-side (alpha=0.025), one sample test. Because this FIH study explores the performance and safety of the $^{90}$Y-matrix composition, an effect of 20 Gy delivered locally by the $^{90}$ Y-matrix composition has been deemed plausible by looking at results of similar studies. The non-inferiority margin of 18 Gy has been evaluated as clinically significant and the standard deviation has been assumed to be 3 Gy. Sample size estimation has been performed using SAS version 9.4.

The inclusion criteria for the study will be:
Female, Age≥50;
Subjects with biopsy-proven breast DCIS, eligible to receive BCS and "suitable" for partial breast irradiation as per the latest ASTRO guidelines (Age≥50; low to intermediate nuclear grade; resected with margins negative at ≥3 mm; Tis; Size≤25 mm).
Subjects may undergo subsequent External Beam Radiotherapy (EBRT) if deemed appropriate by the treating physician;
Subjects with mammographic or Contrast-Enhanced Magnetic Resonance Imaging evidence of DCIS;
Subjects with a localized DCIS (≥3 mm and ≤25 mm), with a location accessible to percutaneous ablation;
Clinically negative axillary lymph nodes and no clinical findings suggestive of invasive breast cancer.

The exclusion criteria for the study will be:
Female, Age≥50;
Histotype different from carcinoma;
Paget carcinoma;
Lesions located near to axilla region or cutaneous areas (≤15 mm);
Presence of microcalcifications extending for more than 30 mm;
Pregnancy or breast-feeding ongoing;
Positive history for neoplasia (with the exclusion of carcinoma in situ of a portion or skin cancer surgically removed and contra lateral breast cancer without any sign of disease progression in the last 15 years).

Each subject will undergo imaging and have the DCIS lesion diagnosed and staged as follows:
The surgical bed following resection of the target lesion will be treated with radio-ablation using the experimental device;
An appropriate absorbed dose of 20 Gy (≥18 Gy) will be administered to the surgical bed following DCIS resection in order to achieve ablation;
Within 7 days after the surgical procedure, the patients will return at site for the assessment of the volume of the effect of the administration of $^{90}$Y-matrix composition on the surgical bed, as well as for its cosmetic and toxicity evaluation;
30 (±5) days later the surgical bed treated with radio-ablation will be assessed using Magnetic Resonance Diffusion Weighted Imaging or mammography in order to evaluate the extent of the ablated tissue.

Optionally, for the first five patients, additional patient assessment and clinical clearance will be performed. The clinical clearance will include validations of the follow-up data for at least 1 week, if no complications occurred, or 4 weeks, in case of complications. This will include validation of unscheduled contacts with the patient, if performed.

Once the diagnosis of DCIS is confirmed and the inclusion/exclusion criteria met, subjects will be enrolled in the study and admitted to the hospital the day before their scheduled surgery, according to the normal clinical practice. On the day of the surgery, subjects will undergo DCIS excision plus surgical bed ablation with a $^{90}$Y-matrix composition, through a procedure that will require collaboration between the surgeon and the nuclear medicine specialist. Once the treatment is performed, subjects will return to the surgical ward and be discharged the day after the surgery/ablation procedure. Subjects will be followed-up 7, 30 and 90 days after surgery to assess their local and general conditions; at the end of follow-up, they may undergo subsequent external beam radiotherapy if deemed appropriate by the treating physician.

The subjects will be informed about the aims, procedures and possible risks of the study and will be asked to sign the informed consent form. Each screened subject will be identified by a progressive screening number. Subjects will be enrolled only after having signed the informed consent form before any other study procedure. All the patients followed by the investigational center will be checked for adherence to the inclusion and exclusion criteria. One or more of the following information will be collected, though the collection of the information need not be collected on the same exemplary schedule:

|  | Screening V-1 | Surgery and Radioablation V0 | Follow up V1 | Follow up V2 | Follow up V3 |
| --- | --- | --- | --- | --- | --- |
| Days | −15 to 0 | Day 0 | Day 7 ± 2 | Day 30 ± 5 | Day 90 ± 7 |
| Informed Consent | X | | | | |
| Demographic data and/or Medical History | X | | | | |
| Vital Signs and physical measurements (e.g. BP, HR, height and weight) | X | X | X | X | X |
| Inclusion and Exclusion Criteria | X | | | | |
| General and Physical Examination | X | X | X | X | X |
| ECG evaluation | X | | | | |
| DCIS Diagnosis – Mammography + Ultrasound | X | | | | |
| Mammary Ultrasound | | | | | X |
| Urinary pregnancy test | X | | | | |
| EORTC QLQ-C30 and BR23 Questionnaires | X | | X | X | X |
| Concomitant Medications | X | X | X | X | X |
| Hematology and blood chemistry | X | X | X | X | X |
| DCIS Surgery and BAT-90 Delivery (preparation and administration to patients) | | X | | | |

-continued

| Days | Screening V-1 −15 to 0 | Surgery and Radioablation V0 Day 0 | Follow up V1 Day 7 ± 2 | Follow up V2 Day 30 ± 5 | Follow up V3 Day 90 ± 7 |
|---|---|---|---|---|---|
| Surgical Bed Evaluation | | X | | | |
| Blood Sampling (1, 3, 6 and 12 hours after BAT-90 | | X | | | |
| Implant Card | | X | | | |
| PET-CT (breast gland) | | 2/6/24 hours after surgery | | | |
| Whole body scintigraphy | | 16/24 hours after surgery | | | |
| Dosimetry | | X | X | | |
| MRI-Diffusion Weighted (breast gland) | X | | X or mammography | | |
| Safety and Tolerability Assessment/Local Toxicity | | X | X | X | X |
| Device Deficiencies | | X | | | |
| Cosmetic Evaluation | | | X | X | X |

If all the entry criteria are fulfilled, patients will be planned for the ablation procedure by using the $^{90}$Y-matrix composition 1 week after screening. Each patient will be followed-up for any adverse events or adverse effects from the informed consent signature date, during the whole study duration. A blood sample will be collected for the following hematological and biochemical determinations at each study visit:

Complete blood count with differential
Electrophoretic protein pattern
APTT
INR
Fibrinogen
Blood glucose
Blood urea nitrogen (BUN)
Creatinine
AST, ALT, total and fractionated bilirubin, GGT, LDH, alkaline phosphatase
Serum ions: sodium, calcium, potassium, chloride
Tumor marker (AFP)

Blood sampling to detect early blood disorders at 1, 3, 6 and 12 hours after $^{90}$Y-matrix composition delivery at V$_0$:

Complete blood count with differential
AST, ALT, total and fractionated bilirubin, GGT, LDH, alkaline phosphatase All data for the study subjects will be presented using descriptive statistics as mean, standard deviation, median, minimum, maximum or frequency tables, as appropriate. For the primary endpoint a confidence interval (CI) with a significance level of 5% will be estimated and the lower boundary of the CI will be compared to the non-inferiority margin in order to test the non-inferiority. Secondary endpoints involve the evaluation of quality of life (as measured by the EORTC QLQ-C30 and BR23 Questionnaires), the evaluation of the volume/extent of surgical margin tissue ablated (as measured by PET-CT and by Mammography or Magnetic Resonance-Diffusion Weighted Imaging) and the demonstration of the safety profile of $^{90}$Y-matrix composition. Scores of quality of life questionnaires, volume/extent of surgical margin tissue ablated and their change over time will be evaluated by descriptive statistics. Incidence of adverse events, with regards also to the relationship with the $^{90}$Y-matrix composition, will be calculated for all patients, along with their severity and the seriousness. Safety assessments will consist of recording and tabulating all adverse events, as well as with an analysis of changes in vital signs and laboratory parameters. Descriptive statistics will be provided for safety variables.

For one exemplary procedure, a syringe size, 2 mL or 5 mL, of the BIOGLUE® will be selected based on the size(s) or total volume(s) of the tumor as determined on the pre-procedure work-up. $^{90}$Y-matrix composition is prepared during the pre-procedure set-up as follows:

1. Unpack SIR-SPHERES® microspheres, leaving shipping vial in lead pot.

2. Place on the bench top in a lead or acrylic shielded box if available.

3. Remove the SIR-SPHERES® microspheres shipping vial from the lead pot and shake vigorously to disperse the SIR-SPHERES® microspheres.

4. Using a dose calibrator, such as a gamma camera, to determine the activity in the shipping vial and return it to the lead pot.

5. Determine the volume to be withdrawn to provide the required patient radiation dose. The following tables show the activity values of SIR-SPHERES® to be inserted into the 2 ml or 5 ml BIOGLUE® syringe, depending on the radius of the tumor bed. In order to calculate the activity, a vial of SIR-SPHERES® containing a 3 GBq/5 ml dose was considered. Moreover, it has been considered a residual of 300 microliters will remain in the BIOGLUE® syringe at the end of the treatment on the patient. The table also shows the volumes of SIR-SPHERES® to be placed into the BIOGLUE® syringe in ratios of 1:4 (glutaraldehyde: bovine albumin) using the 2 ml/5 ml syringe respectively. For tumor sizes less than 50 mm radius, a 2 mL syringe is selected, and assuming that the SIR-SPHERES® and BIOGLUE® are uniformly mixed and the maximum amount of the mixture is dispensed, leaving a nominal 300 μL residual of the mixture in the syringe:

| Tumor radius (mm) | Expected Syringe Activity (MBq) | Amount $^{90}$Y suspension withdrawn (μL) | Sub-volumes of $^{90}$Y suspension loaded into each syringe chamber BSA (μL) | Glutar- aldehyde (μL) | Combined Volume (μL) | Injected Activity (MBq) | Residual Activity (MBq) |
|---|---|---|---|---|---|---|---|
| 20 | 20 | 100 | 20 | 80 | 2.100 | 17.1 | 2.9 |
| 25 | 25 | 125 | 25 | 100 | 2.125 | 21.5 | 3.5 |
| 30 | 35 | 175 | 35 | 140 | 2.175 | 30.2 | 4.8 |
| 35 | 50 | 250 | 50 | 200 | 2.250 | 43.3 | 6.7 |
| 40 | 70 | 350 | 70 | 280 | 2.350 | 61.1 | 8.9 |
| 45 | 90 | 450 | 90 | 360 | 2.450 | 79.0 | 11.0 |

For tumor sizes from 50 mm radius to 70 mm radius or higher, a 5 mL syringe is selected, and assuming that the SIR-SPHERES® and BIOGLUE® are uniformly mixed and the maximum amount of the mixture is dispensed, leaving a nominal 300 μL residual of the mixture in the syringe:

| Tumor radius (mm) | Expected Syringe Activity (MBq) | Amount $^{90}$Y suspension withdrawn (μL) | Subvolumes of $^{90}$Y suspension loaded into each syringe chamber BSA (μL) | Glutar- aldehyde (μL) | Combined Volume (μL) | Injected Activity (MBq) | Residual Activity (MBq) |
|---|---|---|---|---|---|---|---|
| 45 | 90 | 450 | 90 | 360 | 5.450 | 85.0 | 5.0 |
| 50 | 110 | 550 | 110 | 440 | 5.550 | 104.1 | 5.9 |
| 55 | 130 | 650 | 130 | 520 | 5.650 | 123.1 | 6.9 |
| 60 | 140 | 700 | 140 | 560 | 5.700 | 132.6 | 7.4 |
| 65 | 150 | 750 | 150 | 600 | 5.750 | 142.2 | 7.8 |

6. Partially remove the aluminum seal of the SIR-SPHERES® microspheres shipping vial, clean with alcohol swab.

7. Insert a 25-gauge needle through the septum of the shipping vial to create a vent, ensuring the needle is well clear of the contents in the shipping vial.

8. Use a shielded 5 ml syringe with a 20-22 gauge spinal needle at least 70 mm long to puncture the septum of the SIR-Spheres microspheres shipping vial, and quickly draw back and forth several times in order to mix the SIR-Spheres microspheres thoroughly.

9. Quickly withdraw the pre-calculated patient radiation dose and transfer in the two chambers of the BIOGLUE® syringe as described in the following points 10-13.

10. Remove the double-chamber syringe cap containing the glue components.

11. Distribute the microspheres in the double chamber syringe of the glue respecting the ratio of 4:1 (80% in the BSA chamber, 20% in the glutaraldehyde chamber), as reported in the tables before.

12. Reinsert the cap on the syringe.

13. Verify the patient dose by re-measuring the activity in the shipping vial with the dose calibrator, and correct, if necessary.

14. Place the syringe in a radioprotective container suitable for the transport into the operating room/radiology procedure room.

15. At the operating room/radiology procedure room, the prepared syringe/injector system with the $^{90}$Y is removed from the radioprotective container.

16. The sterile package containing the mixing-tip is opened.

17. Hold the syringe upright, and tap the syringe until any air bubbles in the liquids rise to the top of the syringe 18. Connect the sterile mixing-tip applicator contained in the glue package.

19. Briefly shake the syringe.

20. Apply the compound in the surgical cavity pushing on the pistons of the syringe 21. Wait for the compound to polymerize (e.g. wait a few seconds).

22. Proceed to suture the area.

The actual amount to be injected will be decided by the nuclear medicine specialist performing the procedure of radio-ablation, depending on the size of the surgical resection area (tumor bed) to be ablated and on his/her clinical judgement.

For the ablation procedure, the patient will undergo preparation for ablation procedure as per standard procedure of the treating facility. The patient will be prepped and draped in the usual sterile fashion, and anesthesia will be achieved. The target area will be identified by the surgeon intra-operatively, also using an appropriate marker/ink.

For the dosimetric evaluation, assuming that the radiotracer leakage is negligible/absent, two PET/CT scans of the breast region will be acquired, the first one between ⅔ hours post injection (p.i.) and the second one 24 hours p.i. These two scans will enable us to confirm that the time-activity curve follows a physical decay, accordingly to the preclinical data. The dose calculation will be performed by using the MIRD formalism (OLINDA/EXM software). In particular, for the lesion dose, the unit-density sphere model available in OLINDA/EXM will be used, assuming a discoid morphology and a uniform distribution.

In order to confirm the radiotracer biodistribution, the patients will undergo one whole-body scan acquired by SPECT/CT device: the acquisition will be performed between 16-24 hours p.i. This information is useful to confirm that the radiotracer remains confined in the tumor bed.

After discharge, patients will be followed up for 90 days. The study will be considered concluded for each subject after the post-ablation evaluation (V3); during the follow-up, however, information will be collected on any adverse event that might be related with the radio-ablation procedure and included in the clinical research form.

Adverse events will be classified according to established classification systems, such as the Common Terminology Criteria for Adverse Events v5.0.

At the conclusion of the procedure, the needle, the syringe and any other components must be disposed of, following the institution's standard operating procedure for handling biohazardous and/or radioactive materials.

Example 7: Breast Cancer

In another exemplary study design or treatment regimen, the patient selection, monitoring and follow-up are as disclosed for Example 6 above, but the procedure, kit and/or dosing may be different. In this example, the product comprises the combination of a surgical glue, itself a combination of bovine serum albumin and glutaraldehyde in a 4:1 ratio, and microspheres covered with β-emitting $^{90}Y$ isotope. The kit may further comprise one or more syringe shielding devices to protect the user from inadvertent radioactivity exposure.

The kit may be indicated for the ablation of surgical margins after conservative breast surgery, and is contraindicated in patients with known sensitivity to materials of bovine origin or other glue components. One example of a dosing regimen that utilizes a 2 mL BIOGLUE® syringe along with SIR-SPHERES® to achieve a dose at the tumor bed of 20 Gy or ≥18 Gy is:

| | | Volume of $^{90}Y$ suspension Loaded into Each Syringe Chamber | | | Combined $^{90}Y$-Glue Matrix | | |
|---|---|---|---|---|---|---|---|
| Tumor radius (mm) | $^{90}Y$ Nominal Activity (MBq) | microsphere volume (μL) | Glutaraldehyde (μL) | Bovine serum albumin (μL) | Vol. (mL) | Concentration (MBq/mL) | Residual Activity (MBq) | Injected Activity (MBq) |
| 20-24 | 20  | 66.7  | 13.3 | 53.3  | 2.1 | 9.7  | 2.9  | 17.1 |
| 25-29 | 25  | 83.3  | 16.7 | 66.7  | 2.1 | 12.0 | 3.6  | 21.4 |
| 30-34 | 35  | 116.7 | 23.3 | 93.3  | 2.1 | 16.5 | 5.0  | 30.0 |
| 35-39 | 50  | 166.7 | 33.3 | 133.3 | 2.2 | 23.1 | 6.9  | 43.1 |
| 40-44 | 70  | 233.3 | 46.7 | 186.7 | 2.2 | 31.3 | 9.4  | 60.6 |
| 45-49 | 90  | 300.0 | 60.0 | 240.0 | 2.3 | 39.1 | 11.7 | 78.3 |
| 50-54 | 110 | 366.7 | 73.3 | 293.3 | 2.4 | 46.5 | 13.9 | 96.1 |

In some further embodiments, the volume of $^{90}Y$ microsphere solution that is loaded into the $^{90}Y$-matrix syringe may be adjusted based on the nominal decay hour period (x:00 to x:59 per x hour) and tumor size as follows:

| Tumor Bed Radius: 20 mm to 24 mm | | | | | | | | |
|---|---|---|---|---|---|---|---|---|
| | | | Volume of $^{90}Y$ suspension Loaded into Each Syringe Chamber | | | Combined $^{90}Y$-Glue Matrix | | |
| Time (h) | Nominal Activity (MBq) | $^{90}Y$ microsphere volume (μL) | Glutaraldehyde (μL) | Bovine serum albumin (μL) | Vol. (mL) | Concentration (MBq/mL) | Residual activity (MBq) | Injected activity (MBq) |
| 0:00  | 20.0 | 66.7 | 13.3 | 53.3 | 2.1 | 9.7 | 2.9 | 17.1 |
| 1:00  | 20.0 | 67.4 | 13.5 | 53.9 | 2.1 | 9.7 | 2.9 | 17.1 |
| 2:00  | 20.0 | 68.1 | 13.6 | 54.5 | 2.1 | 9.7 | 2.9 | 17.1 |
| 3:00  | 20.0 | 68.9 | 13.8 | 55,1 | 2.1 | 9.7 | 2.9 | 17.1 |
| 4:00  | 20.0 | 69.6 | 13.9 | 55.7 | 2.1 | 9.7 | 2.9 | 17.1 |
| 5:00  | 20.0 | 70.4 | 14.1 | 56.3 | 2.1 | 9.7 | 2.9 | 17.1 |
| 6:00  | 20.0 | 71.1 | 14.2 | 56.9 | 2.1 | 9.7 | 2.9 | 17.1 |
| 7:00  | 20.0 | 71.9 | 14.4 | 57,5 | 2.1 | 9.7 | 2.9 | 17.1 |
| 8:00  | 20.0 | 72.7 | 14.5 | 58,2 | 2.1 | 9.6 | 2.9 | 17.1 |
| 9:00  | 20.0 | 73.5 | 14.7 | 58.8 | 2.1 | 9.6 | 2.9 | 17.1 |
| 10:00 | 20.0 | 74.3 | 14.9 | 59,4 | 2.1 | 9.6 | 2.9 | 17.1 |
| 11:00 | 20.0 | 75.1 | 15.0 | 60.1 | 2.1 | 9.6 | 2.9 | 17.1 |
| 12:00 | 20.0 | 75.9 | 15.2 | 60.7 | 2.1 | 9.6 | 2.9 | 17.1 |
| 13:00 | 20.0 | 76.7 | 15.3 | 61.4 | 2.1 | 9.6 | 2.9 | 17.1 |
| 14:00 | 20.0 | 77.6 | 15.5 | 62.1 | 2.1 | 9.6 | 2.9 | 17.1 |
| 15:00 | 20.0 | 78.4 | 15.7 | 62.7 | 2.1 | 9.6 | 2.9 | 17.1 |
| 16:00 | 20.0 | 79.3 | 15.9 | 63.4 | 2.1 | 9.6 | 2.9 | 17.1 |
| 17:00 | 20.0 | 80.1 | 16.0 | 64.1 | 2.1 | 9.6 | 2.9 | 17.1 |
| 18:00 | 20.0 | 81.0 | 16.2 | 64.8 | 2.1 | 9.6 | 2.9 | 17.1 |
| 19:00 | 20.0 | 81.9 | 16.4 | 65.5 | 2.1 | 9.6 | 2.9 | 17.1 |
| 20:00 | 20.0 | 82.8 | 16.6 | 66.2 | 2.1 | 9.6 | 2.9 | 17.1 |

-continued

| Tumor Bed Radius: 20 mm to 24 mm | | | | | | | |
|---|---|---|---|---|---|---|---|
| | | Volume of $^{90}$Y suspension Loaded into Each Syringe Chamber | | Combined $^{90}$Y-Glue Matrix | | | |
| Time (h) | Nominal Activity (MBq) | $^{90}$Y microsphere volume (μL) | Glutaraldehyde (μL) | Bovine serum albumin (μL) | Vol. (mL) | Concentration (MBq/mL) | Residual activity (MBq) | Injected activity (MBq) |
| 21:00 | 20.0 | 83.7 | 16.7 | 66.9 | 2.1 | 9.6 | 2.9 | 17.1 |
| 22:00 | 20.0 | 84.6 | 16.9 | 67.7 | 2.1 | 9.6 | 2.9 | 17.1 |
| 23:00 | 20.0 | 85.5 | 17.1 | 68.4 | 2.1 | 9.6 | 2.9 | 17.1 |

| Tumor Bed Radius: 25 mm to 29 mm | | | | | | | |
|---|---|---|---|---|---|---|---|
| | | Volume of $^{90}$Y suspension Loaded into Each Syringe Chamber | | Combined $^{90}$Y-Glue Matrix | | | |
| Time (h) | Nominal Activity (MBq) | $^{90}$Y microsphere volume (μL) | Glutaraldehyde (μL) | Bovine serum albumin (μL) | Vol. (mL) | Concentration (MBq/mL) | Residual activity (MBq) | Injected activity (MBq) |
| 0:00 | 25.0 | 83.3 | 16.7 | 66.7 | 2.1 | 12.0 | 3.6 | 21.4 |
| 1:00 | 25.0 | 84.2 | 16.8 | 67.4 | 2.1 | 12.0 | 3.6 | 21.4 |
| 2:00 | 25.0 | 85.2 | 17.0 | 68.1 | 2.1 | 12.0 | 3.6 | 21.4 |
| 3:00 | 25.0 | 86.1 | 17.2 | 68.9 | 2.1 | 12.0 | 3.6 | 21.4 |
| 4:00 | 25.0 | 87.0 | 17.4 | 69.6 | 2.1 | 12.0 | 3.6 | 21.4 |
| 5:00 | 25.0 | 88.0 | 17.6 | 70.4 | 2.1 | 12.0 | 3.6 | 21.4 |
| 6:00 | 25.0 | 88.9 | 17.8 | 71.1 | 2.1 | 12.0 | 3.6 | 21.4 |
| 7:00 | 25.0 | 89.9 | 18.0 | 71.9 | 2.1 | 12.0 | 3.6 | 21.4 |
| 8:00 | 25.0 | 90.9 | 18.2 | 72.7 | 2.1 | 12.0 | 3.6 | 21.4 |
| 9:00 | 25.0 | 91.9 | 18.4 | 73.5 | 2.1 | 12.0 | 3.6 | 21.4 |
| 10:00 | 25.0 | 92.9 | 18.6 | 74.3 | 2.1 | 11.9 | 3.6 | 21.4 |
| 11:00 | 25.0 | 93.9 | 18.8 | 75.1 | 2.1 | 11.9 | 3.6 | 21.4 |
| 12:00 | 25.0 | 94.9 | 19.0 | 75.9 | 2.1 | 11.9 | 3.6 | 21.4 |
| 13:00 | 25.0 | 95.9 | 19.2 | 76.7 | 2.1 | 11.9 | 3.6 | 21.4 |
| 14:00 | 25.0 | 97.0 | 19.4 | 77.6 | 2.1 | 11.9 | 3.6 | 21.4 |
| 15:00 | 25.0 | 98.0 | 19.6 | 78.4 | 2.1 | 11.9 | 3.6 | 21.4 |
| 16:00 | 25.0 | 99.1 | 19.8 | 79.3 | 2.1 | 11.9 | 3.6 | 21.4 |
| 17:00 | 25.0 | 100.2 | 20.0 | 80.1 | 2.1 | 11.9 | 3.6 | 21.4 |
| 18:00 | 25.0 | 101.2 | 20.2 | 81.0 | 2.1 | 11.9 | 3.6 | 21.4 |
| 19:00 | 25.0 | 102.4 | 20.5 | 81.9 | 2.1 | 11.9 | 3.6 | 21.4 |
| 20:00 | 25.0 | 103.5 | 20.7 | 82.8 | 2.1 | 11.9 | 3.6 | 21.4 |
| 21:00 | 25.0 | 104.6 | 20.9 | 83.7 | 2.1 | 11.9 | 3.6 | 21.4 |
| 22:00 | 25.0 | 105.7 | 21.1 | 84.6 | 2.1 | 11.9 | 3.6 | 21.4 |
| 23:00 | 25.0 | 106.9 | 21.4 | 85.5 | 2.1 | 11.9 | 3.6 | 21.4 |

| Tumor Bed Radius: 30 mm to 34 mm | | | | | | | |
|---|---|---|---|---|---|---|---|
| | | Volume of $^{90}$Y suspension Loaded into Each Syringe Chamber | | Combined $^{90}$Y-Glue Matrix | | | |
| Time (h) | Nominal Activity (MBq) | $^{90}$Y microsphere volume (μL) | Glutaraldehyde (μL) | Bovine serum albumin (μL) | Vol. (mL) | Concentration (MBq/mL) | Residual activity (MBq) | Injected activity (MBq) |
| 0:00 | 35.0 | 116.7 | 23.3 | 93.3 | 2.1 | 16.5 | 5.0 | 30.0 |
| 1:00 | 35.0 | 117.9 | 23.6 | 94.4 | 2.1 | 16.5 | 5.0 | 30.0 |
| 2:00 | 35.0 | 119.2 | 23.8 | 95.4 | 2.1 | 16.5 | 5.0 | 30.0 |
| 3:00 | 35.0 | 120.5 | 24.1 | 96.4 | 2.1 | 16.5 | 5.0 | 30.0 |
| 4:00 | 35.0 | 121.8 | 24.4 | 97.5 | 2.1 | 16.5 | 4.9 | 30.1 |
| 5:00 | 35.0 | 123.2 | 24.6 | 98.5 | 2.1 | 16.5 | 4.9 | 30.1 |
| 6:00 | 35.0 | 124.5 | 24.9 | 99.6 | 2.1 | 16.5 | 4.9 | 30.1 |
| 7:00 | 35.0 | 125.9 | 25.2 | 100.7 | 2.1 | 16.5 | 4.9 | 30.1 |

-continued

| Tumor Bed Radius: 30 mm to 34 mm | | | | | | | |
|---|---|---|---|---|---|---|---|
| | | Volume of $^{90}$Y suspension Loaded into Each Syringe Chamber | | Combined $^{90}$Y-Glue Matrix | | | |
| Time (h) | Nominal Activity (MBq) | $^{90}$Y micro-sphere volume (μL) | Glutar-aldehyde (μL) | Bovine serum albumin (μL) | Vol. (mL) | Concen-tration (MBq/mL) | Residual activity (MBq) | Injected activity (MBq) |
| 8:00 | 35.0 | 127.2 | 25.4 | 101.8 | 2.1 | 16.5 | 4.9 | 30.1 |
| 9:00 | 35.0 | 128.6 | 25.7 | 102.9 | 2.1 | 16.4 | 4.9 | 30.1 |
| 10:00 | 35.0 | 130.0 | 26.0 | 104.0 | 2.1 | 16.4 | 4.9 | 30.1 |
| 11:00 | 35.0 | 131.4 | 26.3 | 105.1 | 2.1 | 16.4 | 4.9 | 30.1 |
| 12:00 | 35.0 | 132.8 | 26.6 | 106.3 | 2.1 | 16.4 | 4.9 | 30.1. |
| 13:00 | 35.0 | 134.3 | 26.9 | 107.4 | 2.1 | 16.4 | 4.9 | 30.1 |
| 14:00 | 35.0 | 135.8 | 27.2 | 108.6 | 2.1 | 16.4 | 4.9 | 30.1 |
| 15:00 | 35.0 | 137.2 | 27.4 | 109.8 | 2.1 | 16.4 | 4.9 | 30.1 |
| 16:00 | 35.0 | 138.7 | 27.7 | 111.0 | 2.1 | 16.4 | 4.9 | 30.1 |
| 17:00 | 35.0 | 140.2 | 28.0 | 112.2 | 2.1 | 16.4 | 4.9 | 30.1 |
| 18:00 | 35.0 | 141.8 | 28.4 | 113.4 | 2.1 | 16.3 | 4.9 | 30.1 |
| 19:00 | 35.0 | 143.3 | 28.7 | 114.6 | 2.1 | 16.3 | 4.9 | 30.1 |
| 20:00 | 35.0 | 144.9 | 29.0 | 115.9 | 2.1 | 16.3 | 4.9 | 30.1 |
| 21:00 | 35.0 | 146.4 | 29.3 | 117.1 | 2.1 | 16.3 | 4.9 | 30.1 |
| 22:00 | 35.0 | 148.0 | 29.6 | 118.4 | 2.1 | 16.3 | 4.9 | 30.1 |
| 23:00 | 35.0 | 149.6 | 29.9 | 119.7 | 2.1 | 16.3 | 4.9 | 30.1 |

| Tumor Bed Radius: 35 mm to 39 mm | | | | | | | |
|---|---|---|---|---|---|---|---|
| | | Volume of $^{90}$Y suspension Loaded into Each Syringe Chamber | | Combined $^{90}$Y-Glue Matrix | | | |
| Time (h) | Nominal Activity (MBq) | $^{90}$Y micro-sphere volume (μL) | Glutar-aldehyde (μL) | Bovine serum albumin (μL) | Vol. (mL) | Concen-tration (MBq/mL) | Residual activity (MBq) | Injected activity (MBq) |
| 0:00 | 50.0 | 166.7 | 33.3 | 133.3 | 2.2 | 23.1 | 69.2 | 43.1 |
| 1:00 | 50.0 | 168.5 | 33.7 | 134.8 | 2.2 | 23.1 | 6.9 | 43.1 |
| 2:00 | 50.0 | 170.3 | 34.1 | 136.3 | 2.2 | 23.0 | 6.9 | 43.1 |
| 3:00 | 50.0 | 172.2 | 34.4 | 137.7 | 2.2 | 23.0 | 6.9 | 43.1 |
| 4:00 | 50.0 | 174.0 | 34.8 | 139.2 | 2.2 | 23.0 | 6.9 | 43.1 |
| 5:00 | 50.0 | 175.9 | 35.2 | 140.7 | 2.2 | 23.0 | 6.9 | 43.1 |
| 6:00 | 50.0 | 177.9 | 35.6 | 142.3 | 2.2 | 23.0 | 6.9 | 43.1 |
| 7:00 | 50.0 | 179.8 | 36.0 | 143.8 | 2.2 | 22.9 | 6.9 | 43.1 |
| 8:00 | 50.0 | 181.7 | 36.3 | 145.4 | 2.2 | 22.9 | 6.9 | 43.1 |
| 9:00 | 50.0 | 183.7 | 36.7 | 147.0 | 2.2 | 22.9 | 6.9 | 43.1 |
| 10:00 | 50.0 | 185.7 | 37.1 | 148.6 | 2.2 | 22.9 | 6.9 | 43.1 |
| 11:00 | 50.0 | 187.3 | 37.5 | 150.2 | 2.2 | 22.9 | 6.9 | 43.1 |
| 12:00 | 50.0 | 189.8 | 38.0 | 151.8 | 2.2 | 22.8 | 6.9 | 43.1 |
| 13:00 | 50.0 | 191.8 | 38.4 | 153.5 | 2.2 | 22.8 | 6.8 | 43.2 |
| 14:00 | 50.0 | 193.9 | 38.8 | 155.1 | 2.2 | 22.8 | 6.8 | 43.2 |
| 15:00 | 50.0 | 196.0 | 39.2 | 156.8 | 2.2 | 22.8 | 6.8 | 43.2 |
| 16:00 | 50.0 | 198.2 | 39.6 | 158.5 | 2.2 | 22.7 | 6.8 | 43.2 |
| 17:00 | 50.0 | 200.3 | 40.1 | 160.3 | 2.2 | 22.7 | 6.8 | 43.2 |
| 18:00 | 50.0 | 202.5 | 40.5 | 162.0 | 2.2 | 22.7 | 6.8 | 43.2 |
| 19:00 | 50.0 | 204.7 | 40.9 | 163.8 | 2.2 | 22.7 | 6.8 | 43.2 |
| 20:00 | 50.0 | 206.9 | 41.4 | 165.6 | 2.2 | 22.7 | 6.8 | 43.2 |
| 21:00 | 50.0 | 209.2 | 41.8 | 167.4 | 2.2 | 22.6 | 6.8 | 43.2 |
| 22:00 | 50.0 | 211.5 | 42.3 | 169.2 | 2.2 | 22.6 | 6.8 | 43.2 |
| 23:00 | 50.0 | 213.8 | 42.8 | 171.0 | 2.2 | 22.6 | 6.8 | 43.2 |

| | | Tumor Bed Radius: 40 mm to 44 mm | | | | | | |
|---|---|---|---|---|---|---|---|---|
| | | | Volume of $^{90}$Y suspension Loaded into Each Syringe Chamber | | Combined $^{90}$Y-Glue Matrix | | | |
| Time (h) | Nominal Activity (MBq) | $^{90}$Y microsphere volume (µL) | Glutaraldehyde (µL) | Bovine serum albumin (µL) | Vol. (mL) | Concentration (MBq/mL) | Residual activity (MBq) | Injected activity (MBq) |
| 0:00 | 70.0 | 233.3 | 46.7 | 186.7 | 2.2 | 31.3 | 9.4 | 60.6 |
| 1:00 | 70.0 | 235.9 | 47.2 | 188.7 | 2.2 | 31.3 | 9.4 | 60.6 |
| 2:00 | 70.0 | 238.4 | 47.7 | 190.7 | 2.2 | 31.3 | 9.4 | 60.6 |
| 3:00 | 70.0 | 241.0 | 48.2 | 192.8 | 2.2 | 31.2 | 9.4 | 60.6 |
| 4:00 | 70.0 | 243.7 | 48.7 | 194.9 | 2.2 | 31.2 | 9.4 | 60.6 |
| 5:00 | 70.0 | 246.3 | 49.3 | 197.0 | 2.2 | 31.2 | 9.3 | 60.7 |
| 6:00 | 70.0 | 249.0 | 49.8 | 199.2 | 2.2 | 31.1 | 9.3 | 60.7 |
| 7:00 | 70.0 | 251.7 | 50.3 | 201.4 | 2.3 | 31.1 | 9.3 | 60.7 |
| 8:00 | 70.0 | 254.4 | 50.9 | 203.5 | 2.3 | 31.0 | 9.3 | 60.7 |
| 9:00 | 70.0 | 257.2 | 51.4 | 205.8 | 2.3 | 31.0 | 9.3 | 60.7 |
| 10:00 | 70.0 | 260.0 | 52.0 | 208.0 | 2.3 | 31.0 | 9.3 | 60.7 |
| 11:00 | 70.0 | 262.8 | 52.6 | 210.3 | 2.3 | 30.9 | 9.3 | 60.7 |
| 12:00 | 70.0 | 265.7 | 53.1 | 212.5 | 2.3 | 30.9 | 9.3 | 60.7 |
| 13:00 | 70.0 | 268.6 | 53.7 | 214.9 | 2.3 | 30.9 | 9.3 | 60.7 |
| 14:00 | 70.0 | 271.5 | 54.3 | 217.2 | 2.3 | 30.8 | 9.2 | 60.8 |
| 15:00 | 70.0 | 274.5 | 54.9 | 219.6 | 2.3 | 30.8 | 9.2 | 60.8 |
| 16:00 | 70.0 | 277.4 | 55.5 | 221.9 | 2.3 | 30.7 | 9.2 | 60.8 |
| 17:00 | 70.0 | 280.5 | 56.1 | 224.4 | 2.3 | 30.7 | 9.2 | 60.8 |
| 18:00 | 70.0 | 283.5 | 56.7 | 226.8 | 2.3 | 30.7 | 9.2 | 60.8 |
| 19:00 | 70.0 | 286.6 | 57.3 | 229.3 | 2.3 | 30.6 | 9.2 | 60.8 |
| 20:00 | 70.0 | 289.7 | 57.9 | 231.8 | 2.3 | 30.6 | 9.2 | 60.8 |
| 21:00 | 70.0 | 292.9 | 58.6 | 234.3 | 2.3 | 30.5 | 9.2 | 60.8 |
| 22:00 | 70.0 | 296.0 | 59.2 | 236.8 | 2.3 | 30.5 | 9.1 | 60.9 |
| 23:00 | 70.0 | 299.3 | 59.9 | 239.4 | 2.3 | 30.4 | 9.1 | 60.9 |

| | | Tumor bed Radius: 45 mm to 49 mm | | | | | | |
|---|---|---|---|---|---|---|---|---|
| | | | Volume of $^{90}$Y suspension Loaded into Each Syringe Chamber | | Combined $^{90}$Y-Glue Matrix | | | |
| Time (h) | Nominal Activity (MBq) | $^{90}$Y microsphere volume (µL) | Glutaraldehyde (µL) | Bovine serum albumin (µL) | Vol. (mL) | Concentration (MBq/mL) | Residual activity (MBq) | Injected activity (MBq) |
| 0:00 | 90.0 | 300.0 | 60.0 | 240.0 | 2.3 | 39.1 | 11.7 | 78.3 |
| 1:00 | 90.0 | 303.3 | 60.7 | 242.6 | 2.3 | 39.1 | 11.7 | 78.3 |
| 2:00 | 90.0 | 306.6 | 61.3 | 245.3 | 2.3 | 39.0 | 11.7 | 78.3 |
| 3:00 | 90.0 | 309.9 | 62.0 | 247.9 | 2.3 | 39.0 | 11.7 | 78.3 |
| 4:00 | 90.0 | 313.3 | 62.7 | 250.6 | 2.3 | 38.9 | 11.7 | 78.3 |
| 5:00 | 90.0 | 316.7 | 63.3 | 253.3 | 2.3 | 38.8 | 11.7 | 78.3 |
| 6:00 | 90.0 | 320.1 | 64.0 | 256.1 | 2.3 | 38.8 | 11.6 | 78.4 |
| 7:00 | 90.0 | 323.6 | 64.7 | 258.9 | 2.3 | 38.7 | 11.6 | 78.4 |
| 8:00 | 90.0 | 327.1 | 65.4 | 261.7 | 2.3 | 38.7 | 11.6 | 78.4 |
| 9:00 | 90.0 | 330.7 | 66.1 | 264.5 | 2.3 | 38.6 | 11.6 | 78.4 |
| 10:00 | 90.0 | 334.3 | 66.9 | 267.4 | 2.3 | 38.6 | 11.6 | 78.4 |
| 11:00 | 90.0 | 337.9 | 67.6 | 270.3 | 2.3 | 38.5 | 11.5 | 78.5 |
| 12:00 | 90.0 | 341.6 | 68.3 | 273.3 | 2.3 | 38.4 | 11.5 | 78.5 |
| 13:00 | 90.0 | 345.3 | 69.1 | 276.3 | 2.3 | 38.4 | 11.5 | 78.5 |
| 14:00 | 90.0 | 349.1 | 69.8 | 279.3 | 2.3 | 38.3 | 11.5 | 78.5 |
| 15:00 | 90.0 | 352.9 | 70.6 | 282.3 | 2.4 | 38.3 | 11.5 | 78.5 |
| 16:00 | 90.0 | 356.7 | 71.3 | 285.4 | 2.4 | 38.2 | 11.5 | 78.5 |
| 17:00 | 90.0 | 360.6 | 72.1 | 288.5 | 2.4 | 38.1 | 11.4 | 78.6 |
| 18:00 | 90.0 | 364.5 | 72.9 | 291.6 | 2.4 | 38.1 | 11.4 | 78.6 |
| 19:00 | 90.0 | 368.5 | 73.7 | 294.8 | 2.4 | 38.0 | 11.4 | 78.6 |
| 20:00 | 90.0 | 372.5 | 74.5 | 298.0 | 2.4 | 37.9 | 11.4 | 78.6 |
| 21:00 | 90.0 | 376.5 | 75.3 | 301.2 | 2.4 | 37.9 | 11.4 | 78.6 |
| 22:00 | 90.0 | 380.6 | 76.1 | 304.5 | 2.4 | 37.8 | 11.3 | 78.7 |
| 23:00 | 90.0 | 384.8 | 77.0 | 307.8 | 2.4 | 37.7 | 11.3 | 78.7 |

| Tumor Bed Radius: 50 mm to 54 mm ||||||||
|---|---|---|---|---|---|---|---|
| | | Volume of $^{90}$Y suspension Loaded into Each Syringe Chamber ||| Combined $^{90}$Y-Glue Matrix |||
| Time (h) | Nominal Activity (MBq) | $^{90}$Y microsphere volume (μL) | Glutaraldehyde (μL) | Bovine serum albumin (μL) | Vol. (mL) | Concentration (MBq/mL) | Residual activity (MBq) | Injected activity (MBq) |
| 0:00 | 110.0 | 366.7 | 73.3 | 293.3 | 2.4 | 46.5 | 13.9 | 96.1 |
| 1:00 | 110.0 | 370.7 | 74.1 | 296.5 | 2.4 | 46.4 | 13.9 | 96.1 |
| 2:00 | 110.0 | 374.7 | 74.9 | 299.8 | 2.4 | 46.3 | 13.9 | 96.1 |
| 3:00 | 110.0 | 378.8 | 75.8 | 303.0 | 2.4 | 46.2 | 13.9 | 96.1 |
| 4:00 | 110.0 | 382.9 | 76.6 | 306.3 | 2.4 | 46.2 | 13.8 | 96.2 |
| 5:00 | 110.0 | 387.1 | 77.4 | 309.6 | 2.4 | 46.1 | 13.8 | 96.2 |
| 6:00 | 110.0 | 391.3 | 78.3 | 313.0 | 2.4 | 46.0 | 13.8 | 96.2 |
| 7:00 | 110.0 | 395.5 | 79.1 | 316.4 | 2.4 | 45.9 | 13.8 | 96.2 |
| 8:00 | 110.0 | 399.8 | 80.0 | 319.9 | 2.4 | 45.8 | 13.8 | 96.2 |
| 9:00 | 110.0 | 404.2 | 80.8 | 323.3 | 2.4 | 45.8 | 13.7 | 96.3 |
| 10:00 | 110.0 | 408.6 | 81.7 | 326.9 | 2.4 | 45.7 | 13.7 | 96.3 |
| 11:00 | 110.0 | 413.0 | 82.6 | 330.4 | 2.4 | 45.6 | 13.7 | 96.3 |
| 12:00 | 110.0 | 417.5 | 83.5 | 334.0 | 2.4 | 45.5 | 13.7 | 96.3 |
| 13:00 | 110.0 | 422.1 | 84.4 | 337.6 | 2.4 | 45.4 | 13.6 | 96.4 |
| 14:00 | 110.0 | 426.6 | 85.3 | 341.3 | 2.4 | 45.3 | 13.6 | 96.4 |
| 15:00 | 110.0 | 431.3 | 86.3 | 345.0 | 2.4 | 45.2 | 13.6 | 96.4 |
| 16:00 | 110.0 | 436.0 | 87.2 | 348.8 | 2.4 | 45.2 | 13.5 | 96.5 |
| 17:00 | 110.0 | 440.7 | 88.1 | 352.6 | 2.4 | 45.1 | 13.5 | 96.5 |
| 18:00 | 110.0 | 445.5 | 89.1 | 356.4 | 2.4 | 45.0 | 13.5 | 96.5 |
| 19:00 | 110.0 | 450.4 | 90.1 | 360.3 | 2.5 | 44.9 | 13.5 | 96.5 |
| 20:00 | 110.0 | 455.3 | 91.1 | 364.2 | 2.5 | 44.8 | 13.4 | 96.6 |
| 21:00 | 110.0 | 460.2 | 92.0 | 368.2 | 2.5 | 44.7 | 13.4 | 96.6 |
| 22:00 | 110.0 | 465.2 | 93.0 | 372.2 | 2.5 | 44.6 | 13.4 | 96.6 |
| 23:00 | 110.0 | 470.3 | 94.1 | 376.2 | 2.5 | 44.5 | 13.4 | 96.6 |

The kit that may be used includes:
two syringes (1 ml.) with Luer-lock, provided sterile
two 22G needles provided sterile
two sterile needles (e.g. 20G×70 mm), e.g. STERICAN® needles by B. Braun
two radioprotective syringe holders, e.g. polymethylmethacrylate (PMMA) cylinders:
   one cylinder for the 2 ml. glue syringe (Cylinder "A")
   one cylinder for the for 1 ml. syringe (Cylinder "B")
1 sterile radio-protected box (for the transport in OR) not provided by BetaGlue;

The kit may optionally comprise the following components, though in other examples, these components may be provided sourced separately:
one vial of $^{90}$Y microspheres, such as SIR-SPHERES®, containing 3 GBq+/−10% in 5 ml. of Water For Injection (WFI), provided in a lead pot
one syringe of two-component glue in a capped dual-chamber syringe (2 ml.), such as a 2 mL syringe of BIOGLUE®, provided in a box and/or other packaging In addition, to the above kit, healthcare providers or sites licensed or authorized to provide radiotherapy will also have available and will use during the procedure:
a sterile radio-protected box or container for transport of the vial of $^{90}$Y microspheres
a radio-protected waste receptacle
forceps or tongs used to handle the vial of $^{90}$Y microspheres
a dose calibrator to measure radioactivity, such as a gamma camera
alcohol pad To initially prepare the radiotherapy for use:
1. Open the box containing the glue syringe packaging
2. Open the packaging containing the glue syringe in sterile fashion
3. Remove the cap of the glue syringe
4. Place the syringe of glue in its PMMA cylinder (Cylinder "A")
5. Open the lead pot containing the vial of $^{90}$Y microspheres and remove the vial from the pot using the forceps
6. Using a dose calibrator, measure the radioactivity of the $^{90}$Y microspheres vial and confirm the radioactivity (measurement should report 3GBq+/−10%)
7. Place the vial back in the lead pot
8. Partially remove any protective materials from around the vial and clean the vial with an alcohol pad
9. Place one of the 20G needles into the vial to reach the $^{90}$Y microspheres and insert one of the 22G needles in the vial for ventilation
10. Place a 1 mL syringe into its PMMA cylinder (Cylinder "B")
11. Shake the lead pot with circulating movements for at least 10 seconds.
12. Connect the 1 mL syringe to the 20G needle and draw the amount of $^{90}$Y microspheres for the glutaraldehyde chamber of the glue syringe according to the quantity reported in the below, for a glue syringe of 2 mL
13. Inject the $^{90}$Y microspheres into the glutaraldehyde component chamber of the glue syringe and dispose of the empty 1 mL syringe in a radio-protected waste box, without disposing the PMMA cylinder (Cylinder "B") that contained the 1 mL syringe
14. Place the second 1 mL syringe into the PMMA cylinder (Cylinder "B") and connect the second 20G×70 mmm needle
15. Agitate or shake the lead pot with circulating movements for at least 10 seconds
16. With the 1 mL syringe, draw the amount of $^{90}$Y microspheres for the bovine serum albumin (BSA) chamber of the two-component glue syringe according to the quantity reported in tables above (for a two-component glue syringe of 2 mL). Adjust for any $^{90}$Y decay 17. Inject the $^{90}$Y microspheres into the BSA component chamber of the two-component glue syringe and dispose of the empty 1 mL syringe with the 20G×70 mm needle in a radio-protected waste receptacle. Do not dispose of the cylinder shield.
18. Connect the mixing tip to the two-component glue syringe, now contains the pre-loaded glue and the $^{90}$Y microspheres in the BSA component chamber
19. Using the dose calibrator, measure the radioactivity of the $^{90}$Y-matrix syringe using a gamma camera and place the syringe in the radio-protected box. The $^{90}$Y-matrix syringe is now ready to be transported to the operating or procedure room.

The actual amount to be injected will be decided by the nuclear medicine specialist performing the procedure of radio-ablation, and may depend on the size of the surgical resection area (tumor bed) to be ablated and on clinical judgment. Before the delivery of therapy, the system may be further assembled with an exemplary mixing tip as described below:

1. Remove the radio-protective PMMA cylinder containing the prepared $^{90}$Y-matrix syringe from the radio-protective box, holding the syringe in the PMMA cylinder upright through the entire dispensing process to maintain any air bubbles in the upper part of the syringe
2. Open the sterile packaging containing the mixing tip and remove the mixing tip from the packaging, checking the mixing tip collar to ensure that the pointer on the collar is directly above the largest of the two connection openings. If the pointer of the collar is not at the largest opening, rotate the locking collar on the tip body until the pointer is above the largest connection opening.
3. With the syringe tip in the upright position, remove the cap. Align and attach the mixing tip to the syringe
4. Lock the mixing tip by pushing the mixing tip firmly onto the syringe and rotating the mixing tip locking collar.
5. Keeping the syringe upright, align the dual plunger heads to the corresponding large and small syringe. Insert and push the plunger into the back of the syringe until resistance is met, and then optionally recap the syringe.

Once the $^{90}$Y-matrix syringe is assembled, the $^{90}$Y radiotherapy may be administered via the following exemplary procedure:

1. Agitate the $^{90}$Y-matrix syringe for at least 5 seconds, while the $^{90}$Y-matrix syringe remains inserted in its PMMA cylinder
2. Remove the cap from the $^{90}$Y-matrix syringe if needed
3. Push the plunger to remove any air bubbles
4. Apply the $^{90}$Y-matrix immediately to the surgical cavity, by pushing the plunger
5. Confirm that the $^{90}$Y-matrix has polymerized, by either waiting for a pre-determined amount of time, e.g. 60, 90, or 120 seconds, or by observing for phase changes in $^{90}$Y-matrix via an imaging modality, e.g. fluoroscopy, CT, ultrasound or endoscopy.
6. Close the surgical site by suturing, stapling or gluing
7. Place the KY-matrix syringe into the radio-protected container and dispose of it, with or without the PMMA cylinder Example 8: Hepatocellular Carcinoma In another study, microspheres pre-loaded with $^{90}$Y will be mixed with a surgical glue matrix for the radio-ablation of primary liver lesions, followed by their resection. In other variations of the study, however, resection is not necessarily performed after delivery of the radioisotope particles. Percutaneous ablation of hepatic lesions with a $^{90}$Y-matrix composition may be a more effective therapy, minimizing local or systemic side effects. The use of this novel locoregional approach seems to be appropriate for human treatment based on:

time for application, with or without ultrasound guidance, in a range between 2 to 5 min;
size of ablation, range between 3.8 to 5.3 cm in length and 4.0 to 5.0 cm in width; and
absence of systemic side effects.

The subjects selected for the study will be both ablatable (i.e., amenable to percutaneous ablation) and respectable (i.e., judged such by the liver surgeon), as shown in the inclusion criteria. They will be offered surgical resection for early stage hepato-cellular carcinoma (HCC) within the usually expected time frame (35-40 days after diagnosis/staging), but by enrolling in the study they will also be offered a minimally-invasive procedure of percutaneous β-ablation of their lesion 5-10 days after diagnosis, to be then followed by hepatic surgery around 30 days afterwards, when all activity of $^{90}$Y has long ceased (the half-life of $^{90}$Y is 64.1 hours). The surgical resection will remove the whole liver segment containing the ablated lesion, thus allowing for a complete histological examination which is, in fact, much more accurate than any type of currently available imaging to assess the outcome of the ablation procedure. This type of study is normally known as "ablate-resect" study, and there are numerous examples of its use in medicine. The subjects will be followed up for 2-3 months after surgery, following the HCC radio-ablation with the $^{90}$Y-matrix composition. The total study duration for each patient is about 14 weeks, with an enrollment period of 6 months.

The primary objective of this study is the assessment of the feasibility of this novel procedure, while the histological assessment of the resected specimen will offer useful information about its possible efficacy. If the hypothesis of a much more complete peri-HCC necrosis is supported, it will provide a more efficacious procedure of percutaneous ablation to the Early-Stage HCC population. In addition, since HCC is a complication of liver cirrhosis, the complete cure of one such lesion will have a possible impact on the outcome of cirrhotic patients, given the frequent appearance of new HCC lesions in other anatomical areas of the liver. The secondary objectives of this study include (1) to demonstrate an effective tumor mass necrosis after ablation with the $^{90}$Y-matrix composition, (2) to evaluate the histological response after ablation with the $^{90}$Y-matrix composition, (3) to evaluate the dosimetry of the $^{90}$Y-matrix composition in the target tissue, (4) to assess quality of life of enrolled patients, and (5) to assess the local and systemic toxicity of the procedure.

This is a single-center, pre-market, pilot First-In-Human study for patients who will undergo an ablate-resect procedure for primary HCC. The primary study endpoint will be the ability to reach the HCC lesion as planned and to deliver an intra-tumoral pre-determined dose of the $^{90}$Y-matrix composition without treatment-limiting clinical complications. The secondary study endpoints will be (1) the percentage of tumor mass necrosis and presence of viable cells in the treated lesion, assessed histologically after surgical resection of the segment containing the lesion, (2) the correct anatomical delivery of the $^{90}$Y-matrix composition, as confirmed by PET-scan 24-48 hours after the procedure, (3) effective delivery of a pre-determined radioactivity dose to the target tissue (measured in Gy), (4) quality of life of the enrolled patients, as measured by the EORTC QLQ C-30/HCC18 questionnaires, and (5) safety: vital signs, laboratory tests, type and severity of any adverse events associated with the procedure of radio-ablation, with the surgical resection, and occurring in the period between the two treatments.

The patient population size will be 10 adult patients, male and female, with early stage HCC. The inclusion criteria will include:

Subjects with hepatic lesions diagnosed as HCC—Early Stage;
Subjects with a maximum of 7 non-subscapsular lesions with a maximum diameter of 50 mm, considered surgically resectable according to local standards;
Subjects with at least one of the upper above mentioned lesions considered amenable to percutaneous ablation (maximum diameter 50 mm);
Adult male and female subjects (aged over 18 years)
Able to read, comprehend and willing to sign the informed consent form The exclusion criteria for the study will be:

Female subject who is pregnant or likely to become pregnant, or is breastfeeding;
Subjects who have participated in another study within the past 3 months;
Subjects not suitable for general anesthesia and abdominal surgery;
Subjects with any known allergy to the $^{90}$Y-matrix composition components, or the anesthetics;
Subjects with contraindications to the procedure because of concomitant medical problems.
Subjects with other concomitant malignancies
Any clinical or laboratory disorder which in the investigator's opinion might contraindicate the subject's participation in the study.

The study procedures will include:

Each subject will undergo imaging with Contrast-Enhanced Ultrasound (plus Histology), together with Diffusion-Weighted Magnetic Resonance Imaging (DW-MRI) or Computerized Tomography of the abdomen, in order to have the HCC lesions diagnosed and staged;
One of the lesions (considered meeting the criteria for percutaneous ablation and intra-tumoral administration of the $^{90}$Y-matrix composition) will be treated with radio-ablation using the experimental device;
The proper and effective delivery of a pre-determined dose of the $^{90}$Y-matrix composition will be assessed by PET 24-48 hrs. after the ablative procedure;
The degree of necrosis of the treated lesion will be assessed by DW-MRI 21 days after the ablative procedure;
7-9 days after DW-MRI, the whole tumor mass will be surgically resected;
The resected lesion (pre-treated with radio-ablation) will be sent for histological examination, in accordance with the procedures described in the protocol; and
Follow-up will occur 2 months after surgery.

Collected data will be summarized by descriptive statistics. Continuous variables will be presented as number of cases, mean, and standard deviation, median with interquartile range, minimum and maximum. Categorical variables will be summarized using counts of subjects and percentages. For the primary endpoint, a confidence interval (CI) for the mean delivered dose and for the standard deviation with a significance level of 5% will be estimated. Secondary endpoints will be summarized by descriptive statistics and 95% confidence intervals. Surgical specimens will be processed by the pathologist for evaluation of surgical margins and will be observed for gross changes due to necrosis. Safety assessments will include recording of all adverse events (AEs) as classified using Common Terminology Criteria for Adverse Events v5.0, as well as of changes in vital signs and laboratory parameters.

Each subject will be informed about the aims, procedures and possible risks of the study and will be asked to sign the informed consent form. Each screened subject will be identified by a progressive screening number. Subjects will be enrolled only after having signed the informed consent form before any study procedure. All the patients monitored at the investigational center will be checked for adherence to the study inclusion and exclusion criteria.

The following information will be collected:
Demographic data
Height and weight
Vital signs (e.g. blood pressure (BP); heart rate (HR); respiratory rate (RR))
ECG
General and physical examination
Medical and surgical history
Alcohol consumption check
Urine analysis, including Bence-Jones protein
Pregnancy urine test for women in fertile age
Concomitant medications/treatments
Tumor evaluation using contrast-enhanced ultrasound plus histology (if applicable)
Imaging of the liver will be made using Magnetic Resonance Imaging (MRI) or Computerized Tomography (CT)
Imaging of the tumor will be performed using a PET scan
The tumor will be staged using the TNM classification and the Barcelona Clinic staging algorithm, in addition to the mRECIST criteria
Quality of life questionnaires (EORTC-QLQ C-30) and HCC18, will be administered to the patients Patients will be instructed to contact immediately the research team in case of appearance of any adverse events, which might appear in the timeframe between initial screening and the day of the ablation procedure. On the day of the treatment with the $^{90}$Y-matrix composition, each patient will undergo a pre-procedure review that will include:

Vital signs (e.g. BP; HR; RR)
General physical examination
Tumor evaluation
PET imaging (within 24-48 hours after ablation)
Dosimetry assessment
Concomitant medications
Adverse events check
Anesthesia for the injection of the $^{90}$Y-matrix composition
Contrast-enhanced ultrasonography
Ablation by using the KY-matrix composition If all the entry criteria are fulfilled and the patients have signed the Informed Consent form, they will be scheduled for the β-ablation procedure using the $^{90}$Y-matrix composition seven days after these screening tests. Each patient will be followed-up for any adverse events or adverse effects from the informed consent signature date, during the whole study duration. A blood sample will be collected for the following determinations:

Complete blood count with differential
Electrophoretic protein pattern
Activated Partial Thromboplastin Time (APTT)
International Normalized Ratio (INR)
Fibrinogen Blood glucose
Blood urea nitrogen (BUN)
Creatinine
Serum glutamic-oxaloacetic transaminase (AST/SGOT), alanine aminotransferase (ALT/SGPT), total and fractionated bilirubin, gamma glutamyl transferase (GGT), lactate dehydrogenase (LDH), alkaline phosphatase (ALP).
Serum ions: sodium, calcium, potassium, chloride
Tumor marker (alpha-fetoprotein, AFP)

Pre-procedure checks will be performed before the performance of the ablative procedure, as follows:
Adherence to inclusion and exclusion criteria
Vital signs (BP; HR; RR)
General and physical examination
Concomitant medications/treatments The $^{90}$Y-matrix kit will include a radioisotope source and matrix source as described elsewhere herein, e.g. $^{90}$Y microspheres from Sirtex Medical (SIRPSHERES®) and BIOGLUE® from Cryolife. In addition, the kit will include a dual-lumen catheter configured to attach to the dual-chamber syringe of the BIOGLUE® to facilitate delivery of the two matrix components separately through the catheter, so that the matrix does not gel or solidify inside the catheter during delivery. The catheter features are described above, along with its introducer needle and its stylet.

For the procedure, the syringe size, 2 mL or 5 mL, of the BIOGLUE® will be selected based on the size(s) or total volume(s) of the tumor as determined on the pre-procedure work-up. The $^{90}$Y-matrix composition is prepared during the pre-procedure set-up as follows:

1. Open the box containing the vial of microspheres, leaving the vial in the lead container
2. Place on the bench in a lead or acrylic box if available
3. Partially remove the aluminum seal from the SIR-SPHERES® vial and clean with an alcohol swab
4. Insert a 25G needle into the vial septum to create an opening, making sure the needle is clearly in the contents of the vial
5. Use a 5 ml syringe screened with a 20-22G spinal needle at least 70 mm long to pierce the septum of the SIR-SPHERES® microspheres ampoule
6. Take 2 ml of suspension liquid and dispose of it
7. Using a dose calibrator, determine activity in the shipping vial and place it in the lead container
8. Determine the volume to be withdrawn to provide the required radiation dose to the hepatic lesion, depending on the size of the tumor bed.

For the calculation of the activity, a vial of SIR-SPHERES® was considered containing a concentration dose of 3 GBq/3 ml, after removal of a volume equal to 2 ml of supernatant and it was taken into account that in the dual-lumen catheter, at the end of use in patients, a volume of 158 μL remains. In other variations, however, a different amount of supernatant may be removed or added, or not changed at all. For tumor sizes less than 30 mm diameter, a 2 mL syringe is selected, and assuming that the SIR-SPHERES® and BIOGLUE® are uniformly mixed and the maximum amount of the mixture is dispensed, leaving a nominal 158 μL residual of the mixture in the catheter:

| Tumor diameter (mm) | Expected Syringe Activity (MBq) | Amount $^{90}$Y suspension withdrawn (μL) | Subvolumes of $^{90}$Y suspension loaded into each syringe chamber | | Combined Volume (μL) | Injected Activity (MBq) | Residual Activity (MBq) |
|---|---|---|---|---|---|---|---|
| | | | BSA (μL) | Glutaraldehyde (μL) | | | |
| 0.5 | 0.48 | 0.48 | 0.38 | 0.10 | 2.0005 | 0.44 | 0.04 |
| 10 | 2.4 | 2.4 | 1.9 | 0.5 | 2.002 | 2.2 | 0.2 |
| 15 | 7.03 | 7 | 5.6 | 1.4 | 2.007 | 6.48 | 0.6 |
| 20 | 15.75 | 15.8 | 12.6 | 3.2 | 2.016 | 14.5 | 1.2 |
| 25 | 29.82 | 29.8 | 23.9 | 6.0 | 2.030 | 27.5 | 2.3 |

For tumor sizes from 50 mm radius to 70 mm radius or higher, a 5 mL syringe is selected, and assuming that the SIR-SPHERES® and BIOGLUE® are uniformly mixed and the maximum amount of the mixture is dispensed, leaving a nominal 300 μL residual of the mixture in the syringe:

| Tumor radius (mm) | Expected Syringe Activity (MBq) | Amount $^{90}$Y suspension withdrawn (μL) | Subvolumes of $^{90}$Y suspension loaded into each syringe chamber | | Combined Volume (μL) | Injected Activity (MBq) | Residual Activity (MBq) |
|---|---|---|---|---|---|---|---|
| | | | BSA (μL) | Glutaraldehyde (μL) | | | |
| 25 | 28.4 | 28.4 | 22.7 | 5.7 | 5.028 | 27.5 | 0.9 |
| 30 | 48.4 | 48.4 | 38.7 | 9.7 | 5.048 | 46.9 | 1.5 |
| 35 | 75.45 | 75.5 | 60.4 | 15.1 | 5.075 | 73.1 | 2.3 |
| 40 | 113.6 | 11.6 | 90.8 | 22.7 | 5.114 | 110 | 3.5 |
| 45 | 159.9 | 159.9 | 127.9 | 32 | 5.160 | 155 | 4.9 |
| 50 | 218.6 | 218.6 | 174.9 | 43.7 | 5.219 | 212 | 6.6 |

9. Insert the syringe back into the vial and move the plunger back and forth to thoroughly mix the SIR-SPHERES® beads. Rapidly withdraw the pre-calculated radiation dose and proceed with the transfer to the BIOGLUE® chambers as described below.

10. Remove the cap of the double-chamber syringe containing the glue components.
11. Distribute the microspheres in the double-chamber syringe respecting the 4:1 ratio (80% in the BSA chamber, 20% in the glutaraldehyde chamber).
12. Put the cap back on the syringe.
13. Check the patient's dose by re-evaluating the activity in the syringe with the dose calibrator and correct if necessary.
14. Place the syringe in a radioprotected container suitable for transport in the operating room/radiology suite.

For the administration of $^{90}$Y-matrix composition for percutaneous ablation, the use of the MIPP-Kit by SVAS Biosana system, depicted in FIGS. 1A and 1B, are used as it is specifically designed for optimal use with BIOGLUE® for percutaneous application, with the following sized components:

Introducer needle: 15G diameter and 150 mm length
Injector catheter: 16G diameter and 120 mm length The procedure would continue as follows:

15. Percutaneous access should be achieved to facilitate insertion of the needle catheter into the hepatic parenchyma.
16. Appropriate anesthesia should be used, as per the standard operational approach at the Center.
17. Place the kit's introducer and stylet in the liver lesion with the aid of an ultrasound scanner or under CT guidance or other imaging modality.
18. Remove sterile syringe containing the $^{90}$Y-matrix composition components from the radio-protected container.
19. Remove the syringe cap containing the $^{90}$Y-matrix composition components.
20. Holding the syringe firmly with the pin facing up, rotate the cap 90° counterclockwise and remove the cap by swinging it from side to side. Align the dual-lumen catheter of the kit with the syringe using the corresponding notches on each and place the end of the dual-lumen catheter of the kit on the syringe. Take care not to accidentally spill the solution from the syringe during assembly.
21. Lock the bilateral catheter of the kit in place by pushing the catheter firmly towards the syringe and rotating the catheter collar 90° clockwise.
22. Keeping the syringe straight, align the large and small reservoirs of the solution syringe over the corresponding syringe plunger heads. Slide the plunger towards the back of the syringe until it meets resistance. The dispensing device is thus assembled.
23. Remove the stylet of the introducer of the kit.
24. Insert the catheter into the introducer and lock it through the Luer-lock fitting.
25. Press the plunger to dispense the mixture.
26. The plunger should be pressed at a speed in the range of 0.5 and 1.0 mm/s
27. Wait at least 30 seconds before retracting the introducer while providing a slight rotation to prevent the glue from adhering the introducer with the tissue.
28. At the end of the procedure, the needle catheter and syringe should be disposed of following the standard operating procedure of the biohazard handling center.
29. The insertion site must be properly closed and protected by bandaging
30. It is possible to administer topical antibiotics, if deemed appropriate.

The preparation and implantation procedure must be considered as a potential radiation hazard for personnel and a serious risk of contamination. Local guidelines on the use of radiation with regard to implantation and post-implant care should be followed.

The delivery of the $^{90}$Y-matrix composition will be evaluated using PET scanning 24-48 hours after the procedure. Dosimetry will be analyzed through mathematical analysis of the data acquired from the PET scan.

Each patient will also be re-evaluated after 21 days for tumor evaluation, prior to surgical resection, which will include contrast enhanced ultrasound, MRI and/or CT imaging, and a clinical evaluation. Dosimetry will be re-assessed using a PET scan with mathematical analysis of the data. The site of insertion and the liver tissue will be monitored for changes during the time between radio-ablation and excision. Any morbidity and/or complications observed must be recorded on the CRFs. Additional evaluation will include:

Vital signs (e.g. BP; HR; RR)
General physical examination
Complete lab tests (e.g. blood chemistry and hematology parameters)
mRECIST criteria
Concomitant medications
Adverse events check
EORTC-30/HCC18 questionnaires Seven to nine days after the re-evaluation, i.e. 28-30 days after the ablation procedure, the patient will return to hospital for the target lesion surgical resection, which will be performed as per standard procedure of the investigation site. The surgery procedure will include:

Vital signs (BP; HR; RR)
General physical examination
Tumor evaluation
Anesthesia for surgery purpose
Surgery
Histological assessment
Concomitant medications
Adverse events check From a radioprotection perspective, the surgery is radiologically safe for the surgeon and all the ancillary personnel, because after 20 days, the residual emission after a 2GBq dose of $^{90}$Y injected during the procedure of radio-ablation is reduced to 10 MBq. The effect at 1 meter is approximately 3mSv/h in vitro, and approximately 1 mSv/h in vivo (in the human body), both below the background environmental radiation level.

In case surgery becomes contraindicated at the due date, the subject will be withdrawn from the study, but will undergo the same assessments as described for the post-surgery evaluation and followed up for any safety issues.

The resected liver tissue will be sent to the Pathology Department for assessment. Specimens will be processed by the pathologist for evaluation of surgical margins and will be observed for gross changes due to necrosis. The percentage of tumor mass necrosis will be measured, and the presence of any viable cells in the treated lesion will be assessed histologically. The radial distribution of the $^{90}$Y microspheres will also be assessed and measured. Sample orientation will be performed using an appropriate system, such as color inking. Resection margins will be assessed through imaging (when appropriate), grossly, and microscopically. The liver specimen, including the treated liver tissue, will be processed for and evaluated by microscopic examination. After sample orientation, the specimen will be observed for gross changes due to the necrosis, and then tissue within the treated region will be microscopically examined for induced tissue necrosis. The extent of necrosis will be determined using Hematoxylin/Eosin staining technique, which relies on visual examination of the condition of cell membranes and structures in order to assess the viability of cells, and standard immunohistochemistry.

For the same reasons that the surgery is radiologically safe, the histopathological assessment is also safe for the pathologist and all the ancillary personnel.

The patient care following surgery will follow the local standard routine and practices, involving (where appropriate) admission to the intensive care unit for 24-48 h after surgery, before being transferred to the hospital regular ward, where patients will undergo the following assessments before discharge:

Vital signs (e.g. BP, HR, RR)
ECG
Physical examination
Blood chemistry (including liver function assessments: AST, ALT, total and fractionated bilirubin, Gamma GT, LDH, alkaline phosphatase) and hematology
Surgical down staging criteria
Concomitant medications/treatments
Tumor evaluation using contrast-enhanced ultrasound
Adverse events and adverse effects check After discharge, patients will be followed up for 2 months. The study will be considered concluded for each subject after the 2 months follow-up period; during the follow-up period, information will be collected on any adverse events which might be related with the radio-ablation procedure or the surgical resection and included in the CRFs.

During the post-discharge follow-up visit, which will occur 28 days after the surgery, 56 days after ablation, the patients will undergo the following study procedures:

Vital signs (e.g. BP, HR; RR)
General physical examination, weight
Complete lab tests (e.g. blood chemistry and hematology parameters)
Tumor evaluation
Imaging evaluation (e.g. PET scan)
Concomitant medications
Adverse events check In order to evaluate the primary endpoint, a confidence interval (CI) for the mean delivered dose with a significance level of 5% will be estimated. In addition, standard deviation of the mean value of delivered dose and its 95% confidence interval will be calculated in order to quantify the dispersion and the dynamic range of the performance of the new technology. Secondary endpoints will be summarized by descriptive statistics and 95% confidence intervals, as appropriate. Quality of life, as measured by the EORTC QLQ C30 and HCC18 questionnaires, will be evaluated at screening visit (V-1) and Visit 1 (V1). Descriptive statistics of single item score at each study visit and change of scores at V1 versus scores at screening visit (V-1) will be provided. Surgical specimens will be processed by the pathologist for evaluation of surgical margins and will be observed for gross changes due to necrosis. Safety assessments will consist of recording and tabulating all adverse events, as well as with an analysis of changes in vital signs and laboratory parameters. Incidence of adverse events, with regards also to the relationship with the $^{90}$Y-matrix composition, will be calculated for all patients, along with their severity and the seriousness. The severity assessment for an adverse event or serious adverse event should be completed using the NCI CTCAE Version 5. Laboratory data will be summarized by type of laboratory test. Descriptive statistics will be calculated for each laboratory analyte at baseline and for observed values and changes from baseline at each scheduled time point. A listing of subjects with any laboratory results outside the reference ranges will be provided. Parameters with predefined NCI-CTCAE toxicity grades will be summarized. Descriptive statistics of vital signs values and changes from baseline will be summarized. Descriptive statistics will be provided for safety variables.

Although the foregoing implementations has, for the purposes of clarity and understanding, been described in some detail by the use of illustration and example, it will be apparent that certain changes and modifications may be practiced, and are intended to fall within the scope of the appended claims. Additionally, it should be understood that the components and characteristics of the devices and materials described herein may be used in any combination, and the methods described herein may comprise all or a portion of the elements described herein. The description of certain elements or characteristics with respect to a specific figure are not intended to be limiting or nor should they be interpreted to suggest that the element cannot be used in combination with any of the other described elements.

What is claimed is:

1. A method of treating breast cancer, comprising:
    determining an average tumor size of a breast cancer lesion;
    selecting a $^{90}$Y syringe activity level and a $^{90}$Y treatment activity level using the average tumor size, wherein the $^{90}$Y treatment activity level is:
    a. 15 MBq to 20 MBq for the average tumor size corresponding to a radius in the range of 20 mm to 24 mm;
    b. 20 MBq to 25 MBq for the average tumor size corresponding to a radius in the range of 25 mm to 29 mm;
    c. 25 MBq to 35 MBq for the average tumor size corresponding to a radius in the range of 30 mm to 34 mm;
    d. 40 MBq to 50 MBq for the average tumor size corresponding to a radius in the range of 35 mm to 39 mm;
    e. 55 MBq to 65 MBq for the average tumor size corresponding to a radius in the range of 40 mm to 44 mm;
    f. 75 MBq to 85 MBq for the average tumor size corresponding to a radius in the range of 45 mm to 49 mm;
    g. 90 MBq to 100 MBq for the average tumor size corresponding to a radius in the range of 50 mm to 54 mm;
    loading a dual chamber syringe with the selected $^{90}$Y syringe activity level, wherein the dual chamber syringe comprises a first chamber pre-loaded with bovine serum albumin and a second chamber pre-loaded with glutaraldehyde; and
    injecting the selected $^{90}$Y treatment activity level at a treatment site of the breast cancer lesion using the dual chamber syringe.

2. The method of claim 1, wherein the $^{90}$Y syringe activity level is:
    a. 20 MBq for the average tumor size corresponding to a radius in the range of 20 mm to 24 mm;
    b. 25 MBq for the average tumor size corresponding to a radius in the range of 25 mm to 29 mm;
    c. 35 MBq for the average tumor size corresponding to a radius in the range of 30 mm to 34 mm;

d. 50 MBq for the average tumor size corresponding to a radius in the range of 35 mm to 39 mm;
e. 70 MBq for the average tumor size corresponding to a radius in the range of 40 mm to 44 mm;
f. 90 MBq for the average tumor size corresponding to a radius in the range of 45 mm to 49 mm; and
g. 110 MBq for the average tumor size corresponding to a radius in the range of 50 mm to 54 mm.

3. The method of claim 1, further comprising:
a. adjusting a concentration of a $^{90}Y$ source before withdrawing the selected $^{90}Y$ syringe activity level, wherein adjusting the concentration comprises:
  i. adding 5 mL of water to the $^{90}Y$ source; or
  ii. adjusting the concentration of the $^{90}Y$ source to 3 GBq/10 mL; and
b. withdrawing the selected $^{90}Y$ syringe activity level from the $^{90}Y$ source.

4. The method of claim 1, further comprising determining a volume of the $^{90}Y$ syringe activity level for withdrawal based on $^{90}Y$ decay and the average tumor size.

5. The method of claim 1, wherein loading the dual chamber syringe comprises loading the $^{90}Y$ syringe activity level into the first and second chambers of the dual chamber syringe in a 1:4 ratio.

6. The method of claim 1, further comprising:
placing the dual chamber syringe into a first radio-protective container before loading the dual chamber syringe with the selected $^{90}Y$ syringe activity level;
placing a transfer syringe into a second radio-protective container; and
using the transfer syringe to load the dual chamber syringe.

7. The method of claim 6, wherein the first and second radio-protective containers comprise PMMA cylinders.

8. The method of claim 1, further comprising:
confirming a source activity level of a $^{90}Y$ source;
withdrawing the $^{90}Y$ syringe activity level from the $^{90}Y$ source; and
confirming the syringe activity level of the dual chamber syringe after loading the dual chamber syringe.

9. The method of claim 1, further comprising confirming a residual activity level of the dual chamber syringe after injecting the treatment site.

10. The method of claim 1, wherein the breast cancer is ductal carcinoma in situ.

11. The method of claim 1, wherein the treatment site is a post-resection treatment site of the breast cancer lesion.

* * * * *